United States Patent [19]

Engel et al.

[11] Patent Number: 6,046,137
[45] Date of Patent: Apr. 4, 2000

[54] HERBICIDAL HETEROCYCLICALLY SUBSTITUTED BENZOYLISOTHIAZOLES

[75] Inventors: Stefan Engel, Idstein; Wolfgang von Deyn, Neustadt; Regina Luise Hill, Speyer; Uwe Kardorff, Mannheim; Martina Otten, Ludwigshafen; Peter Plath, Frankenthal; Marcus Vossen, Mannheim; Ulf Misslitz, Neustadt; Helmut Walter, Obrigheim; Karl-Otto Westphalen, Speyer, all of Germany

[73] Assignee: BASF Aktiengesellschaft, Ludwigshafen, Germany

[21] Appl. No.: 09/171,199

[22] PCT Filed: Apr. 14, 1997

[86] PCT No.: PCT/EP97/01855

§ 371 Date: Oct. 15, 1998

§ 102(e) Date: Oct. 15, 1998

[87] PCT Pub. No.: WO97/38996

PCT Pub. Date: Oct. 23, 1997

[30] Foreign Application Priority Data

Apr. 16, 1996 [DE] Germany ............ 196 14 858

[51] Int. Cl.[7] .................. A01N 43/80; C07D 417/10
[52] U.S. Cl. .................. 504/266; 504/269; 548/204; 548/214
[58] Field of Search .................. 548/214, 204; 504/266, 269

[56] References Cited

U.S. PATENT DOCUMENTS

| | | | |
|---|---|---|---|
| 4,187,099 | 2/1980 | Franz et al. | 71/90 |
| 5,034,385 | 7/1991 | Dininno et al. | 514/210 |
| 5,846,907 | 12/1998 | Von Deyn | 504/221 |

FOREIGN PATENT DOCUMENTS

| | | |
|---|---|---|
| 418175 | 3/1991 | European Pat. Off. |
| 449223 | 10/1991 | European Pat. Off. |
| 487357 | 5/1992 | European Pat. Off. |
| 524781 | 1/1993 | European Pat. Off. |
| 527036 | 2/1993 | European Pat. Off. |
| 527037 | 2/1993 | European Pat. Off. |
| 560482 | 9/1993 | European Pat. Off. |
| 580439 | 1/1994 | European Pat. Off. |
| 588357 | 3/1994 | European Pat. Off. |
| 609797 | 8/1994 | European Pat. Off. |
| 609798 | 8/1994 | European Pat. Off. |
| 617010 | 9/1994 | European Pat. Off. |
| 636622 | 2/1995 | European Pat. Off. |
| 2284600 | 6/1995 | United Kingdom. |
| 94/14782 | 7/1994 | WIPO. |
| 94/18179 | 8/1994 | WIPO. |
| 95/15691 | 6/1995 | WIPO. |
| 95/16678 | 6/1995 | WIPO. |
| 95/22903 | 8/1995 | WIPO. |
| 95/22904 | 8/1995 | WIPO. |
| 95/25105 | 9/1995 | WIPO. |
| 96/26192 | 8/1996 | WIPO. |

*Primary Examiner*—Robert Gerstl
*Attorney, Agent, or Firm*—Keil & Weinkauf

[57] ABSTRACT

4-Benzoylisothiazoles of the general formula 1

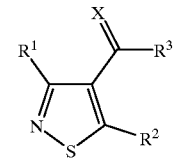

where the substituents have the following meanings:
X is oxygen or sulfur;
$R^3$ is a radical of the general formula 2

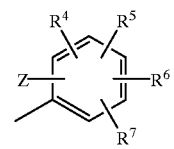

where Z and the substituents $R^1$, $R^2$, $R^4$, $R^5$, $R^6$ and $R^7$ have the meanings given in claim 1,
salts of the 4-benzoylisothiazoles of the general formula 1 which are conventionally used in agriculture, their preparation, and their use as herbicides.

17 Claims, No Drawings

HERBICIDAL HETEROCYCLICALLY SUBSTITUTED BENZOYLISOTHIAZOLES

The present invention relates to novel substituted benzoylisothiazoles, to processes for their preparation and to their use as herbicides.

The patent literature (EP 0 527 036, EP 0 527 037, EP 0 560 482, EP 0 580 439, EP 0 588 357, EP 609 797, EP 0 609 798, EP 0 636 622, WO 94/14782, WO 94/18179, WO 95/15691 and WO 95/16678) discloses that substituted 4-benzoyl-5-cycloalkylisoxazoles represent a class of compounds with pronounced herbicidal activity pre-emergence. 4-(2-Sulfonylmethyl-4-trifluoromethylbenzoyl)-5-cyclopropyl-isoxazole, a representative class of compounds, is being developed by Rhône-Poulenc as a pre-emergence herbicidally active ingredient against mono- and dicotyledon harmful plants in maize. (RPA 201772, Technical Bulletin).

Moreover, the herbicidal and insecticidal activity of substituted 4-alkyl- and 4-cycloalkyl-5-aryl- or -5-hetaryl-isoxazole has been disclosed (GB 2 284 600, WO 95/22903, WO 95/22904 and WO 95/25105).

The herbicidal activity of the known compounds is not only insufficient post-emergence, but also only partially satisfactory pre-emergence combined with incomplete crop plant compatibility.

Herbicidal or insecticidal 4-benzoylisothiazoles according to the invention cannot be found in the prior art as yet.

As yet, 4-benzoylisothiazoles have only been of limited interest as far as synthesis is concerned. While substituted isothiazoles and their carbocycle-fused derivatives have been the aim of basic investigations (for example: D. L. Pain, B. J. Peart, K. R. H. Wooldridge, Comprehensive Heterocyclic Chemistry, Vol. 6, Part 4B, p. 131, Ed. A. R. Katritzky, Pergamon Press, Oxford, 1984), only individual cases of acylated and, in particular, benzoylated derivatives have been described in the literature (for example: A. J. Layton, E. Lunt, J. Chem. Soc. (1968) 611, A. Alberola, F. Alonso, P. Cuadrado, C. M. Sanudo, Synth. Commun. 17 (1987) 1207, A. Alberola, F. Alonso, P. Cuadrado, C. M. Sanudo, J. Heterocycl. Chem. 25 (1988) 235).

Some hydroxypropylaminocarbonyl-substituted 4-benzoylisothiazoles have been investigated in EP 0 524 781 and EP 0 617 010 as muscle relaxants and as suitable therapeutic amides for incontinence. EP 0 449 223 maintains that 3,5-di(tertiary-butyl)-4-hydroxybenzoylisothiazoles, being 5-lipoxygenase and cyclooxygenase inhibitors, have an antiinflammatory action.

U.S. Pat. No. 5,034,385 discloses that carbapenem-substituted benzoylisothiazoles have an antibacterial activity.

It is an object of the present invention to provide novel herbicidally active substances with an improved profile of action and crop plant compatibility.

We have found that this object is achieved by the benzoylisothiazoles of the general formula 1 according to the invention, which, surprisingly, have crop plant compatibility combined with a pronounced herbicidal activity against harmful plants.

The present invention relates to 4-benzylisothiazoles of the general formula 1

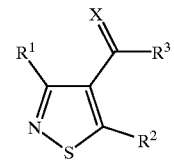

where the substituents have the following meanings:
X is oxygen or sulfur;
$R^1$ is hydrogen, alkyl, alkenyl, alkynyl; unsubstituted or substituted alkoxycarbonyl; unsubstituted or substituted aryl, unsubstituted or substituted heterocyclyl or unsubstituted or substituted hetaryl;
$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl; aryl, it being possible for this radical to have attached to it one or more of the following groups: alkyl, alkenyl, alkynyl, alkoxy, alkenyloxy, alkynyloxy, alkylthio or alkenylthio, it being possible for these radicals to be partially or fully halogenated or to have attached to them one or more of the following groups: alkoxy, alkenyloxy, aryloxy, alkylsulfonyl, alkenylsulfonyl or arylsulfonyl; alkylsulfonyl or alkoxycarbonyl; unsubstituted or substituted aryloxy or unsubstituted or substituted arylthio; unsubstituted or substituted mono- or dialkylamino, unsubstituted or substituted mono- or diarylamino or unsubstituted or substituted N-alkyl-N-arylamino, it being possible for alkyl and aryl to be identical or different; halogen, cyano or nitro;
hetaryl or heterocyclyl, it being possible for these radicals to be partially or fully halogenated or to have attached to them one or more of the following groups: alkyl, alkoxy or aryl, and it being possible, in the case of heterocyclyl, for at least one of the nitrogen atoms to have attached to them one of the following groups:
alkyl, alkenyl, alkynyl, cycloalkyl, haloalkyl, alkoxy, alkenyloxy, alkynyloxy, cycloalkyloxy, haloalkoxy, unsubstituted or substituted aryl or unsubstituted or substituted aryloxy;
$R^3$ is a radical of the general formula 2

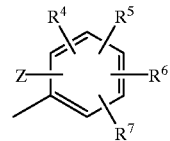

where the substituents have the following meanings:
Z is a 5- or 6-membered heterocyclic, saturated or unsaturated radical containing one to three hetero atoms selected from the group consisting of oxygen, sulfur or nitrogen and which is unsubstituted or substituted by halogen, cyano, nitro, a group —CO—$R^8$, alkyl, haloalkyl, cycloalkyl, alkoxy, haloalkoxy, alkylthio, haloalkylthio, dialkylamino or by phenyl which is unsubstituted or substituted by halogen, cyano, nitro, $C_1$–$C_4$-alkyl— or $C_1$–$C_4$-halo— alkyl-substituted phenyl or by an oxo group—which may, in the tautomeric form, also be present in the form of a hydroxyl group—or which together with a fused halogen-, cyano-, nitro-, alkyl- or haloalkyl-substituted phenyl ring, a fused carbocycle or a fused second heterocycle which is unsubstituted or substituted by halogen, cyano, nitro, alkyl, dialkylamino, alkoxy, haloalkoxy or haloalkyl, forms a bicyclic system, $R^4$–$R^7$ can be identical or different and independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, cyano or nitro, or one of the following groups:

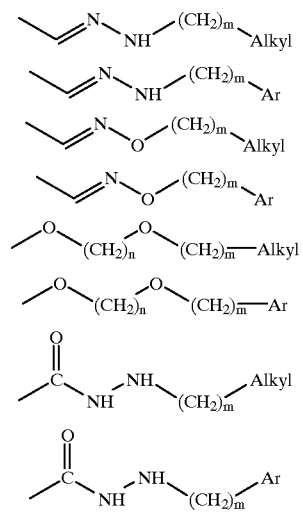

n = 1, 2, 3; m = 0, 1, 2, 3

$R^4$, $R^5$ together can form a five- or six-membered saturated or unsaturated aromatic or non-aromatic unsubstituted or substituted alkylene, alkenylene or alkdienylene chain;

$R^8$ alkyl, haloalkyl, alkoxy, or $NR^9R^{10}$, $R^9$ hydrogen or alkyl, $R^{10}$ alkyl, and to salts of the 4-benzoylisothiazoles of the general formula 1 which are conventionally used in agriculture.

Collective terms which generally represent the groups given below were used in the definitions of the compounds I given at the out-set:

halogen: fluorine, chlorine, bromine and iodine;

alkyl: straight-chain or branched alkyl groups having 1 to 6 or 10 carbon atoms, e.g. $C_1$–$C_6$-alkyl, such as methyl, ethyl, propyl, 1-methylethyl, butyl, 1-methyl-propyl, 2-methylpropyl, 1,1-dimethylethyl, pentyl, 1-methylbutyl, 2-methylbutyl, 3-methylbutyl, 2,2-dimethyipropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkylamino: an amino group which has attached to it a straight-chain or branched alkyl group having 1 to 6 carbon atoms as mentioned above;

dialkylamino: an amino group which has attached to it two independent straight-chain or branched alkyl groups having in each case 1 to 6 carbon atoms as mentioned above;

alkylcarbonyl: straight-chain or branched alkyl groups having 1 to 10 carbon atoms which are bonded to the skeleton via a carbonyl group (—CO—);

alkylsulfonyl: straight-chain or branched alkyl groups having 1 to 6 or 10 carbon atoms which are bonded to the skeleton via a sulfonyl group (—SO$_2$—);

alkylsulfoxyl: straight-chain or branched alkyl groups having 1 to 6 carbon atoms which are bonded to the skeleton via a sulfoxyl group (—S(=O)—);

alkylaminocarbonyl: alkylamino groups having 1 to 6 carbon atoms as mentioned above which are bonded to the skeleton via a carbonyl group (—CO—);

dialkylaminocarbonyl: dialkylamino groups having in each case 1 to 6 carbon atoms per alkyl radical as mentioned above which are bonded to the skeleton via a carbonyl group (—CO—);

alkylaminothiocarbonl: alkylamino groups having 1 to 6 carbon atoms as mentioned above which are bonded to the skeleton via a thiocarbonyl group (—CS—);

dialkylaminothiocarbonyl: dialkylamino groups having in each case 1 to 6 carbon atoms per alkyl radical as mentioned above which are bonded to the skeleton via a thiocarbonyl group (—CS—);

haloalkyl: straight-chain or branched alkyl groups having 1 to 6 carbon atoms, it being possible for some or all of the hydrogen atoms in these groups to be replaced by halogen atoms as mentioned above, e.g. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms as mentioned above which are bonded to the skeleton via an oxygen atom (—O—), e.g. $C_1$–$C_6$-alkoxy, such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

alkoxycarbonyl: straight-chain or branched alkyl groups having 1 to 6 carbon atoms which are bonded to the skeleton via an oxycarbonyl group (—OC(=O)—);

haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

alkylthio: straight-chain or branched alkyl groups having 1 to 4 or 6 carbon atoms as mentioned above which are bonded to the skeleton via a sulfur atom (—S—), e.g.

$C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-di-methylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, e.g. cyclopropyl, cyclobutyl, cyclopentyl and cyclohexyl;

alkenyl: straight-chain or branched alkenyl groups having 2 to 6 or 10 carbon atoms and a double bond in any position, e.g. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: straight-chain or branched alkenyl groups having 2 to 6 carbon atoms and a double bond in any position which are bonded to the skeleton via an oxygen atom (—O—);

alkenylthio and alkenylamino: straight-chain or branched alkenyl groups having 2 to 6 carbon atoms and a double bond in any position which are bonded to the skeleton (alkenylthio) via a sulfur atom or (alkenylamino) a nitrogen atom.

alkenylcarbonyl: straight-chain or branched alkenyl groups having 2 to 10 carbon atoms and a double bond in any position which are bonded to the skeleton via a carbonyl group (—CO—);

alkynyl: straight-chain or branched alkynyl groups having 2 to 10 carbon atoms and a triple bond in any position, e.g. $C_2$–$C_6$-alkynyl, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4- pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy: alkynylthio and alkynylamino: straight-chain or branched alkynyl groups having 2 to 6 carbon atoms and a triple bond in any position which are bonded to the skeleton (alkynyloxy) via an oxygen atom, (alkynylthio) via a sulfur atom or (alkynylamino) via a nitrogen atom.

alkynylcarbonyl: straight-chain or branched alkynyl groups having 3 to 10 carbon atoms and a triple bond in any position which are bonded to the skeleton via a carbonyl group (—CO—);

cycloalkenyl: cycloalkenyloxy. cycloalkenylthio and cycloalkenylamino: monocyclic alkenyl groups having 3 to 6 carbon ring members which are bonded to the skeleton directly, (cycloalkenyloxy) via an oxygen atom, (cycloalkenylthio) via a sulfur atom or (cycloalkenylamino) via a nitrogen atom, e.g. cyclopropenyl, cyclobutenyl, cyclopentenyl or cyclohexenyl;

cycloalkoxy: cycloalkylthio and cycloalkylamino: monocyclic alkyl groups having 3 to 6 carbon ring members which are bonded to the skeleton (cycloalkyloxy) via an oxygen atom or (cycloalkylthio) via a sulfur atom or (cycloalkylamino) via a nitrogen atom, e.g. cyclopropyl, cyclobutyl, cyclopentyl or cyclohexyl;

cycloalkylcarbonyl: cycloalkyl groups as defined above which are bonded to the skeleton via a carbonyl group (—CO—);

cycloalkoxycarbonyl: cycloalkoxy groups as defined above which are bonded to the skeleton via a carbonyl group (—CO—);

alkenyloxycarbonyl: alkenyloxy groups as defined above which are bonded to the skeleton via a carbonyl group (—CO—);

alkynyloxvcarbonyl: alkynyloxy groups as defined above which are bonded to the skeleton via a carbonyl group (—CO—);

heterocyclyl: three- to six-membered saturated or partially unsaturated mono- or polycyclic heterocycles which contain 1 to 3 hetero atoms selected from a group consisting of oxygen, nitrogen and sulfur and which are bonded to the skeleton directly via carbon, e.g. 2-tetrahydrofuranyl, oxyranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxaiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, aryl and aryloxy, arylthio, arylcarbonyl, aryloxycarbonyl, arylsulfonyl and arylsulfoxyl: aromatic mono- or polycyclic hydrocarbon radicals which are bonded to the skeleton directly or (aryloxy) via an oxygen atom (—O—) or (arylthio) via a sulfur atom (—S—), or (arylcarbonyl) via a carbonyl group (—CO—), or (aryloxycarbonyl) via an oxycarbonyl group (—OCO—), or (arylsulfonyl) via a sulfonyl group (—SO$_2$—) or (arylsulfoxyl) via a sulfoxyl group (—SO—), e.g. phenyl, naphthyl and phenanthrenyl, or phenyloxy, naphthyloxy and phenanthrenyloxy and the corresponding carbonyl and sulfonyl radicals;

arylamino: aromatic mono- or polycyclic hydrocarbon radicals which are bonded to the skeleton via a nitrogen atom;

hetaryl: aromatic mono- or polycyclic radicals which, besides carbon ring members, can additionally contain one to four nitrogen atoms or one to three nitrogen atoms and an oxygen or a sulfur atom or an oxygen or a sulfur atom and which are bonded to the skeleton directly via carbon, e.g.

5-membered heteroaryl, containing one to three nitrogen atoms: 5-membered heteroaryl ring groups which, besides carbon atoms, can contain one to three nitrogen atoms as ring members, e.g. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl containing one to four nitrogen atoms or one to three nitrogen atoms and one sulfur or oxygen atom or one oxygen or one sulfur atom: 5-membered heteroaryl ring groups, which, besides carbon atoms, can contain one to four nitrogen atoms or one to three nitrogen atoms and one sulfur or oxygen atom or one oxygen or sulfur member as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

carbocycle-fused 5-membered heteroaryl containing one to three nitrogen atoms or a nitrogen atom and/or an oxygen or sulfur atom: 5-membered heteroaryl ring groups which, besides carbon atoms, can contain one to four nitrogen atoms or one to three nitrogen atoms and one sulfur or oxygen atom or one oxygen or one sulfur atom as ring members and in which two adjacent carbon ring members or a nitrogen and an adjacent carbon ring member can be bridged by a buta-1,3-diene-1,4-diyl group;

6-membered heteroaryl containing one to three, or one or four, nitrogen atoms: 6-membered heteroaryl ring groups which, besides carbon atoms, can contain one to three, or one to four, nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl containing one to four nitrogen atoms: 6-membered heteroaryl ring groups in which two adjacent carbon ring members can be bridged by a buta-1,3-diene-1,4-diyl group, e.g. quinoline, isoquinoline, quinazoline and quinoxaline, and the corresponding oxy, thio, carbonyl or sulfonyl groups.

The term "partially or fully halogenated" is intended to express that in the groups characterized thus some or all of the hydrogen atoms can be replaced by identical or different halogen atoms as mentioned above.

Unsubstituted or substituted means that the organic group in question can be substituted as desired, suitable substituents being, in principle, all those listed in the present application.

Preferred substituents are hydrogen, alkyl, alkenyl, alkynyl, cycloalkyl, cycloalkylalkyl, cycloalkylalkenyl, aryl, arylalkyl, arylalkenyl, hydroxyl, alkoxy, alkenyloxy, cycloalkoxy, cycloalkylalkoxy, aryloxy, arylalkoxy, thio, alkylthio, alkenylthio, cycloalkylthio, cycloalkylalkylthio, arylthio, arylalkylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, cycloalkylamino, cycloalkenylamino, sulfonyl, alkylsulfonyl, alkenylsulfonyl, cycloalkylsulfonyl, cycloalkylalkylsulfonyl, arylsulfonyl, arylalkylsulfonyl, sulfoxyl, alkylsulfoxyl, alkenylsulfoxyl, cycloalkylsulfoxyl, cycloalkylalkylsulfoxyl, arylsulfoxyl, arylalkylsulfoxyl, alkylcarbonyl, alkenylcarbonyl, cycloalkylcarbonyl, cycloalkylalkylcarbonyl, arylcarbonyl, arylalkylcarbonyl, carboxyl, alkoxycarbonyl, alkenyloxycarbonyl, cycloalkoxycarbonyl, cycloalkylalkoxycarbonyl, aryloxycarbonyl, arylalkoxycarbonyl, aminocarbonyl, unsubstituted or substituted mono- or dialkylaminocarbonyl, unsubstituted or substituted mono- or diarylaminocarbonyl, unsubstituted or substituted n-alkyl-n-arylaminocarbonyl, it being possible for alkyl and aryl to be identical or different, alkoxyaminocarbonyl, alkenyloxycarbonylamino, cycloalkoxycarbonylamino, aryloxycarbonylamino, arylalkoxycarbonylamino, halogen, haloalkyl, haloalkenyl, unsubstituted or substituted mono- or dialkylamino, haloalkoxy, haloalkenyloxy, haloalkylthio, haloalkenylthio, haloalkylamino, haloalkenylamino, haloalkylsulfonyl, haloalkenylsulfonyl, haloalkylsulfoxyl, haloalkenylsulfoxyl, haloalkylcarbonyl, haloalkenylcarbonyl, haloalkoxycarbonyl, haloalkenyloxycarbonyl, haloalkylaminocarbonyl, haloalkenylaminocarbonyl, haloalkoxycarbonylamino, haloalkenyloxycarbonylamino, cyano or nitro.

Particularly preferred substituents are hydrogen, alkyl, alkenyl, cycloalkyl, cycloalkylalkyl, aryl, arylalkyl, hydroxyl, alkoxy, cycloalkoxy, aryloxy, thio, alkylthio, cycloalkylthio, arylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, arylsulfoxyl, alkylcarbonyl, arylcarbonyl, carboxyl, alkoxycarbonyl, aryloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, alkoxyaminocarbonyl, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkoxycarbonylamino, cyano or nitro.

Preferred with a view to their biological activity are compounds of the general formula 1 where X is oxygen.

Furthermore preferred compounds of the general formula 1 are those where $R_1$ is hydrogen or unsubstituted or substituted alkoxycarbonyl.

Preferred compounds of the general formula 1 are also those where $R^1$ is hydrogen or alkoxycarbonyl having 1 to 6 carbon atoms which can be mono- or polysubstituted by fluorine, chlorine or bromine.

Especially preferred compounds of the formula 1 are those where $R^1$ is hydrogen, methoxycarbonyl or ethoxycarbonyl.

Moreover, preferred compounds of the general formula 1 are those where $R^2$ is alkyl having 1 to 6 carbon atoms, especially preferably methyl, ethyl, isopropyl or tertiary butyl; or cycloalkyl having 3 to 6 carbon atoms, especially preferably cyclopropyl or 1-methylcyclopropyl; or phenyl, it being possible for this radical to have attached to it one or more of the following groups: alkyl, alkoxy, alkylthio, it being possible for these radicals to be partially or fully halogenated, or halogen, especially preferably 3-trifluoromethylphenyl, 2,4-difluorophenyl; hetaryl or heterocyclyl, it being possible for these radicals to be partially or fully halogenated or to have attached to them one of more of the following groups: alkyl, alkoxy or phenyl, especially preferably 1,3-benzodioxolyl, 2,2-difluoro-1,3-benzodioxolyl, 1,3-benzoxathiolyl, 3,3-dioxo-1,3-benzoxathiolyl, benzoxazolyl, pyrazolyl or thienyl.

Furthermore, preferred compounds of the general formula 1 are those where $R^3$ is a radical of the general formula 2

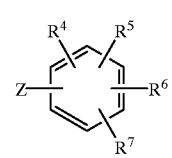

2 where the substituents have the following meanings:
Z is a 5- or 6-membered heterocyclic saturated or unsaturated radical containing one to three hetero atoms selected from the group consisting of oxygen, sulfur or nitrogen which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1C_4$-haloalkoxy, $C_1C_4$-alkylthio, $C_1$–$C_4$-haloalkylthio, di-$C_1$–$C_4$-alkylamino, unsubstituted phenyl, halogen-, cyano-, nitro-, $C_1$–$C_4$-alkyl- or $C_1$–$C_4$-haloalkyl-substituted phenyl or an oxo group which may, in the tautomeric form, also be present as a hydroxyl group or which together with a fused, unsubstituted or halogen-, cyano-, nitro-, $C_1$–$C_4$-alkyl- or $C_1$–$C_4$-haloalkyl-substituted phenyl ring, a fused carbocycle or a fused, unsubstituted or halogen-, cyano, nitro, $C_1$–$C_4$-alkyl-, di-$C_1$–$C_4$-alkylamino-, $C_1$–$C_4$-alkoxy-, $C_1$–$C_4$-haloalkoxy-, or $C_1$–$C_4$-haloalkyl-substituted second heterocycle forms a bicyclic system;

$R^4$–$R^7$ can be identical or different and independently of one another are hydrogen, alkyl, cycloalkyl, aryl, hydroxyl, alkoxy, cycloalkoxy, aryloxy, thio, alkylthio, cycloalkylthio, arylthio, amino, unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, unsubstituted or substituted mono- or dialkylaminocarbonyl or mono- or diarylaminocarbonyl or N-alkyl-N-arylaminocarbonyl, it being possible for alkyl and aryl to be identical or different, alkoxycarbonylamino, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino, cyano or nitro;

$R^4$–$R^5$ together can form a five- or six-membered saturated or unsaturated aromatic or non-aromatic unsubstituted or substituted alkylene, alkenylene or alkdienylene chain;

$R^8$ is $C_1$–$C_4$-alkyl, $C_1$–$C_4$-haloalkyl, $C_1$–$C_4$-alkoxy, or $NR^9R^{10}$;

$R^9$ is hydrogen or $C_1$–$C_4$-alkyl;

$R^{10}$ $C_1$–$C_4$-alkyl.

Other preferred compounds of the general formula 1 are those where $R^3$ is a radical of the general formula 2a

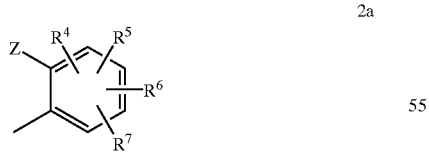

2a where Z and the substituents $R^4$–$R^7$ have the meanings given for the general formula 2 or the following meanings:

Z is a 5- or 6-membered heterocyclic, saturated or unsaturated radical containing one to three hetero atoms selected from the group consisting of oxygen, sulfur or nitrogen and which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, substituted by halogen, cyano, nitro, $C_1$–$C_4$-alkyl or $C_1$–$C_4$-haloalkyl-substituted phenyl or an oxo group—which may, in the tautomeric form also be present as a hydroxyl group—or which together with a fused unsubstituted or halogen-, cyano-, nitro- or $C_1$–$C_4$-alkyl- or $C_1$–$C_4$-haloalkyl-substituted phenyl ring, a fused carbocycle or a fused, unsubstituted or halogen-, cyano-, nitro-, $C_1$–$C_4$-alkyl-, di-$C_1$–$C_4$-alkylamino-, $C_1$–$C_4$-alkoxy-, $C_1$–$C_4$-haloalkoxy-, or $C_1$–$C_4$-haloalkyl-substituted second heterocycle forms a bicyclic system;

$R^4$–$R^7$ can be identical or different and independently of one another are alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkyl carbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, cyano or nitro.

Furthermore, preferred compounds of the general formula 1 are those where $R^3$ is a radical of the general formula 2b

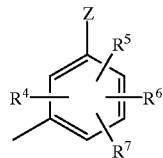

2b where Z and the substituents $R^4$–$R^7$ have the meanings given for the general formula 2 or 2a.

Other preferred compounds of the general formula 1 are those where $R^3$ is a radical of the general formula 2c

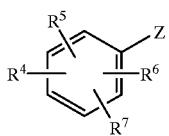

2c where Z and the substituents $R^4$–$R^7$ have the meanings given for the general formula 2 or 2a.

In addition, preferred compounds of the general formula 1 are those where $R^3$ is a radical of the general formula 2,

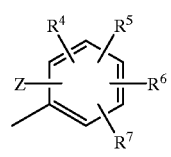

2 or radicals of the general formulae 2a–c

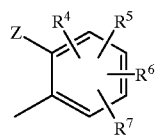

2a

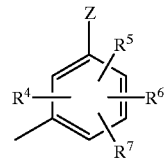

2b

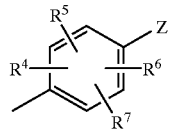

2c where Z has the abovementioned meanings and the substituents $R^4$ to $R^7$ have the following meanings:

$R^4$–$R^7$ can be identical or different and independently of one another are hydrogen, $C_1$–$C_6$-alkyl, preferably methyl, ethyl, propyl, 1-methylethyl, butyl, 2-methylpropyl, pentyl or hexyl; $C_2$–$C_6$-alkenyl, preferably ethenyl, 2-propenyl, 2-butenyl or 3-butenyl; $C_2$–$C_6$-alkynyl, preferably ethynyl, 2-propynyl, 2-butynyl or 3-butynyl; $C_3$–$C_6$-cycloalkyl, preferably cyclopropyl, cyclobutyl, cyclopentyl or cyclohexyl, $C_3$–$C_6$-cycloalkyl-$C_1$–$C_6$-alkyl, $C_3$–$C_6$-cycloalkyl-$C_2$–$C_6$-alkenyl, $C_3$–$C_6$-cycloalkyl-$C_2$–$C_6$-alkynyl, aryl, preferably phenyl or naphthyl, aryl-$C_1$–$C_6$-alkyl, aryl-$C_2$–$C_6$-alkenyl, aryl-$C_2$–$C_6$-alkynyl; hydroxyl, $C_1$–$C_6$-alkoxy, preferably methyloxy, ethyloxy, propyloxy, 1-methylethloxy, butyloxy, pentyloxy or hexyloxy, $C_2$–$C_6$-alkenyloxy, preferably ethenyloxy, 2-propenyloxy, 2-butenyloxy or 3-butenyloxy; $C_2$–$C_6$-alkynyloxy, preferably ethynyloxy, 2-propynyloxy, 2-butynyloxy or 3-butynyloxy; $C_3$–$C_6$-cycloalkoxy, preferably cyclopropyloxy, cyclobutyloxy, cyclopentyloxy or cyclohexyloxy, $C_3$–$C_6$-cycloalkyl-$C_1$–$C_6$-alkoxy, $C_3$–$C_6$-cycloalkyl-$C_2$–$C_6$-alkynyloxy; aryloxy, preferably phenoxy or naphthyloxy, aryl-$C_1$–$C_6$-alkoxy, aryl-$C_2$–$C_6$-alkenyloxy, aryl-$C_2$–$C_6$-alkynyloxy; thio; $C_1$–$C_6$-alkylthio, preferably methylthio, ethylthio, propylthio, 1-methylethylthio, butylthio, pentylthio or hexylthio; $C_2$–$C_6$-alkenylthio, preferably ethenylthio, 2-propenylthio, 2-butenylthio or 3-butenylthio; $C_2$–$C_6$-alkynylthio, preferably ethynylthio, 2-propynylthio, 2-butynylthio or 3-butynylthio; $C_3$–$C_6$-cycloalkylthio, preferably cyclopropylthio, cyclobutylthio, cyclopentylthio or cyclohexylthio, $C_3$–$C_6$-cycloalkyl-$C_1$–$C_6$-alkylthio, $C_3$–$C_6$-cycloalkyl-$C_2$–$C_6$-alkenylthio, $C_3$–$C_6$-cycloalkyl-$C_2$–$C_6$-alkynylthio; arylthio, preferably phenylthio or naphthylthio, aryl-$C_1$–$C_6$-alkylthio, aryl-$C_2$–$C_6$-alkenylthio, aryl-$C_2$–$C_6$-alkynylthio; amino, unsubstituted or substituted mono- or di-$C_1$–$C_6$-alkylamino, unsubstituted or substituted mono- or diarylamino, unsubstituted or substituted N-$C_1$–$C_6$-alkyl-N-arylamino, it being possible for alkyl and aryl to be identical or different; sulfonyl; $C_1$–$C_6$-alkylsulfonyl, preferably methylsulfonyl, ethylsulfonyl, propylsulfonyl, 1-methylethylsulfonyl, butylsulfonyl, 2-methylpropylsulfonyl, pentylsulfonyl or hexylsulfonyl; $C_3$–$C_6$-cycloalkylsulfonyl, preferably cyclopropylsulfonyl, cyclobutylsulfonyl, cyclopentylsulfonyl or cyclohexylsulfonyl, $C_3$–$C_6$-cycloalkyl-$C_1$–$C_6$-alkylsulfonyl, $C_3$–$C_6$-cycloalkyl-$C_2$–$C_6$-alkenylsulfonyl, $C_3$–$C_6$-cycloalkyl-$C_2$–$C_6$-alkynylsulfonyl; arylsulfonyl, preferably phenylsulfonyl or naphthylsulfonyl, aryl-$C_1$–$C_6$-alkylsulfonyl, aryl-$C_2$–$C_6$-alkenylsulfonyl, aryl-$C_2$–$C_6$-alkynylsulfonyl; sulfoxyl and unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, $C_1$–$C_6$-alkylcarbonyl, preferably methylcarbonyl, ethylcarbonyl, propylcarbonyl, 1-methylethylcarbonyl, butylcarbonyl, 2-methylpropylcarbonyl, pentylcarbonyl or hexylcarbonyl; $C_2$–$C_6$-alkenylcarbonyl, preferably ethenylcarbonyl, 2-propenylcarbonyl, 2-butenylcarbonyl or 3-butenylcarbonyl; $C_2$–$C_6$-alkynylcarbonyl, preferably ethynylcarbonyl, 2-propynylcarbonyl, 2-butynylcarbonyl or 3-butynylcarbonyl; $C_3$–$C_6$-cycloalkylcarbonyl, preferably cyclopropylcarbonyl, cyclobutylcarbonyl, cyclopentylcarbonyl or cyclohexylcarbonyl, $C_3$–$C_6$-cycloalkyl-$C_1$–$C_6$-alkylcarbonyl, $C_3$–$C_6$-cycloalkyl-$C_2$–$C_6$-alkenylcarbonyl, $C_3$–$C_6$-cycloalkyl-$C_2$–$C_6$-alkynylcarbonyl; arylcarbonyl, preferably phenylcarbonyl or naphthylcarbonyl, aryl-$C_1$–$C_6$-alkylcarbonyl, aryl-$C_2$–$C_6$-alkenylcarbonyl, aryl-$C_2$–$C_6$-alkynylcarbonyl; carboxyl; $C_1$–$C_6$-alkoxycarbonyl, methyloxycarbonyl, ethyloxycarbonyl, propyloxycarbonyl, 1-methylethyloxycarbonyl, butyloxycarbonyl, pentyloxycarbonyl or hexyloxycarbonyl, $C_2$–$C_6$-alkenyloxycarbonyl, $C_2$–$C_6$-alkynyloxycarbonyl, $C_3$–$C_6$-cycloalkoxycarbonyl, cyclopropyloxycarbonyl, cyclobutyloxycarbonyl, cyclopentyloxycarbonyl or cyclohexyloxycarbonyl, $C_3$–$C_6$-cycloalkyl-$C_1$–$C_6$-alkoxycarbonyl, $C_3$–$C_6$-cycloalkyl-$C_2$–$C_6$-alkenyloxycarbonyl, $C_3$–$C_6$-cycloalkyl-$C_2$–$C_6$-alkynyloxycarbonyl; aryloxycarbonyl, preferably phenyloxycarbonyl or naphthyloxycarbonyl, aryl-$C_1$–$C_6$-alkoxycarbonyl, aryl-$C_2$–$C_6$-alkenyloxycarbonyl, aryl-$C_2$–$C_6$-alkynyloxycarbonyl; aminocarbonyl; unsubstituted or substituted mono- or di-$C_1$–$C_6$-alkylaminocarbonyl, unsubstituted or substituted mono- or diarylaminocarbonyl, unsubstituted or substituted N—$C_1$–$C_6$-alkyl-N-arylaminocarbonyl, it being possible for alkyl and aryl to be identical or different, unsubstituted or substituted mono- or di-$C_1$–$C_6$-alkylcarbonylamino, unsubstituted or substituted mono- or diarylcarbonylamino, unsubstituted or substituted N—$C_1$–$C_6$-alkyl-N-arylcarbonylamino, it being possible for alkyl and aryl to be identical or different, $C_1$–$C_6$-alkoxyaminocarbonyl, preferably methyloxyaminocarbonyl, ethyloxyaminocarbonyl, propyloxyaminocarbonyl, 1-methylethyloxyaminocarbonyl, butyloxyaminocarbonyl, 2-methylpropyloxyaminocarbonyl, pentyloxyaminocarbonyl or hexyloxyaminocarbonyl; $C_2$–$C_6$-alkenyloxycarbonylamino, preferably ethylenoxyaminocarbonyl, 2-propenyloxyaminocarbonyl, 2-butenyloxyaminocarbonyl or 3-butenyloxyaminocarbonyl; $C_2$–$C_6$-alkynyloxycarbonylamino, preferably ethynyloxyaminocarbonyl, 2-propynyloxyaminocarbonyl, 2-butynyloxyaminocarbonyl or 3-butynyloxyaminocarbonyl; $C_3$–$C_6$-cycloalkoxyaminocarbonyl, preferably cyclopropyloxyaminocarbonyl, cyclobutyloxyaminocarbonyl, cyclopentyloxyaminocarbonyl or cyclohexyloxyaminocarbonyl, $C_3$–$C_6$-cycloalkyl-$C_1$–$C_6$-alkoxyaminocarbonyl, $C_3$–$C_6$-cycloalkyl-$C_2$–$C_6$-alkenyloxyaminocarbonyl, $C_3$–$C_6$-cycloalkyl-$C_1$–$C_6$-alkynyloxyaminocarbonyl; aryloxyaminocarbonyl, preferably phenyloxyaminocarbonyl or naphthyloxyaminocarbonyl, aryl-$C_1$–$C_6$-alkoxyaminocarbonylamino, aryl-$C_2$–$C_6$-alkenyloxyaminocarbonyl, aryl-$C_2$–$C_6$-alkynyloxyaminocarbonyl; halogen, preferably fluorine, chlorine, brom or iodine; $C_1$–$C_6$-haloalky, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_2$–$C_6$-haloalkenyl, $C_2$–$C_6$-haloalkynyl; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy, $C_2$–$C_6$-haloalkenyloxy, $C_2$–$C_6$-haloalkynyloxy; $C_1$–$C_6$-haloalkylthio, preferably chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, $C_2$–$C_6$-haloalkenylthio, $C_2$–$C_6$-haloalkynylthio; $C_1$–$C_6$-haloalkylamino, preferably chloromethylamino, dichloromethylamino, trichloromethylamino, fluoromethylamino, difluoromethylamino, trifluoromethylamino, chlorofluoromethylamino, dichlorofluoromethylamino, chlorodifluoromethylamino, 1-fluoroethylamino, 2-fluoroethylamino, 2,2-difluoroethylamino, 2,2,2-trifluoroethylamino, 2-chloro-2-fluoroethyl-amino, 2-chloro-2,2-difluoroethylamino, 2,2-dichloro-2-fluoroethylamino, 2,2,2-trichloroethylamino or pentafluoroethylamino, $C_2$–$C_6$-haloalkenylamino, $C_2$–$C_6$-haloalkynylamino, $C_1$–$C_6$-haloalkylsulfonyl, preferably chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethylsulfonyl, 2,2-di-fluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or pentafluoroethylsulfonyl, $C_2$–$C_6$-haloalkenylsulfonyl, $C_2$–$C_6$-haloalkynylsulfonyl; $C_1$–$C_6$-haloalkylcarbonyl, preferably chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoro-ethylcarbonyl, 2-2-2-trichloroethylcarbonyl or pentafluoroethylcarbonyl, $C_2$–$C_6$-haloalkenylcarbonyl, $C_2$–$C_6$-haloalkynylcarbonyl; $C_1$–$C_6$-haloalkoxycarbonyl, preferably chloromethyloxycarbonyl, dichloromethyloxycarbonyl, trichloromethyloxycarbonyl, fluoromethyloxycarbonyl, difluoromethyloxycarbonyl, trifluoromethyloxycarbonyl, chlorofluoromethyloxycarbonyl, dichlorofluoromethyloxycarbonyl, chlorodifluoromethyloxycarbonyl, 1-fluoroethyloxycarbonyl, 2-fluoroethyloxycarbonyl, 2,2-difluoroethyloxycarbonyl, 2,2,2-trifluoroethyloxycarbonyl, 2-chloro-2-fluoroethyloxycarbonyl, 2-chloro-2,2-difluoroethyloxycarbonyl, 2,2-dichloro-2-fluoroethyloxycarbonyl, 2,2,2-trichloroethyloxycarbonyl or pentafluoroethyloxycarbonyl, $C_2$–$C_6$-haloalkenyloxycarbonyl, $C_2$–$C_6$-haloalkynyloxycarbonyl; $C_1$–$C_6$-haloalkylaminocarbonyl, preferably chloromethylaminocarbonyl, dichloromethylaminocarbonyl, trichloromethylaminocarbonyl, fluormethylaminocarbonyl, difluoromethylaminocarbonyl, trifluoromethylaminocarbonyl, chlorofluoromethylaminocarbonyl, dichlorofluoromethylaminocarbonyl, chlorodifluoromethylaminocarbonyl, 1-fluoroethylaminocarbonyl, 2-fluoroethylaminocarbonyl, 2,2-difluoroethylaminocarbonyl, 2,2,2-trifluoroethylaminocarbonyl, 2-chloro-2-fluoroethylaminocarbonyl, 2-chloro-2,2-difluoroethylaminocarbonyl, 2,2-dichloro-2-fluoroethylaminocarbonyl, 2,2,2-trichloroethylaminocarbonyl or pentafluoroethylaminocarbonyl, $C_2$–$C_6$-haloalkenylaminocarbonyl, $C_2$–$C_6$-haloalkynylaminocarbonyl; $C_1$–$C_6$-haloalkoxycarbonylamino, chloromethyloxyaminocarbonyl, dichloromethyloxycarbonyl, trichloromethyloxyaminocarbonyl, fluoromethyloxyaminocarbonyl, difluoromethyloxyaminocarbonyl, trifluoromethyloxyaminocarbonyl, chlorofluoromethyloxyaminocarbonyl, dichlorofluoromethyloxyaminocarbonyl, chlorodifluoromethyloxyaminocarbonyl, 1-fluoroethyloxyaminocarbonyl, 2-fluoroethyloxyaminocarbonyl, 2,2-difluoroethyloxyaminocarbonyl, 2,2,2-trifluoroethyloxyaminocarbonyl, 2-chloro-2-fluoroethyloxyaminocarbonyl, 2-chloro-2,2-difluoroethyloxyaminocarbonyl, 2,2-dichloro-2-fluoroethyloxyaminocarbonyl, 2,2,2-trichloroethyloxyaminocarbonyl or pentafluoroethyloxyaminocarbonyl, $C_2$–$C_6$-haloalkenyloxycarbonylamino, $C_2$–$C_6$-haloalkynyloxycarbonylamino, cyano or nitro.

In addition, especially preferred compounds of the general formula 1 are those where $R^3$ is a radical of the general formula 2d

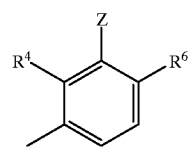

2d where $R^4$ and $R^6$ are identical or different and independently of one another are alkyl, preferably methyl or ethyl, alkylsulfonyl, preferably methylsulfonyl or ethylsulfonyl; halogen, preferably fluorine, chlorine or bromine, haloalkyl, preferably difluoromethyl, trifluoromethyl, tetrafluoroethyl or trichloromethyl.

Other preferred compounds of the general formula 1 are those where $R^3$ is a radical of the general formula 2e

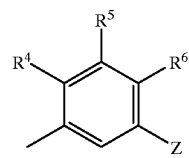

2e and $R^4$, $R^5$ and $R^6$ are identical or different and independently of one another are alkyl, preferably methyl or ethyl, alkoxy, prefeably methoxy, ethoxy, or aryloxy, preferably phenoxy; alkylsulfonyl, preferably methylsulfonyl or ethylsulfonyl; halogen, preferably fluorine, chlorine, bromine or iodine; haloalkyl, preferably difluoromethyl, trifluoromethyl, tetrafluoroethyl oder trichloromethyl.

Other preferred compounds of the general formula 1 are those where the substituents are selected from a combination of the preferred substituents listed above.

4-Benzoylisothiazoles of the general formula 1 are acceptable a) by reacting the haloisothiazole compounds 3

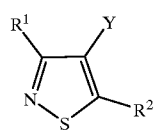

3 where $R^1$ and $R^2$ have the above-described meanings and Y is halogen, preferably chlorine, bromine or iodine, with element magnesium or an organomagnesium or organolithium compound and with a carboxylic acid derivative of the general formula 4

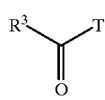

where $R^3$ has the above-described meanings and T is halogen, preferably chlorine, bromine or iodine, or N-alkoxy-N-alkylamino, preferably N-methoxy-N-methylamino, or cyano in a temperature range of from −78° C. to 111° C., preferably in a temperature range of from −20° C. to 111° C., in the presence of an inert solvent (A. Alberola, F. Alonso, P. Cuadrado, M. C. Sanudo, Synth. Commun. 17 (1987)1207), or b. by reacting a halobenzene of the general formula 5

where $R^3$ has the above-described meanings and Y is halogen, preferably chlorine, bromine or iodine, with elemental magnesium or an organomagnesium or organolithium compound and with an isothiazole carboxylic acid derivative of the general formula 6a or 6b,

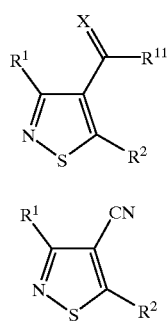

where X, $R^1$ and $R^2$ have the above-described meanings and $R^{11}$ is halogen, preferably chlorine, bromine or iodine, and N-alkoxy-N-alkylamino, preferably N-methoxy-N-methylamino, in a temperature range of from −78° C. to 111° C., preferably in a temperature range of from −20° C. to 111° C., in the presence of an inert solvent (A. Alberola, F. Alonso, P. Cuadrado, M. C. Sanudo, J. Heterocyclic Chem. 25 (1988) 235).

The haloisothiazole compounds 3 are synthesized by halogenating isothiazole compounds of the general formula 7

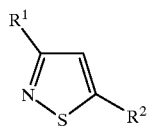

where $R^1$ and $R^2$ have the above-described meanings, by processes known from the literature (of which the following representatives may be mentioned: a. A. Alberola, F. Alonso, P. Cuadrado, M. C. Sanudo, Synth. Commun. 17 (1987) 1207; b. Vasilevskii, Izv. Akad. Nauk. SSSR Ser. Khim. (1975) 616)

Isothiazole compounds of the general formula 7 are known in principle and are synthesized by methods known from the literature (of which the following representatives may be mentioned: a. D. N McGregor. U. Corbin, J. E. Swigor, I. C. Cheney, Tetrahedron 25 (1968) 389; b. F. Lucchesini, N. Picci. M. Pocci., Heterocycles 29 (1989) 97).

The isothiazole carboxylic acid derivatives of the general formula 6b are synthesized by reacting the haloisothiazole compounds 3 with inorganic cyanides, for example copper (I) cyanide, by processes known from the literature (of which the following representatives may be mentioned: A. Alberola, F. Alonso, P Cuadrado, M. C. Sanudo, J. Heterocyclic Chem. 25 (1988) 235). The corresponding isothiazolecarboxylic acid derivatives of the general formula 6a can be synthesized starting from isothiazolecarboxylic acid derivatives of the general formula 6b by methods known from the literature.

Preferred organomagnesium compounds are alkylmagnesium halides, for example methyl- or ethylmagnesium bromide or methyl- or ethylmagnesium chloride. Suitable organolithium compounds are, preferably, aliphatic lithium compounds such as lithium diisopropylamide, n-butyllithium or secondary butyllithium.

The organic solvent selected depends on the starting materials employed. In general, any inert solvent is suitable. Preferred inert solvents are aliphatic, cyclic or acyclic ethers, for example diethyl ether, tetrahydrofuran, dioxane or 1,2-dimethoxyethane. In addition, inert aromatic solvents such as benzene and toluene are also used.

The starting materials are normally reacted with each other in stoichiometric amounts. However, it may be advantageous to employ an excess of one of the starting materials of 0.1 to 10 mol equivalents, for example to improve the yield.

Benzoic acid derivatives of the formula 4 can be prepared as follows:

Benzoyl halides, for example benzoyl chlorides of the formula 4 (T=Cl) are prepared in a known manner by reacting the benzoic acids of the formula 4 (T=OH) with thionyl chloride.

The benzoic acids of the formula 4 (T=OH) can be prepared in a known manner from the corresponding esters of the formula 4 (T=$C_1$-$C_4$-alkoxy) by means of acidic or basic hydrolysis.

The intermediates of the formula 4 can be synthesized for example as shown in schemata 1 and 2 via the routes described herein below.

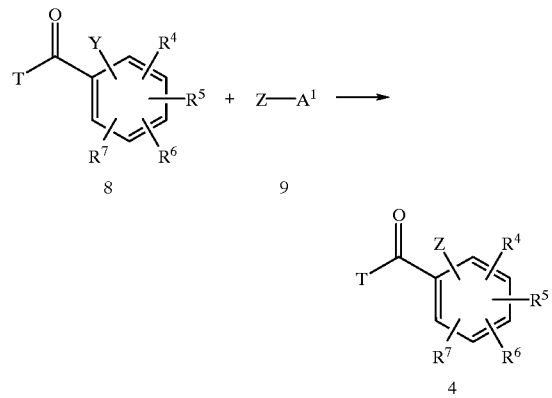

T is $C_1$-$C_4$-alkoxy,
Y is Cl, Br, I, —OS(O)$_2$CF$_3$, —OS(O)$_2$F
$A^1$ is Sn($C_1$-$C_4$-alkyl)$_3$, B(OH)$_2$, ZnHal, Hal being Cl or Br and Z the substituents $R^4$, $R^5$, $R^6$ and $R^7$ are as defined above.

According to this scheme, the arylhalogen compounds or arylsulfonates 8 can be reacted in a known manner with heteroaryl stannanes (Stille couplings), heteroaryl boron compounds (Suzuki couplings) or heteroaryl zinc compounds (Negishi reaction) V (cf., for example, Synthesis 1987, 51–53, Synthesis 1992, 413) in the presence of a palladium or nickel transition-metal catalyst and in the presence or absence of a base to give the novel compounds of the general formula 4.

The benzoic acid derivatives of the formula 4a can also be obtained by reacting corresponding bromine- or iodine-substituted compounds of the formula 10

Scheme 2

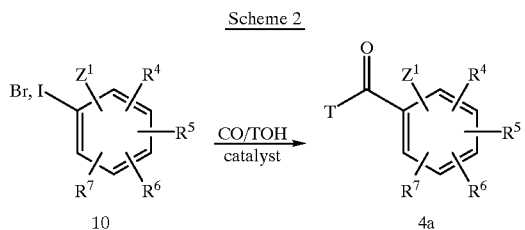

$Z^1$ is Z or CN and

T is OH or $C_1$–$C_4$-alkoxy and the substituents $R^4$, $R^5$, $R^6$ and $R^7$ have the abovementioned meanings with carbon monoxide and water under elevated pressure in the presence of a palladium, nickel, cobalt or rhodium transition-metal catalyst.

The catalysts nickel, cobalt, rhodium and, in particular, palladium can exist in the known valency states in the form of metals or in the form of customary salts, such as in the form of halogen compounds, for example $PdCl_2$, $RhCl_3.H_2O$, acetates, for example $Pd(OAc)_2$, cyanides, etc. There may furthermore exist metal complexes with tertiary phosphines, metal alkylcarbonyls, metal carbonyls, for example $CO_2(CO)_8$, $Ni(CO)_4$, metal carbonyl complexes with tertiary phosphines, for example $(PPh_3)_2Ni(CO)_2$, or transition-metal salts complexed with tertiary phosphines. The last-mentioned embodiment is preferred especially when palladium is used as the catalyst. The nature of the phosphine ligands can vary in a broad range. For example, it can be represented by the following formulae:

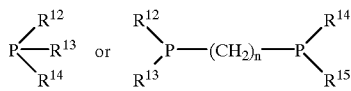

where n is a number 1, 2, 3 or 4 and the radicals $R^{12}$ to $R^{15}$ are lower alkyl, for example $C_1$–$C_6$-alkyl, aryl, $C_1$–$C_4$-alkylaryl, for example benzyl, phenethyl or aryloxy. Aryl is, for example naphthyl, anthryl and, preferably, unsubstituted or substituted phenyl; with respect to the substituents, care is to be taken that they are inert to the carboxylation reaction, apart from this they can be varied in a broad range and embrace all inert C-organic radicals, such as $C_1$–$C_6$-alkyl radicals, for example methyl, carboxyl radicals such as COOH, COOM (M is for example, an alkali metal, alkaline earth metal or ammonium salt), or C-organic radicals bonded by oxygen, such as $C_1$–$C_6$-alkoxy radicals.

The phosphine complexes can be prepared in a known manner, for example as described in the documents mentioned at the outset. For example, customary commercially available metal salts such as $PdCl_2$ or $Pd(OCOCH_3)_2$ are used as starting materials, and the phosphine, for example $P(C_6H_5)_3$, $P(n-C_4H_9)_3$, $PCH_3(C_6H_5)_2$, 1,2-bis (diphenylphosphino)ethane is added.

The amount of phosphine based on the transition metal is normally from 0 to 20, in particular from 0.1 to 10, mol equivalents, particularly preferably from 1 to 5 mol equivalents.

The amount of transition metal is not critical. Naturally, a small amount, for example from 0.1 to 10 mol %, in particular from 1 to 5 mol %, based on the starting material of the formula 4, will be used for reasons of economy.

To prepare the benzoic acids 4 (T=OH), the reaction is carried out with carbon monoxide and at least equimolar amounts of water based on the starting materials 10. The reactant water can simultaneously also act as the solvent, i.e. the maximum amount is not critical.

Depending on the nature of the starting material and the catalyst used, however, it may also be advantageous to use, as the solvent, the base used for the carboxylation or a different inert solvent, instead of the reactant.

Suitable inert solvents are those customary for carboxylation reactions, such as hydrocarbons for example toluene, xylene, hexane, pentane, cyclohexane, ethers, for example methyl tert-butyl ether, tetrahydrofuran, dioxane, dimethoxyethane, substituted amides such as dimethylformamide, persubstituted ureas such as tetra-$C_1$–$C_4$-alkylureas, or nitriles such as benzonitrile or acetonitrile.

In a preferred embodiment of the process, one of the reactants, in particular the base, is used in an excess, thus dispensing with additional solvents.

Bases which are suitable for the process are all inert bases which are capable of binding the hydrogen iodide or hydrogen bromide which is released during the reaction. Examples are tertiary amines such as tert-alkylamines, for example trialkylamines such as triethylamine, cyclic amines such as N-methylpiperidine or N,N'-dimethylpiperazine, pyridine, alkali metal carbonates or alkali metal hydrogen carbonates, or tetraalkyl-substituted urea derivatives such as tetra-$C_1$–$C_4$-alkylurea, e.g. tetramethylurea.

The amount of base is not critical, from 1 to 10, in particular from 1 to 5 mol, normally being used. When simultaneously using the base as the solvent, the amount is, as a rule, proportioned so that the reactants are dissolved, but unnecessarily high excesses are avoided for practical reasons, to save costs, to be able to use small reaction vessels, and to guarantee maximum contact between the reactants.

During the reaction, the carbon monoxide pressure is adjusted so that there is always an excess of CO present, based on the compound of the formula 10. The carbon monoxide pressure is preferably 1 to 250 bar, at room temperature, in particular 5 to 150 bar CO.

As a rule, the carbonylation is carried out at from 20 to 250° C., in particular at from 30 to 150° C., either continuously or batchwise. In the case of batchwise operation, it is expedient to inject carbon monoxide continuously onto the reaction mixture in order to maintain a constant pressure.

Those arylhalogen compounds of the formula 10 used as starting compounds which are not already known can be prepared in a simple manner by means of a suitable combination of known syntheses.

For example, the halogen compounds 10 can be obtained by subjecting corresponding anilins to a Sandmeyer reaction, and these anilins, in turn, are synthesized by reducing suitable nitro compounds (cf., for example, for compound 10 where $Z^1$=CN: Liebigs Ann. Chem. 1980, 768–778). The aryl bromides 10 can furthermore be obtained by directly brominating suitable starting materials [cf., for example, Monatsh. Chem. 99, (1968) 815–822].

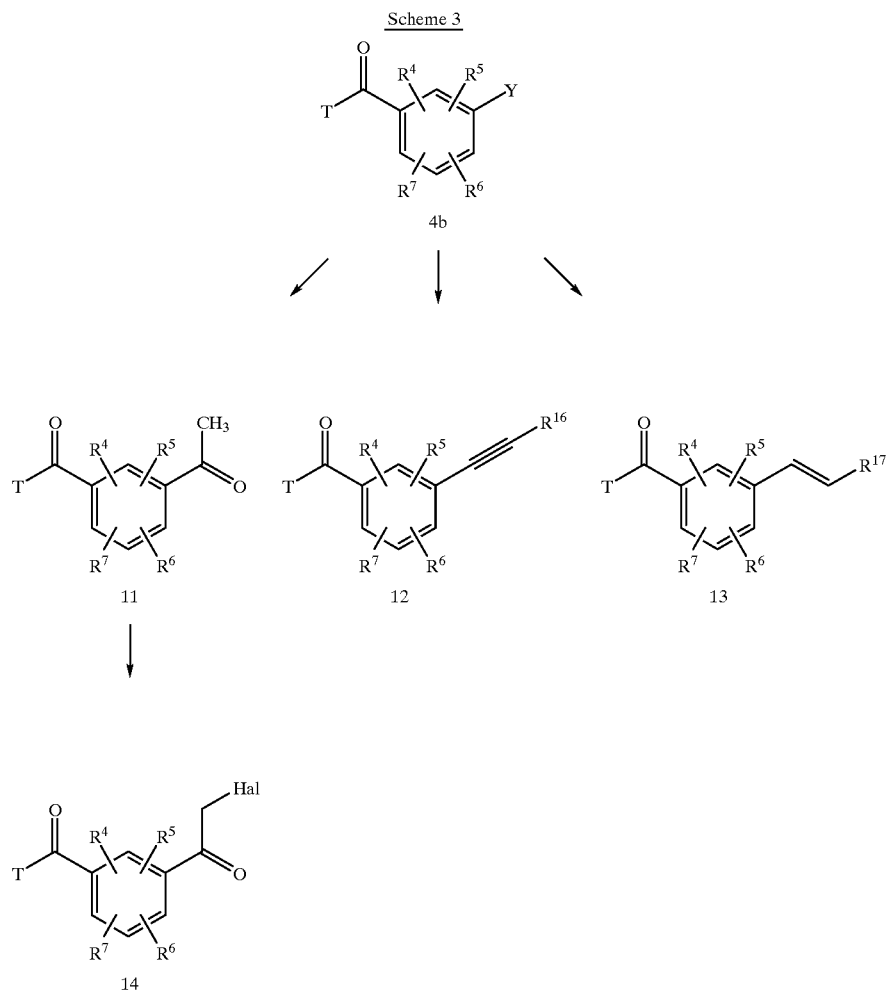

Scheme 3

T is $C_1$–$C_4$-alkoxy,

Y is Cl, Br, I, —OS(O)$_2$CF$_3$, —OS(O)$_2$F,

Z and $R^4$–$R^7$ are as defined above, $R^{16}$ is hydrogen, $C_1$–$C_4$-alkyl, $C_1$–$C_4$-haloalkyl, $C_3$–$C_8$-cycloalkyl, unsubstituted or substituted phenyl or trimethylsilyl, and $R^{17}$ is hydrogen, $C_1$–$C_4$-haloalkyl, $C_3$–$C_8$-cycloalkyl or unsubstituted or substituted phenyl.

Starting from the arylhalogen compounds or arylsulfonates 8, aryl methyl ketones 11 can be prepared by reacting the starting materials arylhalogen compounds or arylsulfonates 8 with vinyl alkyl ethers by processes known from the literature in the presence of a palladium- or nickel transition-metal catalyst and in the presence or absence of a base, followed by hydrolysis [cf. for example, Tetrahedron Lett. 32, (1991), 1753–1756].

The ethynylated aromatics 12 can be prepared in a known manner by reacting arylhalogen compounds or arylsulfonates 8 with substituted acetylenes in the presence of a palladium or nickel transition-metal catalyst (for example heterocycles 24 (1986), 31–32). Derivatives 12 where $R^{16}$=H are expediently obtained from the silyl compounds 12, $R^{16}$=—Si(CH$_3$)$_3$ [J.Org.Chem. 46, (1981), 2280–2286].

Subjecting arylhalogen compounds or arylsulfonates 4b to a Heck reaction with olefins in the presence of a palladium catalyst gives the arylalkenes 13 (cf., for example, Heck, Palladium Reagents in Organic Synthesis, Academic Press, London 1985 and Synthesis 1993, 735–762).

Those benzoyl derivatives 4b used as starting materials which are not already known (cf., for example, Coll. Czech. Chem. Commn. 40, (1975), 3009–3019 (1975)] can be prepared in a simple manner by a suitable combination of known syntheses.

For example, the sulfonates 4b (Y=—OS(O)$_2$CF$_3$, —OS(O)$_2$F) can be obtained from the corresponding phenols; those which are not already known (cf., for example, EP 195247) can be prepared by known methods (cf., for example, Synthesis 1993, 735–762).

The halogen compounds 4b (Y=Cl, Br or I) can be obtained for example by subjecting corresponding anilins to a Sandmeyer reaction.

Scheme 4

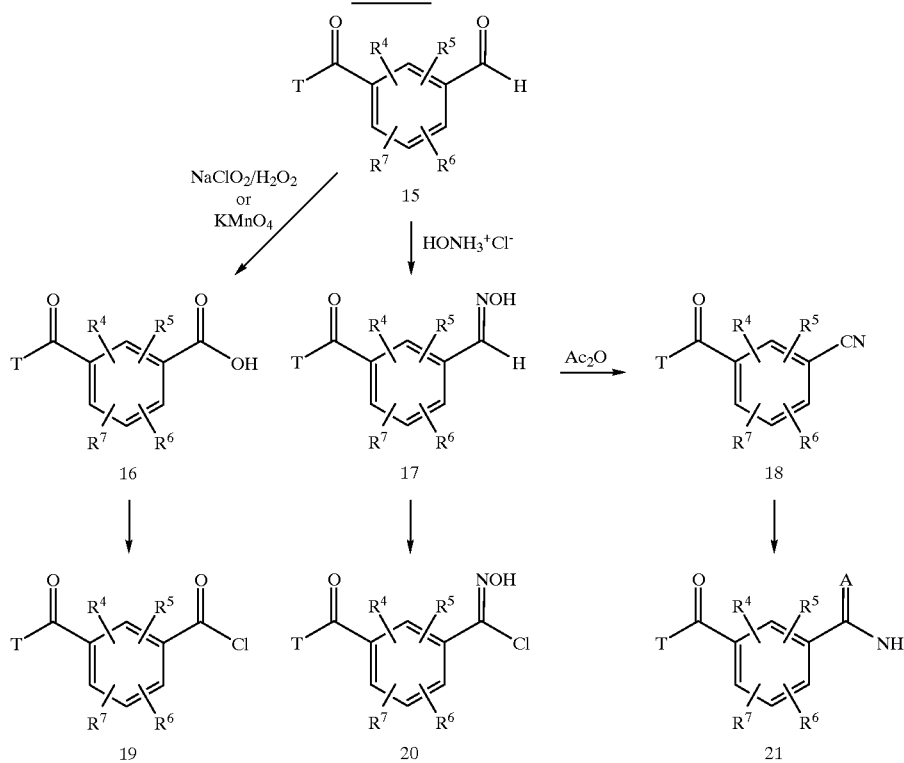

A is S, NH or NOH and

T is $C_1$–$C_4$-alkoxy and the substituents $R^4$–$R^7$ are as defined above.

Isophthalic acid derivatives 16 can be prepared from the aldehydes 15 by known methods [see J. March Advanced Organic Chemistry 3rd Edition (1985), pp. 629 et seq., Wiley-Interscience Publication].

The oximes 17 are advantageously obtained by reacting aldehydes 15 with hydroxylamine in a known manner [see J. March Advanced Organic Chemistry (1985), 3rd Edition, pp. 805–806, Wiley-Interscience Publication].

The oximes 17 can be converted into nitriles 18 by processes which are also known (see J. March Advanced Organic Chemistry (1985), 3rd Edition, pp. 931–932, Wiley-Interscience Publication].

Those aldehydes 15 required as starting materials which are not already known can be prepared by known methods. For example, they can be synthesized from the methyl compounds 22 as shown in Schema 5.

Scheme 5

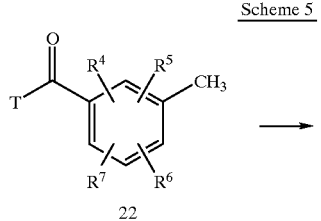

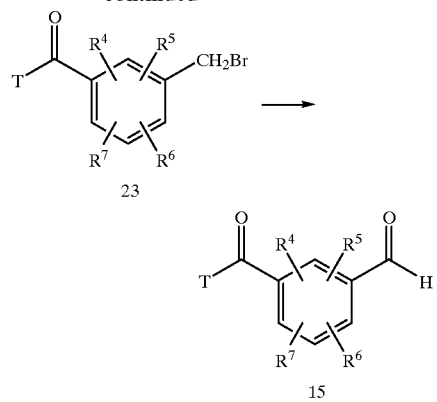

The radicals T and $R^4$, $R^5$, $R^6$ and $R^7$ have the meanings mentioned in Schema 4. The methyl compounds 22 can be reacted to give the benzyl bromides 23 by generally known methods, for example with N-bromosuccinimide or 1,3-dibromo-5,5-dimethylhydantoin. The reaction of benzyl bromides to give benzaldehydes 15 is also known from the literature [cf. Synth. Commun. 22 (1992), 1967–1971].

The precursors 11 to 18 are suitable for synthesizing heterocyclic intermediates 4.

For example, 5-oxazolyl [cf., for example, J. Heterocyclic Chem., 28, (1991), 17–28] or 4-thiazolyl derivatives [cf., for example, Metzger, thiazoles in: The Chemistry of Heterocyclic Compounds, (1976), Vol.34 p. 175 et seq.] can be obtained from the acetophenones 11 via the halogenated intermediate 14.

The acetylenes 12 and the alkenes 13 are suitable for synthesizing 4-isoxazolyl, 5-isoxazolyl, 4,5- dihydroisoxazol-4-yl, 4,5-dihydroisoxazol-5-yl derivatives [cf., for example, Houben-Weyl, Methoden der organischen Chemie, (Methods in Organic Chemistry), 4th Edition (1965), Vol. X/3, p. 843 et seq.].

Following processes known from the literature, the benzoic acids 16 and the acid chlorides 19 which can be obtained from them by standard methods can, for example, be used for preparing 2-oxazolyl-, 1,2,4-oxadiazol-5-yl- and 1,3,4-oxadiazol-2-yl derivatives [cf., for example, J. Heterocyclic Chem., 28, (1991) 17–28] or 2-pyrrolyl derivatives [cf., for example, Heterocycles 26, (1987) 3141–3151].

1,2,4-Triazol-3-yl derivatives can be prepared from benzonitriles 18 by known methods [cf., for example, J. Chem. Soc. (1954), 3461–3464].

The benzonitriles 18 can be converted into 1,2,4-oxadiazol-3-yl [cf., for example, J. Heterocyclic Chem., 28 (1991), 17–28], 2-thiazolyl, 4,5-dihydrothiazol-2-yl or 5,6-dihydro-4H-1,3-thiazine-2-yl derivatives [cf., for example, Houben-Weyl, Methoden der organischen Chemie (Methods in Organic Chemistry), 4th Edition (1985), Vol. E5, p. 1268 et seq.] via the thioamide, amidoxime or amidine intermediate 21. Following processes known from the literature, 1,2,4-thiadiazol-5-yl derivatives (cf., for example, J.Org.Chem. 45 (1980), 3750–3753] or 1,3,4-thiadiazol-2-yl derivatives [cf., for example, J. Chem.Soc., Perkin Trans. I (1982), 1987–1991] may also be obtained from the thioamides 21 (A=S).

The conversion of oximes 17 into 3-isoxazolyl derivatives can be effected in a known manner via the intermediate hydroxamoyl chloride 20 [cf., for example, Houben-Weyl, Methoden der organischen Chemie (Methods in Organic Chemistry), 4th Edition (1965), Vol. X/3, p. 843 et seq.].

Examples of especially preferred compounds of the general formula 1 are compiled in the table which follows. The definitions of the radicals are not only especially preferred in the specific combination of radicals, but also in each case when considered on their own.

TABLE 1

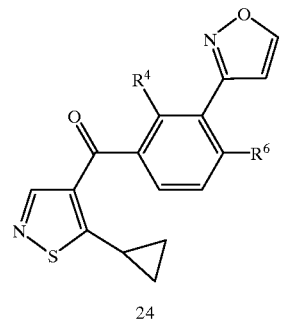

24

| No. | $R^4$ | $R^6$ |
|---|---|---|
| 24.1 | Cl | F |
| 24.2 | Cl | Cl |
| 24.3 | Cl | Br |
| 24.4 | Cl | $CH_3$ |
| 24.5 | Cl | $C_2H_5$ |
| 24.6 | Cl | $nC_3H_7$ |
| 24.7 | Cl | $iC_3H_7$ |
| 24.8 | Cl | $nC_4H_9$ |
| 24.9 | Cl | $tC_4H_9$ |
| 24.10 | Cl | Ph |
| 24.11 | Cl | OH |
| 24.12 | Cl | $OCH_3$ |
| 24.13 | Cl | $OC_2H_5$ |
| 24.14 | Cl | $O(nC_3H_7)$ |

TABLE 1-continued

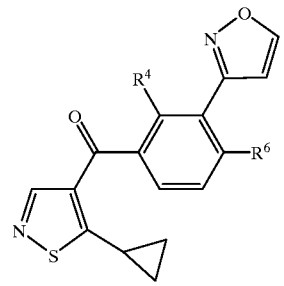

24

| No. | $R^4$ | $R^6$ |
|---|---|---|
| 24.15 | Cl | $O(iC_3H_7)$ |
| 24.16 | Cl | $O(nC_4H_9)$ |
| 24.17 | Cl | $O(tC_4H_9)$ |
| 24.18 | Cl | OPh |
| 24.19 | Cl | SH |
| 24.20 | Cl | $SCH_3$ |
| 24.21 | Cl | $SC_2H_5$ |
| 24.22 | Cl | $S(nC_3H_7)$ |
| 24.23 | Cl | $S(iC_3H_7)$ |
| 24.24 | Cl | $S(nC_4H_9)$ |
| 24.25 | Cl | $S(tC_4H_9)$ |
| 24.26 | Cl | SPh |
| 24.27 | Cl | $CCl_3$ |
| 24.28 | Cl | $CH_2F$ |
| 24.29 | Cl | $CHF_2$ |
| 24.30 | Cl | $CF_3$ |
| 24.31 | Cl | $CF_2CHF_2$ |
| 24.32 | Cl | $SO_3H$ |
| 24.33 | Cl | $SO_2CH_3$ |
| 24.34 | Cl | $SO_2C_2H_5$ |
| 24.35 | Cl | $SO_2(nC_3H_7)$ |
| 24.36 | Cl | $SO_2(iC_3H_7)$ |
| 24.37 | Cl | $SO_2(nC_4H_9)$ |
| 24.38 | Cl | $SO_2(tC_4H_9)$ |
| 24.39 | Cl | $SO_2Ph$ |
| 24.40 | Cl | $NH_2$ |
| 24.41 | Cl | $NHCH_3$ |
| 24.42 | Cl | $NCH_3Ph$ |
| 24.43 | Cl | $N(CH_3)_2$ |
| 24.44 | Cl | $NPh_2$ |
| 24.45 | Cl | CN |
| 24.46 | Cl | $NO_2$ |
| 24.47 | $CH_3$ | F |
| 24.48 | $CH_3$ | Cl |
| 24.49 | $CH_3$ | Br |
| 24.50 | $CH_3$ | $CH_3$ |
| 24.51 | $CH_3$ | $C_2H_5$ |
| 24.53 | $CH_3$ | $nC_3H_7$ |
| 24.54 | $CH_3$ | $iC_3H_7$ |
| 24.55 | $CH_3$ | $nC_4H_9$ |
| 24.56 | $CH_3$ | $tC_4H_9$ |
| 24.57 | $CH_3$ | Ph |
| 24.58 | $CH_3$ | OH |
| 24.59 | $CH_3$ | $OCH_3$ |
| 24.60 | $CH_3$ | $OC_2H_5$ |
| 24.61 | $CH_3$ | $O(nC_3H_7)$ |
| 24.62 | $CH_3$ | $O(iC_3H_7)$ |
| 24.63 | $CH_3$ | $O(nC_4H_9)$ |
| 24.64 | $CH_3$ | $O(tC_4H_9)$ |
| 24.65 | $CH_3$ | OPh |
| 24.66 | $CH_3$ | SH |
| 24.67 | $CH_3$ | $SCH_3$ |
| 24.68 | $CH_3$ | $SC_2H_5$ |
| 24.69 | $CH_3$ | $S(nC_3H_7)$ |
| 24.70 | $CH_3$ | $S(iC_3H_7)$ |
| 24.71 | $CH_3$ | $S(nC_4H_9)$ |
| 24.72 | $CH_3$ | $S(tC_4H_9)$ |
| 24.73 | $CH_3$ | SPh |
| 24.74 | $CH_3$ | $CCl_3$ |
| 24.75 | $CH_3$ | $CH_2F$ |

TABLE 1-continued

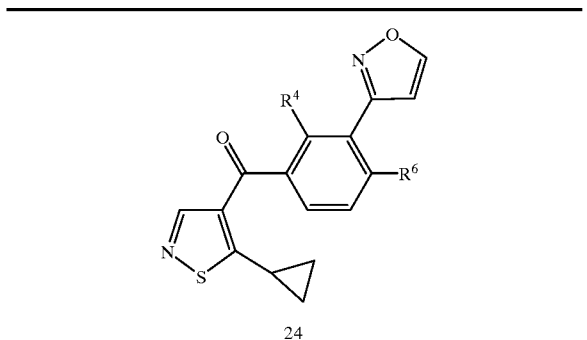

24

| No. | R⁴ | R⁶ |
|---|---|---|
| 24.76 | $CH_3$ | $CHF_2$ |
| 24.77 | $CH_3$ | $CF_3$ |
| 24.78 | $CH_3$ | $CF_2CHF_2$ |
| 24.79 | $CH_3$ | $SO_3H$ |
| 24.80 | $CH_3$ | $SO_2CH_3$ |
| 24.81 | $CH_3$ | $SO_2C_2H_5$ |
| 24.82 | $CH_3$ | $SO_2(nC_3H_7)$ |
| 24.83 | $CH_3$ | $SO_2(iC_3H_7)$ |
| 24.84 | $CH_3$ | $SO_2(nC_4H_9)$ |
| 24.85 | $CH_3$ | $SO_2(tC_4H_9)$ |
| 24.86 | $CH_3$ | $SO_2Ph$ |
| 24.87 | $CH_3$ | $NH_2$ |
| 24.88 | $CH_3$ | $NHCH_3$ |
| 24.89 | $CH_3$ | $NCH_3Ph$ |
| 24.90 | $CH_3$ | $N(CH_3)_2$ |
| 24.91 | $CH_3$ | $NPh_2$ |
| 24.92 | $CH_3$ | $CN$ |
| 24.93 | $CH_3$ | $NO_2$ |
| 24.94 | $SO_2CH_3$ | F |
| 24.95 | $SO_2CH_3$ | Cl |
| 24.96 | $SO_2CH_3$ | Br |
| 24.97 | $SO_2CH_3$ | $CH_3$ |
| 24.98 | $SO_2CH_3$ | $C_2H_5$ |
| 24.99 | $SO_2CH_3$ | $nC_3H_7$ |
| 24.100 | $SO_2CH_3$ | $iC_3H_7$ |
| 24.101 | $SO_2CH_3$ | $nC_4H_9$ |
| 24.102 | $SO_2CH_3$ | $tC_4H_9$ |
| 24.103 | $SO_2CH_3$ | Ph |
| 24.104 | $SO_2CH_3$ | OH |
| 24.105 | $SO_2CH_3$ | $OCH_3$ |
| 24.106 | $SO_2CH_3$ | $OC_2H_5$ |
| 24.107 | $SO_2CH_3$ | $O(nC_3H_7)$ |
| 24.108 | $SO_2CH_3$ | $O(iC_3H_7)$ |
| 24.109 | $SO_2CH_3$ | $O(nC_4H_9)$ |
| 24.110 | $SO_2CH_3$ | $O(tC_4H_9)$ |
| 24.111 | $SO_2CH_3$ | OPh |
| 24.112 | $SO_2CH_3$ | SH |
| 24.113 | $SO_2CH_3$ | $SCH_3$ |
| 24.114 | $SO_2CH_3$ | $SC_2H_5$ |
| 24.115 | $SO_2CH_3$ | $S(nC_3H_7)$ |
| 24.116 | $SO_2CH_3$ | $S(iC_3H_7)$ |
| 24.117 | $SO_2CH_3$ | $S(nC_4H_9)$ |
| 24.118 | $SO_2CH_3$ | $S(tC_4H_9)$ |
| 24.119 | $SO_2CH_3$ | SPh |
| 24.120 | $SO_2CH_3$ | $CCl_3$ |
| 24.121 | $SO_2CH_3$ | $CH_2F$ |
| 24.122 | $SO_2CH_3$ | $CHF_2$ |
| 24.123 | $SO_2CH_3$ | $CF_3$ |
| 24.124 | $SO_2CH_3$ | $CF_2CHF_2$ |
| 24.125 | $SO_2CH_3$ | $SO_3H$ |
| 24.126 | $SO_2CH_3$ | $SO_2CH_3$ |
| 24.127 | $SO_2CH_3$ | $SO_2C_2H_5$ |
| 24.128 | $SO_2CH_3$ | $SO_2(nC_3H_7)$ |
| 24.129 | $SO_2CH_3$ | $SO_2(iC_3H_7)$ |
| 24.130 | $SO_2CH_3$ | $SO_2(nC_4H_9)$ |
| 24.131 | $SO_2CH_3$ | $SO_2(tC_4H_9)$ |
| 24.132 | $SO_2CH_3$ | $SO_2Ph$ |
| 24.133 | $SO_2CH_3$ | $NH_2$ |
| 24.134 | $SO_2CH_3$ | $NHCH_3$ |
| 24.135 | $SO_2CH_3$ | $NCH_3Ph$ |

TABLE 1-continued

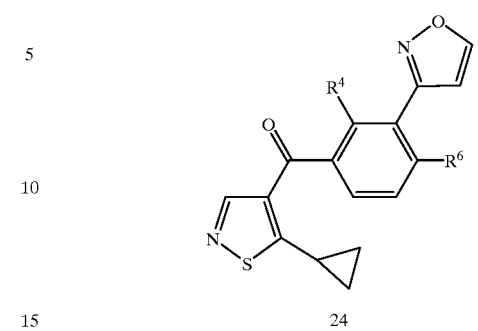

24

| No. | R⁴ | R⁶ |
|---|---|---|
| 24.136 | $SO_2CH_3$ | $N(CH_3)_2$ |
| 24.137 | $SO_2CH_3$ | $NPh_2$ |
| 24.138 | $SO_2CH_3$ | $CN$ |
| 24.139 | $SO_2CH_3$ | $NO_2$ |

TABLE 2

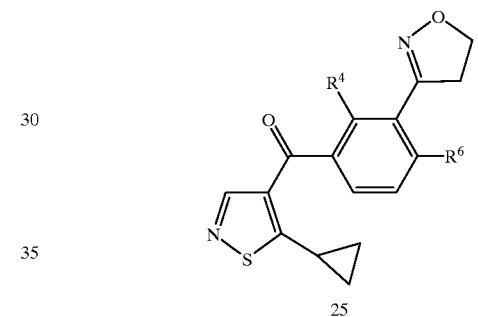

25

| No. | R⁴ | R⁶ |
|---|---|---|
| 25.1 | Cl | F |
| 25.2 | Cl | Cl |
| 25.3 | Cl | Br |
| 25.4 | Cl | $CH_3$ |
| 25.5 | Cl | $C_2H_5$ |
| 25.6 | Cl | $nC_3H_7$ |
| 25.7 | Cl | $iC_3H_7$ |
| 25.8 | Cl | $nC_4H_9$ |
| 25.9 | Cl | $tC_4H_9$ |
| 25.10 | Cl | Ph |
| 25.11 | Cl | OH |
| 25.12 | Cl | $OCH_3$ |
| 25.13 | Cl | $OC_2H_5$ |
| 25.14 | Cl | $O(nC_3H_7)$ |
| 25.15 | Cl | $O(iC_3H_7)$ |
| 25.16 | Cl | $O(nC_4H_9)$ |
| 25.17 | Cl | $O(tC_4H_9)$ |
| 25.18 | Cl | OPh |
| 25.19 | Cl | SH |
| 25.20 | Cl | $SCH_3$ |
| 25.21 | Cl | $SC_2H_5$ |
| 25.22 | Cl | $S(nC_3H_7)$ |
| 25.23 | Cl | $S(iC_3H_7)$ |
| 25.24 | Cl | $S(nC_4H_9)$ |
| 25.25 | Cl | $S(tC_4H_9)$ |
| 25.26 | Cl | SPh |
| 25.27 | Cl | $CCl_3$ |
| 25.28 | Cl | $CH_2F$ |
| 25.29 | Cl | $CHF_2$ |
| 25.30 | Cl | $CF_3$ |
| 25.31 | Cl | $CF_2CHF_2$ |
| 25.32 | Cl | $SO_3H$ |
| 25.33 | Cl | $SO_2CH_3$ |

TABLE 2-continued

![Structure 25: benzoyl compound with 4,5-dihydroisoxazole at position 3, R4 at position 2, R6 at position 4, and a 5-cyclopropyl-isothiazol-4-yl ketone]

25

| No. | R⁴ | R⁶ |
|---|---|---|
| 25.34 | Cl | SO₂C₂H₅ |
| 25.35 | Cl | SO₂(nC₃H₇) |
| 25.36 | Cl | SO₂(iC₃H₇) |
| 25.37 | Cl | SO₂(nC₄H₉) |
| 25.38 | Cl | SO₂(tC₄H₉) |
| 25.39 | Cl | SO₂Ph |
| 25.40 | Cl | NH₂ |
| 25.41 | Cl | NHCH₃ |
| 25.42 | Cl | NCH₃Ph |
| 25.43 | Cl | N(CH₃)₂ |
| 25.44 | Cl | NPh₂ |
| 25.45 | Cl | CN |
| 25.46 | Cl | NO₂ |
| 25.47 | CH₃ | F |
| 25.48 | CH₃ | Cl |
| 25.49 | CH₃ | Br |
| 25.50 | CH₃ | CH₃ |
| 25.51 | CH₃ | C₂H₅ |
| 25.53 | CH₃ | nC₃H₇ |
| 25.54 | CH₃ | iC₃H₇ |
| 25.55 | CH₃ | nC₄H₉ |
| 25.56 | CH₃ | tC₄H₉ |
| 25.57 | CH₃ | Ph |
| 25.58 | CH₃ | OH |
| 25.59 | CH₃ | OCH₃ |
| 25.60 | CH₃ | OC₂H₅ |
| 25.61 | CH₃ | O(nC₃H₇) |
| 25.62 | CH₃ | O(iC₃H₇) |
| 25.63 | CH₃ | O(nC₄H₉) |
| 25.64 | CH₃ | O(C₄H₉) |
| 25.65 | CH₃ | OPh |
| 25.66 | CH₃ | SH |
| 25.67 | CH₃ | SCH₃ |
| 25.68 | CH₃ | SC₂H₅ |
| 25.69 | CH₃ | S(nC₃H₇) |
| 25.70 | CH₃ | S(iC₃H₇) |
| 25.71 | CH₃ | S(nC₄H₉) |
| 25.72 | CH₃ | S(tC₄H₉) |
| 25.73 | CH₃ | SPh |
| 25.74 | CH₃ | CCl₃ |
| 25.75 | CH₃ | CH₂F |
| 25.76 | CH₃ | CHF₂ |
| 25.77 | CH₃ | CF₃ |
| 25.78 | CH₃ | CF₂CHF₂ |
| 25.79 | CH₃ | SO₃H |
| 25.80 | CH₃ | SO₂CH₃ |
| 25.81 | CH₃ | SO₂C₂H₅ |
| 25.82 | CH₃ | SO₂(nC₃H₇) |
| 25.83 | CH₃ | SO₂(iC₃H₇) |
| 25.84 | CH₃ | SO₂(nC₄H₉) |
| 25.85 | CH₃ | SO₂(tC₄H₉) |
| 25.86 | CH₃ | SO₂Ph |
| 25.87 | CH₃ | NH₂ |
| 25.88 | CH₃ | NHCH₃ |
| 25.89 | CH₃ | NCH₃Ph |
| 25.90 | CH₃ | N(CH₃)₂ |
| 25.91 | CH₃ | NPh₂ |
| 25.92 | CH₃ | CN |
| 25.93 | CH₃ | NO₂ |
| 25.94 | SO₂CH₃ | F |
| 25.95 | SO²CH₃ | Cl |
| 25.96 | SO₂CH₃ | Br |
| 25.97 | SO₂CH₃ | CH₃ |
| 25.98 | SO₂CH₃ | C₂H₅ |
| 25.99 | SO₂CH₃ | nC₃H₇ |
| 25.100 | SO₂CH₃ | iC₃H₇ |
| 25.101 | SO₂CH₃ | nC₄H₉ |
| 25.102 | SO₂CH₃ | tC₄H₉ |
| 25.103 | SO₂CH₃ | Ph |
| 25.104 | SO₂CH₃ | OH |
| 25.105 | SO₂CH₃ | OCH₃ |
| 25.106 | SO₂CH₃ | OC₂H₅ |
| 25.107 | SO₂CH₃ | O(nC₃H₇) |
| 25.108 | SO₂CH₃ | O(iC₃H₇) |
| 25.109 | SO₂CH₃ | O(nC₄H₉) |
| 25.110 | SO₂CH₃ | O(tC₄H₉) |
| 25.111 | SO₂CH₃ | OPh |
| 25.112 | SO₂CH₃ | SH |
| 25.113 | SO₂CH₃ | SCH₃ |
| 25.114 | SO₂CH₃ | SC₂H₅ |
| 25.115 | SO₂CH₃ | S(nC₃H₇) |
| 25.116 | SO₂CH₃ | S(iC₃H₇) |
| 25.117 | SO₂CH₃ | S(nC₄H₉) |
| 25.118 | SO₂CH₃ | S(tC₄H₉) |
| 25.119 | SO₂CH₃ | SPh |
| 25.120 | SO₂CH₃ | CCl₃ |
| 25.121 | SO₂CH₃ | CH₂F |
| 25.122 | SO₂CH₃ | CHF₂ |
| 25.123 | SO₂CH₃ | CF₃ |
| 25.124 | SO₂CH₃ | CF₂CHF₂ |
| 25.125 | SO₂CH₃ | SO₃H |
| 25.126 | SO₂CH₃ | SO₂CH₃ |
| 25.127 | SO₂CH₃ | SO₂C₂H₅ |
| 25.128 | SO₂CH₃ | SO₂(nC₃H₇) |
| 25.129 | SO₂CH₃ | SO₂(iC₃H₇) |
| 25.130 | SO₂CH₃ | SO₂(nC₄H₉) |
| 25.131 | SO₂CH₃ | SO₂(tC₄H₉) |
| 25.132 | SO₂CH₃ | SO₂Ph |
| 25.133 | SO₂CH₃ | NH₂ |
| 25.134 | SO₂CH₃ | NHCH₃ |
| 25.135 | SO₂CH₃ | NCH₃Ph |
| 25.136 | SO₂CH₃ | N(CH₃)₂ |
| 25.137 | SO₂CH₃ | NPh₂ |
| 25.138 | SO₂CH₃ | CN |
| 25.139 | SO₂CH₃ | NO₂ |

TABLE 3

Structure with R⁴, R⁶ substituents on benzoyl-isothiazole-thiazole scaffold (26)

| No. | R⁴ | R⁶ |
|---|---|---|
| 26.1 | Cl | F |
| 26.2 | Cl | Cl |
| 26.3 | Cl | Br |
| 26.4 | Cl | CH₃ |
| 26.5 | Cl | C₂H₅ |
| 26.6 | Cl | nC₃H₇ |
| 26.7 | Cl | iC₃H₇ |
| 26.8 | Cl | nC₄H₉ |
| 26.9 | Cl | tC₄H₉ |
| 26.10 | Cl | Ph |
| 26.11 | Cl | OH |
| 26.12 | Cl | OCH₃ |
| 26.13 | Cl | OC₂H₅ |
| 26.14 | Cl | O(nC₃H₇) |
| 26.15 | Cl | O(iC₃H₇) |
| 26.16 | Cl | O(nC₄H₉) |
| 26.17 | Cl | O(tC₄H₉) |
| 26.18 | Cl | OPh |
| 26.19 | Cl | SH |
| 26.20 | Cl | SCH₃ |
| 26.21 | Cl | SC₂H₅ |
| 26.22 | Cl | S(nC₃H₇) |
| 26.23 | Cl | S(iC₃H₇) |
| 26.24 | Cl | S(nC₄H₉) |
| 26.25 | Cl | S(tC₄H₉) |
| 26.26 | Cl | SPh |
| 26.27 | Cl | CCl₃ |
| 26.28 | Cl | CH₂F |
| 26.29 | Cl | CHF₂ |
| 26.30 | Cl | CF₃ |
| 26.31 | Cl | CF₂CHF₂ |
| 26.32 | Cl | SO₃H |
| 26.33 | Cl | SO₂CH₃ |
| 26.34 | Cl | SO₂C₂H₅ |
| 26.35 | Cl | SO₂(nC₃H₇) |
| 26.36 | Cl | SO₂(iC₃H₇) |
| 26.37 | Cl | SO₂(nC₄H₉) |
| 26.38 | Cl | SO₂(tC₄H₉) |
| 26.39 | Cl | SO₂Ph |
| 26.40 | Cl | NH₂ |
| 26.41 | Cl | NHCH₃ |
| 26.42 | Cl | NCH₃Ph |
| 26.43 | Cl | N(CH₃)₂ |
| 26.44 | Cl | NPh₂ |
| 26.45 | Cl | CN |
| 26.46 | Cl | NO₂ |
| 26.47 | CH₃ | F |
| 26.48 | CH₃ | Cl |
| 26.49 | CH₃ | Br |
| 26.50 | CH₃ | CH₃ |
| 26.51 | CH₃ | C₂H₅ |
| 26.53 | CH₃ | nC₃H₇ |
| 26.54 | CH₃ | iC₃H₇ |
| 26.55 | CH₃ | nC₄H₉ |
| 26.56 | CH₃ | tC₄H₉ |
| 26.57 | CH₃ | Ph |
| 26.58 | CH₃ | OH |
| 26.59 | CH₃ | OCH₃ |
| 26.60 | CH₃ | OC₂H₅ |
| 26.61 | CH₃ | O(nC₃H₇) |
| 26.62 | CH₃ | O(iC₃H₇) |
| 26.63 | CH₃ | O(nC₄H₉) |
| 26.64 | CH³ | O(tC₄H₉) |
| 26.65 | CH₃ | OPh |
| 26.66 | CH₃ | SH |
| 26.67 | CH₃ | SCH₃ |
| 26.68 | CH₃ | SC₂H₅ |
| 26.69 | CH₃ | S(nC₃H₇) |
| 26.70 | CH₃ | S(iC₃H₇) |
| 26.71 | CH₃ | S(nC₄H₉) |
| 26.72 | CH₃ | S(tC₄H₉) |
| 26.73 | CH₃ | SPh |
| 26.74 | CH₃ | CCl₃ |
| 26.75 | CH₃ | CH₂F |
| 26.76 | CH₃ | CHF₂ |
| 26.77 | CH₃ | CF₃ |
| 26.78 | CH₃ | CF₂CHF₂ |
| 26.79 | CH₃ | SO₃H |
| 26.80 | CH₃ | SO₂CH₃ |
| 26.81 | CH₃ | SO₂C₂H₅ |
| 26.82 | CH₃ | SO₂(nC₃H₇) |
| 26.83 | CH₃ | SO₂(iC₃H₇) |
| 26.84 | CH₃ | SO₂(nC₄H₉) |
| 26.85 | CH₃ | SO₂(tC₄H₉) |
| 26.86 | CH₃ | SO₂Ph |
| 26.87 | CH₃ | NH₂ |
| 26.88 | CH₃ | NHCH₃ |
| 26.89 | CH₃ | NCH₃Ph |
| 26.90 | CH₃ | N(CH₃)₂ |
| 26.91 | CH₃ | NPh₂ |
| 26.92 | CH₃ | CN |
| 26.93 | CH₃ | NO₂ |
| 26.94 | SO₂CH₃ | F |
| 26.95 | SO₂CH₃ | Cl |
| 26.96 | SO₂CH₃ | Br |
| 26.97 | SO₂CH₃ | CH₃ |
| 26.98 | SO₂CH₃ | C₂H₅ |
| 26.99 | SO₂CH₃ | nC₃H₇ |
| 26.100 | SO₂CH₃ | iC₃H₇ |
| 26.101 | SO₂CH₃ | nC₄H₉ |
| 26.102 | SO₂CH₃ | tC₄H₉ |
| 26.103 | SO₂CH₃ | Ph |
| 26.104 | SO₂CH₃ | OH |
| 26.105 | SO₂CH₃ | OCH₃ |
| 26.106 | SO₂CH₃ | OC₂H₅ |
| 26.107 | SO₂CH₃ | O(nC₃H₇) |
| 26.108 | SO₂CH₃ | O(iC₃H₇) |
| 26.109 | SO₂CH₃ | O(nC₄H₉) |
| 26.110 | SO₂CH₃ | O(tC₄H₉) |
| 26.111 | SO₂CH₃ | OPh |
| 26.112 | SO₂CH₃ | SH |
| 26.113 | SO₂CH₃ | SCH₃ |
| 26.114 | SO₂CH₃ | SC₂H₅ |
| 26.115 | SO₂CH₃ | S(nC₃H₇) |
| 26.116 | SO₂CH₃ | S(iC₃H₇) |
| 26.117 | SO₂CH₃ | S(nC₄H₉) |
| 26.118 | SO₂CH₃ | S(tC₄H₉) |
| 26.119 | SO₂CH₃ | SPh |
| 26.120 | SO₂CH₃ | CCl₃ |
| 26.121 | SO₂CH₃ | CH₂F |
| 26.122 | SO₂CH₃ | CHF₂ |
| 26.123 | SO₂CH₃ | CF₃ |
| 26.124 | SO₂CH₃ | CF₂CHF₂ |
| 26.125 | SO₂CH₃ | SO₃H |

TABLE 3-continued

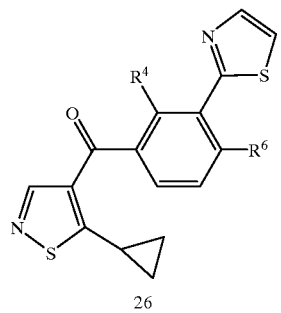

26

| No. | R⁴ | R⁶ |
|---|---|---|
| 26.126 | $SO_2CH_3$ | $SO_2CH_3$ |
| 26.127 | $SO_2CH_3$ | $SO_2C_2H_5$ |
| 26.128 | $SO_2CH_3$ | $SO_2(nC_3H_7)$ |
| 26.129 | $SO_2CH_3$ | $SO_2(iC_3H_7)$ |
| 26.130 | $SO_2CH_3$ | $SO_2(nC_4H_9)$ |
| 26.131 | $SO_2CH_3$ | $SO_2(tC_4H_9)$ |
| 26.132 | $SO_2CH_3$ | $SO_2Ph$ |
| 26.133 | $SO_2CH_3$ | $NH_2$ |
| 26.134 | $SO_2CH_3$ | $NHCH_3$ |
| 26.135 | $SO_2CH_3$ | $NCH_3Ph$ |
| 26.136 | $SO_2CH_3$ | $N(CH_3)_2$ |
| 26.137 | $SO_2CH_3$ | $NPh_2$ |
| 26.138 | $SO_2CH_3$ | $CN$ |
| 26.139 | $SO_2CH_3$ | $NO_2$ |

TABLE 4

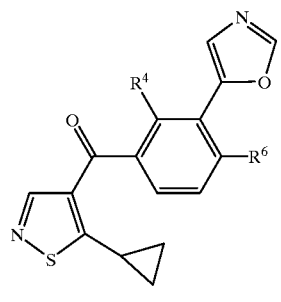

27

| No. | R⁴ | R⁶ |
|---|---|---|
| 27.1 | Cl | F |
| 27.2 | Cl | Cl |
| 27.3 | Cl | Br |
| 27.4 | Cl | $CH_3$ |
| 27.5 | Cl | $C_2H_5$ |
| 27.6 | Cl | $nC_3H_7$ |
| 27.7 | Cl | $iC_3H_7$ |
| 27.8 | Cl | $nC_4H_9$ |
| 27.9 | Cl | $tC_4H_9$ |
| 27.10 | Cl | Ph |
| 27.11 | Cl | OH |
| 27.12 | Cl | $OCH_3$ |
| 27.13 | Cl | $OC_2H_5$ |
| 27.14 | Cl | $O(nC_3H_7)$ |
| 27.15 | Cl | $O(iC_3H_7)$ |
| 27.16 | Cl | $O(nC_4H_9)$ |
| 27.17 | Cl | $O(tC_4H_9)$ |
| 27.18 | Cl | OPh |
| 27.19 | Cl | SH |
| 27.20 | Cl | $SCH_3$ |
| 27.21 | Cl | $SC_2H_5$ |
| 27.22 | Cl | $S(nC_3H_7)$ |
| 27.23 | Cl | $S(iC_3H_7)$ |
| 27.24 | Cl | $S(nC_4H_9)$ |

TABLE 4-continued

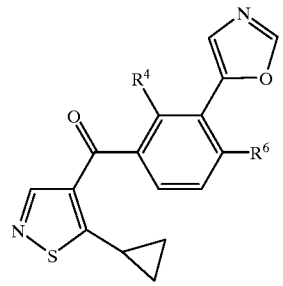

27

| No. | R⁴ | R⁶ |
|---|---|---|
| 27.25 | Cl | $S(tC_4H_9)$ |
| 27.26 | Cl | SPh |
| 27.27 | Cl | $CCl_3$ |
| 27.28 | Cl | $CH_2F$ |
| 27.29 | Cl | $CHF_2$ |
| 27.30 | Cl | $CF_3$ |
| 27.31 | Cl | $CF_2CHF_2$ |
| 27.32 | Cl | $SO_3H$ |
| 27.33 | Cl | $SO_2CH_3$ |
| 27.34 | Cl | $SO_2C_2H_5$ |
| 27.35 | Cl | $SO_2(nC_3H_7)$ |
| 27.36 | Cl | $SO_2(iC_3H_7)$ |
| 27.37 | Cl | $SO_2(nC_4H_9)$ |
| 27.38 | Cl | $SO_2(tC_4H_9)$ |
| 27.39 | Cl | $SO_2Ph$ |
| 27.40 | Cl | $NH_2$ |
| 27.41 | Cl | $NHCH_3$ |
| 27.42 | Cl | $NCH_3Ph$ |
| 27.43 | Cl | $N(CH_3)_2$ |
| 27.44 | Cl | $NPh_2$ |
| 27.45 | Cl | CN |
| 27.46 | Cl | $NO_2$ |
| 27.47 | $CH_3$ | F |
| 27.48 | $CH_3$ | Cl |
| 27.49 | $CH_3$ | Br |
| 27.50 | $CH_3$ | $CH_3$ |
| 27.51 | $CH_3$ | $C_2H_5$ |
| 27.52 | $CH_3$ | $nC_3H_7$ |
| 27.53 | $CH_3$ | $iC_3H_7$ |
| 27.54 | $CH_3$ | $nC_4H_9$ |
| 27.55 | $CH_3$ | $tC_4H_9$ |
| 27.56 | $CH_3$ | Ph |
| 27.57 | $CH_3$ | OH |
| 27.58 | $CH_3$ | $OCH_3$ |
| 27.59 | $CH_3$ | $OC_2H_5$ |
| 27.60 | $CH_3$ | $O(nC_3H_7)$ |
| 27.61 | $CH_3$ | $O(iC_3H_7)$ |
| 27.62 | $CH_3$ | $O(nC_4H_9)$ |
| 27.63 | $CH_3$ | $O(tC_4H_9)$ |
| 27.64 | $CH_3$ | OPh |
| 27.65 | $CH_3$ | SH |
| 27.66 | $CH_3$ | $SCH_3$ |
| 27.67 | $CH_3$ | $SC_2H_5$ |
| 27.68 | $CH_3$ | $S(nC_3H_7)$ |
| 27.69 | $CH_3$ | $S(iC_3H_7)$ |
| 27.70 | $CH_3$ | $S(nC_4H_9)$ |
| 27.71 | $CH_3$ | $S(tC_4H_9)$ |
| 27.72 | $CH_3$ | SPh |
| 27.73 | $CH_3$ | $CCl_3$ |
| 27.74 | $CH_3$ | $CH_2F$ |
| 27.75 | $CH_3$ | $CHF_2$ |
| 27.76 | $CH_3$ | $CF_3$ |
| 27.77 | $CH_3$ | $CF_2CHF_2$ |
| 27.78 | $CH_3$ | $SO_3H$ |
| 27.79 | $CH_3$ | $SO_2CH_3$ |
| 27.80 | $CH_3$ | $SO_2C_2H_5$ |
| 27.81 | $CH_3$ | $SO_2(nC_3H_7)$ |
| 27.82 | $CH_3$ | $SO_2(iC_3H_7)$ |
| 27.83 | $CH_3$ | $SO_2(nC_4H_9)$ |
| 27.84 | $CH_3$ | $SO_2(tC_4H_9)$ |

TABLE 4-continued

[Structure 27: benzoyl group with R⁴ ortho, oxazol-5-yl meta, R⁶ para on phenyl ring; attached to 5-cyclopropyl-isothiazol-4-yl via carbonyl]

| No. | R⁴ | R⁶ |
|---|---|---|
| 27.86 | CH³ | SO₂Ph |
| 27.87 | CH₃ | NH₂ |
| 27.88 | CH₃ | NHCH₃ |
| 27.89 | CH₃ | NCH₃Ph |
| 27.90 | CH₃ | N(CH₃)₂ |
| 27.91 | CH₃ | NPh₂ |
| 27.92 | CH₃ | CN |
| 27.93 | CH₃ | NO₂ |
| 27.94 | SO₂CH₃ | F |
| 27.95 | SO₂CH₃ | Cl |
| 27.96 | SO₂CH₃ | Br |
| 27.97 | SO₂CH₃ | CH₃ |
| 27.98 | SO₂CH₃ | C₂H₅ |
| 27.99 | SO₂CH₃ | nC₃H₇ |
| 27.100 | SO₂CH₃ | iC₃H₇ |
| 27.101 | SO₂CH₃ | nC₄H₉ |
| 27.102 | SO₂CH₃ | tC₄H₉ |
| 27.103 | SO₂CH₃ | Ph |
| 27.104 | SO₂CH₃ | OH |
| 27.105 | SO₂CH₃ | OCH₃ |
| 27.106 | SO₂CH₃ | OC₂H₅ |
| 27.107 | SO₂CH₃ | O(nC₃H₇) |
| 27.108 | SO₂CH₃ | O(iC₃H₇) |
| 27.109 | SO₂CH₃ | O(nC₄H₉) |
| 27.110 | SO₂CH₃ | O(tC₄H₉) |
| 27.111 | SO₂CH₃ | OPh |
| 27.112 | SO₂CH₃ | SH |
| 27.113 | SO₂CH₃ | SCH₃ |
| 27.114 | SO₂CH₃ | SC₂H₅ |
| 27.115 | SO₂CH₃ | S(nC₃H₇) |
| 27.116 | SO₂CH₃ | S(iC₃H₇) |
| 27.117 | SO₂CH₃ | S(nC₄H₉) |
| 27.118 | SO₂CH₃ | S(tC₄H₉) |
| 27.119 | SO₂CH₃ | SPh |
| 27.120 | SO₂CH₃ | CCl₃ |
| 27.121 | SO₂CH₃ | CH₂F |
| 27.122 | SO₂CH₃ | CHF₂ |
| 27.123 | SO₂CH₃ | CF₃ |
| 27.124 | SO₂CH₃ | CF₂CHF₂ |
| 27.125 | SO₂CH₃ | SO₃H |
| 27.126 | SO₂CH₃ | SO₂CH₃ |
| 27.127 | SO₂CH₃ | SO₂C₂H₅ |
| 27.128 | SO₂CH₃ | SO₂(nC₃H₇) |
| 27.129 | SO₂CH₃ | SO₂(iC₃H₇) |
| 27.130 | SO₂CH₃ | SO₂(nC₄H₉) |
| 27.131 | SO₂CH₃ | SO₂(tC₄H₉) |
| 27.132 | SO₂CH₃ | SO₂Ph |
| 27.133 | SO₂CH₃ | NH₂ |
| 27.134 | SO₂CH₃ | NHCH₃ |
| 27.135 | SO₂CH₃ | NCH₃Ph |
| 27.136 | SO₂CH₃ | N(CH₃)₂ |
| 27.137 | SO₂CH₃ | NPh₂ |
| 27.138 | SO₂CH₃ | CN |
| 27.139 | SO₂CH₃ | NO₂ |

TABLE 5

[Structure 28: benzoyl group with R⁴ ortho, furan-3-yl meta, R⁶ para on phenyl ring; attached to 5-cyclopropyl-isothiazol-4-yl via carbonyl]

| No. | R | R |
|---|---|---|
| 28.1 | Cl | F |
| 28.2 | Cl | Cl |
| 28.3 | Cl | Br |
| 28.4 | Cl | CH₃ |
| 28.5 | Cl | C₂H₅ |
| 28.6 | Cl | nC₃H₇ |
| 28.7 | Cl | iC₃H₇ |
| 28.8 | Cl | nC₄H₉ |
| 28.9 | Cl | tC₄H₉ |
| 28.10 | Cl | Ph |
| 28.11 | Cl | OH |
| 28.12 | Cl | OCH₃ |
| 28.13 | Cl | OC₂H₅ |
| 28.14 | Cl | O(nC₃H₇) |
| 28.15 | Cl | O(iC₃H₇) |
| 28.16 | Cl | O(nC₄H₉) |
| 28.17 | Cl | O(tC₄H9) |
| 28.18 | Cl | OPh |
| 28.19 | Cl | SH |
| 28.20 | Cl | SCH₃ |
| 28.21 | Cl | SC₂H₅ |
| 28.22 | Cl | S(nC₃H₇) |
| 28.23 | Cl | S(iC₃H₇) |
| 28.24 | Cl | S(nC₄H₉) |
| 28.25 | Cl | S(tC₄H₉) |
| 28.26 | Cl | SPh |
| 28.27 | Cl | CCl₃ |
| 28.28 | Cl | CH₂F |
| 28.29 | Cl | CHF₂ |
| 28.30 | Cl | CF₃ |
| 28.31 | Cl | CF₂CHF₂ |
| 28.32 | Cl | SO₃H |
| 28.33 | Cl | SO₂CH₃ |
| 28.34 | Cl | SO₂C₂H₅ |
| 28.35 | Cl | SO₂(nC₃H₇) |
| 28.36 | Cl | SO₂(iC₃H₇) |
| 28.37 | Cl | SO₂(nC₄H₉) |
| 28.38 | Cl | SO₂(tC₄H₉) |
| 28.39 | Cl | SO₂Ph |
| 28.40 | Cl | NH₂ |
| 28.41 | Cl | NHCH₃ |
| 28.42 | Cl | NCH₃Ph |
| 28.43 | Cl | N(CH₃)₂ |
| 28.44 | Cl | NPh₂ |
| 28.45 | Cl | CN |
| 28.46 | Cl | NO₂ |
| 28.47 | CH₃ | F |
| 28.48 | CH₃ | Cl |
| 28.49 | CH₃ | Br |
| 28.50 | CH₃ | CH₃ |
| 28.51 | CH₃ | C₂H₅ |
| 28.53 | CH₃ | nC₃H₇ |
| 28.54 | CH₃ | iC₃H₇ |
| 28.55 | CH₃ | nC₄H₉ |
| 28.56 | CH₃ | tC₄H₉ |
| 28.57 | CH₃ | Ph |
| 28.58 | CH₃ | OH |
| 28.59 | CH₃ | OCH₃ |
| 28.60 | CH₃ | OC₂H₅ |
| 28.61 | CH₃ | O(nC₃H₇) |

TABLE 5-continued

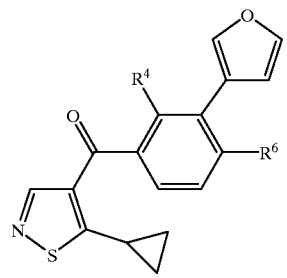

28

| No. | R | R |
|---|---|---|
| 28.62 | CH$_3$ | O(iC$_3$H$_7$) |
| 28.63 | CH$_3$ | O(nC$_4$H$_9$) |
| 28.64 | CH$_3$ | O(tC$_4$H$_9$) |
| 28.65 | CH$_3$ | OPh |
| 28.66 | CH$_3$ | SH |
| 28.67 | CH$_3$ | SCH$_3$ |
| 28.68 | CH$_3$ | SC$_2$H$_5$ |
| 28.69 | CH$_3$ | S(nC$_3$H$_7$) |
| 28.70 | CH$_3$ | S(iC$_3$H$_7$) |
| 28.71 | CH$_3$ | S(nC$_4$H$_9$) |
| 28.72 | CH$_3$ | S(tC$_4$H$_9$) |
| 28.73 | CH$_3$ | SPh |
| 28.74 | CH$_3$ | CCl$_3$ |
| 28.75 | CH$_3$ | CH$_2$F |
| 28.76 | CH$_3$ | CHF$_2$ |
| 28.77 | CH$_3$ | CF$_3$ |
| 28.78 | CH$_3$ | CF$_2$CHF$_2$ |
| 28.79 | CH$_3$ | SO$_3$H |
| 28.80 | CH$_3$ | SO$_2$CH$_3$ |
| 28.81 | CH$_3$ | SO$_2$C$_2$H$_5$ |
| 28.82 | CH$_3$ | SO$_2$(nC$_3$H$_7$) |
| 28.83 | CH$_3$ | SO$_2$(iC$_3$H$_7$) |
| 28.84 | CH$_3$ | SO$_2$(nC$_4$H$_9$) |
| 28.85 | CH$_3$ | SO$_2$(tC$_4$H$_9$) |
| 28.86 | CH$_3$ | SO$_2$Ph |
| 28.87 | CH$_3$ | NH$_2$ |
| 28.88 | CH$_3$ | NHCH$_3$ |
| 28.89 | CH$_3$ | NCH$_3$Ph |
| 28.90 | CH$_3$ | N(CH$_3$)$_2$ |
| 28.91 | CH$_3$ | NPh$_2$ |
| 28.92 | CH$_3$ | CN |
| 28.93 | CH$_3$ | NO$_2$ |
| 28.94 | SO$_2$CH$_3$ | F |
| 28.95 | SO$_2$CH$_3$ | Cl |
| 28.96 | SO$_2$CH$_3$ | Br |
| 28.97 | SO$_2$CH$_3$ | CH$_3$ |
| 28.98 | SO$_2$CH$_3$ | C$_2$H$_5$ |
| 28.99 | SO$_2$CH$_3$ | nC$_3$H$_7$ |
| 28.100 | SO$_2$CH\dn6 3 | iC$_3$H$_7$ |
| 28.101 | SO$_2$CH$_3$ | nC$_4$H$_9$ |
| 28.102 | SO$_2$CH$_3$ | tC$_4$H$_9$ |
| 28.103 | SO$_2$CH$_3$ | Ph |
| 28.104 | SO$_2$CH$_3$ | OH |
| 28.105 | SO$_2$CH$_3$ | OCH$_3$ |
| 28.106 | SO$_2$CH$_3$ | OC$_2$H$_5$ |
| 28.107 | SO$_2$CH$_3$ | O(nC$_3$H$_7$) |
| 28.108 | SO$_2$CH$_3$ | O(iC$_3$H$_7$) |
| 28.109 | SO$_2$CH$_3$ | O(nC$_4$H$_9$) |
| 28.110 | SO$_2$CH$_3$ | O(tC$_4$H$_9$) |
| 28.111 | SO$_2$CH$_3$ | OPh |
| 28.112 | SO$_2$CH$_3$ | SH |
| 28.113 | SO$_2$CH$_3$ | SCH$_3$ |
| 28.114 | SO$_2$CH$_3$ | SC$_2$H$_5$ |
| 28.115 | SO$_2$CH$_3$ | S(nC$_3$H$_7$) |
| 28.116 | SO$_2$CH$_3$ | S(iC$_3$H$_7$) |
| 28.117 | SO$_2$CH$_3$ | S(nC$_4$H$_9$) |
| 28.118 | SO$_2$CH$_3$ | S(tC$_4$H$_9$) |
| 28.119 | SO$_2$CH$_3$ | SPh |
| 28.120 | SO$_2$CH$_3$ | CCl$_3$ |
| 28.121 | SO$_2$CH$_3$ | CH$_2$F |

TABLE 5-continued

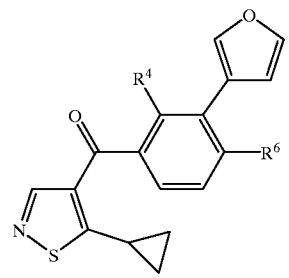

28

| No. | R | R |
|---|---|---|
| 28.122 | SO$_2$CH$_3$ | CHF$_2$ |
| 28.123 | SO$_2$CH$_3$ | CF$_3$ |
| 28.124 | SO$_2$CH$_3$ | CF$_2$CHF$_2$ |
| 28.125 | SO$_2$CH$_3$ | SO$_3$H |
| 28.126 | SO$_2$CH$_3$ | SO$_2$CH$_3$ |
| 28.127 | SO$_2$CH$_3$ | SO$_2$C$_2$H$_5$ |
| 28.128 | SO$_2$CH$_3$ | SO$_2$(nC$_3$H$_7$) |
| 28.129 | SO$_2$CH$_3$ | SO$_2$(iC$_3$H$_7$) |
| 28.130 | SO$_2$CH$_3$ | SO$_2$(nC$_4$H$_9$) |
| 28.131 | SO$_2$CH$_3$ | SO$_2$(tC$_4$H$_9$) |
| 28.132 | SO$_2$CH$_3$ | SO$_2$Ph |
| 28.133 | SO$_2$CH$_3$ | NH$_2$ |
| 28.134 | SO$_2$CH$_3$ | NHCH$_3$ |
| 28.135 | SO$_2$CH$_3$ | NCH$_3$Ph |
| 28.136 | SO$_2$CH$_3$ | N(CH$_3$)$_2$ |
| 28.137 | SO$_2$CH$_3$ | NPh$_2$ |
| 28.138 | SO$_2$CH$_3$ | CN |
| 28.139 | SO$_2$CH$_3$ | NO$_2$ |

TABLE 6

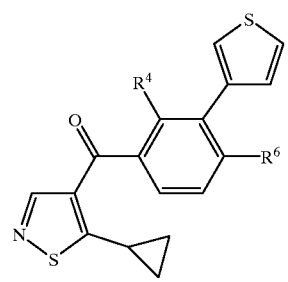

29

| No. | R | R |
|---|---|---|
| 29.1 | Cl | F |
| 29.2 | Cl | Cl |
| 29.3 | Cl | Br |
| 29.4 | Cl | CH$_3$ |
| 29.5 | Cl | C$_2$H$_5$ |
| 29.6 | Cl | nC$_3$H$_7$ |
| 29.7 | Cl | iC$_3$H$_7$ |
| 29.8 | Cl | nC$_4$H$_9$ |
| 29.9 | Cl | tC$_4$H$_9$ |
| 29.10 | Cl | Ph |
| 29.11 | Cl | OH |
| 29.12 | Cl | OCH$_3$ |
| 29.13 | Cl | OC$_2$H$_5$ |
| 29.14 | Cl | O(nC$_3$H$_7$) |
| 29.15 | Cl | O(iC$_3$H$_7$) |
| 29.16 | Cl | O(nC$_4$H$_9$) |
| 29.17 | Cl | O(tC$_4$H$_9$) |
| 29.18 | Cl | OPh |
| 29.19 | Cl | SH |
| 29.20 | Cl | SCH$_3$ |

TABLE 6-continued

![Structure 29: isothiazole (5-cyclopropyl) with carbonyl linker to benzene ring bearing R4, thiophene, and R6 substituents]

29

| No. | R | R |
|---|---|---|
| 29.21 | Cl | SC$_2$H$_5$ |
| 29.22 | Cl | S(nC$_3$H$_7$) |
| 29.23 | Cl | S(iC$_3$H$_7$) |
| 29.24 | Cl | S(nC$_4$H$_9$) |
| 29.25 | Cl | S(tC$_4$H$_9$) |
| 29.26 | Cl | SPh |
| 29.27 | Cl | CCl$_3$ |
| 29.28 | Cl | CH$_2$F |
| 29.29 | Cl | CHF$_2$ |
| 29.30 | Cl | CF$_3$ |
| 29.31 | Cl | CF$_2$CHF$_2$ |
| 29.32 | Cl | SO$_3$H |
| 29.33 | Cl | SO$_2$CH$_3$ |
| 29.34 | Cl | SO$_2$C$_2$H$_5$ |
| 29.35 | Cl | SO$_2$(nC$_3$H$_7$) |
| 29.36 | Cl | SO$_2$(iC$_3$H$_7$) |
| 29.37 | Cl | SO$_2$(nC$_4$H$_9$) |
| 29.38 | Cl | SO$_2$(tC$_4$H$_9$) |
| 29.39 | Cl | SO$_2$Ph |
| 29.40 | Cl | NH$_2$ |
| 29.41 | Cl | NHCH$_3$ |
| 29.42 | Cl | NCH$_3$Ph |
| 29.43 | Cl | N(CH$_3$)$_2$ |
| 29.44 | Cl | NPh$_2$ |
| 29.45 | Cl | CN |
| 29.46 | Cl | NO$_2$ |
| 29.47 | CH$_3$ | F |
| 29.48 | CH$_3$ | Cl |
| 29.49 | CH$_3$ | Br |
| 29.50 | CH$_3$ | CH$_3$ |
| 29.51 | CH$_3$ | C$_2$H$_5$ |
| 29.53 | CH$_3$ | nC$_3$H$_7$ |
| 29.54 | CH$_3$ | iC$_3$H$_7$ |
| 29.55 | CH$_3$ | nC$_4$H$_9$ |
| 29.56 | CH$_3$ | tC$_4$H$_9$ |
| 29.57 | CH$_3$ | Ph |
| 29.58 | CH$_3$ | OH |
| 29.59 | CH$_3$ | OCH$_3$ |
| 29.60 | CH$_3$ | OC$_2$H$_5$ |
| 29.61 | CH$_3$ | O(nC$_3$H$_7$) |
| 29.62 | CH$_3$ | O(iC$_3$H$_7$) |
| 29.63 | CH$_3$ | O(nC$_4$H$_9$) |
| 29.64 | CH$_3$ | O(tC$_4$H$_9$) |
| 29.65 | CH$_3$ | OPh |
| 29.66 | CH$_3$ | SH |
| 29.67 | CH$_3$ | SCH$_3$ |
| 29.68 | CH$_3$ | SC$_2$H$_5$ |
| 29.69 | CH$_3$ | S(nC$_3$H$_7$) |
| 29.70 | CH$_3$ | S(iC$_3$H$_7$) |
| 29.71 | CH$_3$ | S(nC$_4$H$_9$) |
| 29.72 | CH$_3$ | S(tC$_4$H$_9$) |
| 29.73 | CH$_3$ | SPh |
| 29.74 | CH$_3$ | CCl$_3$ |
| 29.75 | CH$_3$ | CH$_2$F |
| 29.76 | CH$_3$ | CHF$_2$ |
| 29.77 | CH$_3$ | CF$_3$ |
| 29.78 | CH$_3$ | CF$_2$CHF$_2$ |
| 29.79 | CH$_3$ | SO$_3$H |
| 29.80 | CH$_3$ | SO$_2$CH$_3$ |
| 29.81 | CH$_3$ | SO$_2$C$_2$H$_5$ |
| 29.82 | CH$_3$ | SO$_2$(nC$_3$H$_7$) |
| 29.83 | CH$_3$ | SO$_2$(iC$_3$H$_7$) |
| 29.84 | CH$_3$ | SO$_2$(nC$_4$H$_9$) |
| 29.85 | CH$_3$ | SO$_2$(tC$_4$H$_9$) |
| 29.86 | CH$_3$ | SO$_2$Ph |
| 29.87 | CH$_3$ | NH$_2$ |
| 29.88 | CH$_3$ | NHCH$_3$ |
| 29.89 | CH$_3$ | NCH$_3$Ph |
| 29.90 | CH$_3$ | N(CH$_3$)$_2$ |
| 29.91 | CH$_3$ | NPh$_2$ |
| 29.92 | CH$_3$ | CN |
| 29.93 | CH$_3$ | NO$_2$ |
| 29.94 | SO$_2$CH$_3$ | F |
| 29.95 | SO$_2$CH$_3$ | Cl |
| 29.96 | SO$_2$CH$_3$ | Br |
| 29.97 | SO$_2$CH$_3$ | CH$_3$ |
| 29.98 | SO$_2$CH$_3$ | C$_2$H$_5$ |
| 29.99 | SO$_2$CH$_3$ | nC$_3$H$_7$ |
| 29.100 | SO$_2$CH$_3$ | iC$_3$H$_7$ |
| 29.101 | SO$_2$CH$_3$ | nC$_4$H$_9$ |
| 29.102 | SO$_2$CH$_3$ | tC$_4$H$_9$ |
| 29.103 | SO$_2$CH$_3$ | Ph |
| 29.104 | SO$_2$CH$_3$ | OH |
| 29.105 | SO$_2$CH$_3$ | OCH$_3$ |
| 29.106 | SO$_2$CH$_3$ | OC$_2$H$_5$ |
| 29.107 | SO$_2$CH$_3$ | O(nC$_3$H$_7$) |
| 29.108 | SO$_2$CH$_3$ | O(iC$_3$H$_7$) |
| 29.109 | SO$_2$CH$_3$ | O(nC$_4$H$_9$) |
| 29.110 | SO$_2$CH$_3$ | O(tC$_4$H9) |
| 29.111 | SO$_2$CH$_3$ | OPh |
| 29.112 | SO$_2$CH$_3$ | SH |
| 29.113 | SO$_2$CH$_3$ | SCH$_3$ |
| 29.114 | SO$_2$CH$_3$ | SC$_2$H$_5$ |
| 29.115 | SO$_2$CH$_3$ | S(nC$_3$H$_7$) |
| 29.116 | SO$_2$CH$_3$ | S(iC$_3$H$_7$) |
| 29.117 | SO$_2$CH$_3$ | S(nC$_4$H$_9$) |
| 29.118 | SO$_2$CH$_3$ | S(tC$_4$H$_9$) |
| 29.119 | SO$_2$CH$_3$ | SPh |
| 29.120 | SO$_2$CH$_3$ | CCl$_3$ |
| 29.121 | SO$_2$CH$_3$ | CH$_2$F |
| 29.122 | SO$_2$CH$_3$ | CHF$_2$ |
| 29.123 | SO$_2$CH$_3$ | CF$_3$ |
| 29.124 | SO$_2$CH$_3$ | CF$_2$CHF$_2$ |
| 29.125 | SO$_2$CH$_3$ | SO$_3$H |
| 29.126 | SO$_2$CH$_3$ | SO$_2$CH$_3$ |
| 29.127 | SO$_2$CH$_3$ | SO$_2$C$_2$H$_5$ |
| 29.128 | SO$_2$CH$_3$ | SO$_2$(nC$_3$H$_7$) |
| 29.129 | SO$_2$CH$_3$ | SO$_2$(iC$_3$H$_7$) |
| 29.130 | SO$_2$CH$_3$ | SO$_2$(nC$_4$H$_9$) |
| 29.131 | SO$_2$CH$_3$ | SO$_2$(tC$_4$H$_9$) |
| 29.132 | SO$_2$CH$_3$ | SO$_2$Ph |
| 29.133 | SO$_2$CH$_3$ | NH$_2$ |
| 29.134 | SO$_2$CH$_3$ | NHCH$_3$ |
| 29.135 | SO$_2$CH$_3$ | NCH$_3$Ph |
| 29.136 | SO$_2$CH$_3$ | N(CH$_3$)$_2$ |
| 29.137 | SO$_2$CH$_3$ | NPh$_2$ |
| 29.138 | SO$_2$CH$_3$ | CN |
| 29.139 | SO$_2$CH$_3$ | NO$_2$ |

TABLE 7

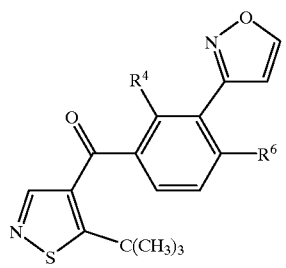
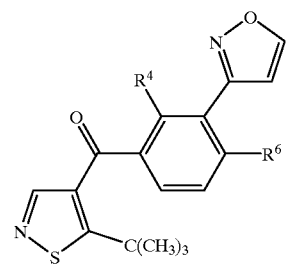

| No. | R | R |
|---|---|---|
| 30.1 | Cl | F |
| 30.2 | Cl | Cl |
| 30.3 | Cl | Br |
| 30.4 | Cl | CH$_3$ |
| 30.5 | Cl | C$_2$H$_5$ |
| 30.6 | Cl | nC$_3$H$_7$ |
| 30.7 | Cl | iC$_3$H$_7$ |
| 30.8 | Cl | nC$_4$H$_9$ |
| 30.9 | Cl | tC$_4$H$_9$ |
| 30.10 | Cl | Ph |
| 30.11 | Cl | OH |
| 30.12 | Cl | OCH$_3$ |
| 30.13 | Cl | OC$_2$H$_5$ |
| 30.14 | Cl | O(nC$_3$H$_7$) |
| 30.15 | Cl | O(iC$_3$H$_7$) |
| 30.16 | Cl | O(nC$_4$H$_9$) |
| 30.17 | Cl | O(tC$_4$H$_9$) |
| 30.18 | Cl | OPh |
| 30.19 | Cl | SH |
| 30.20 | Cl | SCH$_3$ |
| 30.21 | Cl | SC$_2$H$_5$ |
| 30.22 | Cl | S(nC$_3$H$_7$) |
| 30.23 | Cl | S(iC$_3$H$_7$) |
| 30.24 | Cl | S(nC$_4$H$_9$) |
| 30.25 | Cl | S(tC$_4$H$_9$) |
| 30.26 | Cl | SPh |
| 30.27 | Cl | CCl$_3$ |
| 30.28 | Cl | CH$_2$F |
| 30.29 | Cl | CHF$_2$ |
| 30.30 | Cl | CF$_3$ |
| 30.31 | Cl | CF$_2$CHF$_2$ |
| 30.32 | Cl | SO$_3$H |
| 30.33 | Cl | SO$_2$CH$_3$ |
| 30.34 | Cl | SO$_2$C$_2$H$_5$ |
| 30.35 | Cl | SO$_2$(nC$_3$H$_7$) |
| 30.36 | Cl | SO$_2$(iC$_3$H$_7$) |
| 30.37 | Cl | SO$_2$(nC$_4$H$_9$) |
| 30.38 | Cl | SO$_2$(tC$_4$H$_9$) |
| 30.39 | Cl | SO$_2$Ph |
| 30.40 | Cl | NH$_2$ |
| 30.41 | Cl | NHCH$_3$ |
| 30.42 | Cl | NCH$_3$Ph |
| 30.43 | Cl | N(CH$_3$)$_2$ |
| 30.44 | Cl | NPh$_2$ |
| 30.45 | Cl | CN |
| 30.46 | Cl | NO$_2$ |
| 30.47 | CH$_3$ | F |
| 30.48 | CH$_3$ | Cl |
| 30.49 | CH$_3$ | Br |
| 30.50 | CH$_3$ | CH$_3$ |
| 30.51 | CH$_3$ | C$_2$H$_5$ |
| 30.53 | CH$_3$ | nC$_3$H$_7$ |
| 30.54 | CH$_3$ | iC$_3$H$_7$ |
| 30.55 | CH$_3$ | nC$_4$H$_9$ |
| 30.56 | CH$_3$ | tC$_4$H$_9$ |
| 30.57 | CH$_3$ | Ph |
| 30.58 | CH$_3$ | OH |
| 30.59 | CH$_3$ | OCH$_3$ |
| 30.60 | CH$_3$ | OC$_2$H$_5$ |
| 30.61 | CH$_3$ | O(nC$_3$H$_7$) |
| 30.62 | CH$_3$ | O(iC$_3$H$_7$) |
| 30.63 | CH$_3$ | O(nC$_4$H$_9$) |
| 30.64 | CH$_3$ | O(tC$_4$H$_9$) |
| 30.65 | CH$_3$ | OPh |
| 30.66 | CH$_3$ | SH |
| 30.67 | CH$_3$ | SCH$_3$ |
| 30.68 | CH$_3$ | SC$_2$H$_5$ |
| 30.69 | CH$_3$ | S(nC$_3$H$_7$) |
| 30.70 | CH$_3$ | S(iC$_3$H$_7$) |
| 30.71 | CH$_3$ | S(nC$_4$H$_9$) |
| 30.72 | CH$_3$ | S(tC$_4$H$_9$) |
| 30.73 | CH$_3$ | SPh |
| 30.74 | CH$_3$ | CCl$_3$ |
| 30.75 | CH$_3$ | CH$_2$F |
| 30.76 | CH$_3$ | CHF$_2$ |
| 30.77 | CH$_3$ | CF$_3$ |
| 30.78 | CH$_3$ | CF$_2$CHF$_2$ |
| 30.79 | CH$_3$ | SO$_3$H |
| 30.80 | CH$_3$ | SO$_2$CH$_3$ |
| 30.81 | CH$_3$ | SO$_2$C$_2$H$_5$ |
| 30.82 | CH$_3$ | SO$_2$(nC$_3$H$_7$) |
| 30.83 | CH$_3$ | SO$_2$(iC$_3$H$_7$) |
| 30.84 | CH$_3$ | SO$_2$(nC$_4$H$_9$) |
| 30.85 | CH$_3$ | SO$_2$(tC$_4$H$_9$) |
| 30.86 | CH$_3$ | SO$_2$Ph |
| 30.87 | CH$_3$ | NH$_2$ |
| 30.88 | CH$_3$ | NHCH$_3$ |
| 30.89 | CH$_3$ | NCH$_3$Ph |
| 30.90 | CH$_3$ | N(CH$_3$)$_2$ |
| 30.91 | CH$_3$ | NPh$_2$ |
| 30.92 | CH$_3$ | CN |
| 30.93 | CH$_3$ | NO$_2$ |
| 30.94 | SO$_2$CH$_3$ | F |
| 30.95 | SO$_2$CH$_3$ | Cl |
| 30.96 | SO$_2$CH$_3$ | Br |
| 30.97 | SO$_2$CH$_3$ | CH$_3$ |
| 30.98 | SO$_2$CH$_3$ | C$_2$H$_5$ |
| 30.99 | SO$_2$CH$_3$ | nC$_3$H$_7$ |
| 30.100 | SO$_2$CH$_3$ | iC$_3$H$_7$ |
| 30.101 | SO$_2$CH$_3$ | nC$_4$H$_9$ |
| 30.102 | SO$_2$CH$_3$ | tC$_4$H$_9$ |
| 30.103 | SO$_2$CH$_3$ | Ph |
| 30.104 | SO$_2$CH$_3$ | OH |
| 30.105 | SO$_2$CH$_3$ | OCH$_3$ |
| 30.106 | SO$_2$CH$_3$ | OC$_2$H$_5$ |
| 30.107 | SO$_2$CH$_3$ | O(nC$_3$H$_7$) |
| 30.108 | SO$_2$CH$_3$ | O(iC$_3$H$_7$) |
| 30.109 | SO$_2$CH$_3$ | O(nC$_4$H$_9$) |
| 30.110 | SO$_2$CH$_3$ | O(tC$_4$H$_9$) |
| 30.111 | SO$_2$CH$_3$ | OPh |
| 30.112 | SO$_2$CH$_3$ | SH |
| 30.113 | SO$_2$CH$_3$ | SCH$_3$ |
| 30.114 | SO$_2$CH$_3$ | SC$_2$H$_5$ |
| 30.115 | SO$_2$CH$_3$ | S(nC$_3$H$_7$) |
| 30.116 | SO$_2$CH$_3$ | S(iC$_3$H$_7$) |
| 30.117 | SO$_2$CH$_3$ | S(nC$_4$H$_9$) |
| 30.118 | SO$_2$CH$_3$ | S(tC$_4$H$_9$) |
| 30.119 | SO$_2$CH$_3$ | SPh |
| 30.120 | SO$_2$CH$_3$ | CCl$_3$ |
| 30.121 | SO$_2$CH$_3$ | CH$_2$F |

TABLE 7-continued

Structure 30: Isoxazole-phenyl-ketone-isothiazole with C(CH₃)₃, R⁴, R⁶ substituents

| No. | R | R |
|---|---|---|
| 30.122 | SO₂CH₃ | CHF₂ |
| 30.123 | SO₂CH₃ | CF₃ |
| 30.124 | SO₂CH₃ | CF₂CHF₂ |
| 30.125 | SO₂CH₃ | SO₃H |
| 30.126 | SO₂CH₃ | SO₂CH₃ |
| 30.127 | SO₂CH₃ | SO₂C₂H₅ |
| 30.128 | SO₂CH₃ | SO₂(nC₃H₇) |
| 30.129 | SO₂CH₃ | SO₂(iC₃H₇) |
| 30.130 | SO₂CH₃ | SO₂(nC₄H₉) |
| 30.131 | SO₂CH₃ | SO₂(tC₄H₉) |
| 30.132 | SO₂CH₃ | SO₂Ph |
| 30.133 | SO₂CH₃ | NH₂ |
| 30.134 | SO₂CH₃ | NHCH₃ |
| 30.135 | SO₂CH₃ | NCH₃Ph |
| 30.136 | SO₂CH₃ | N(CH₃)₂ |
| 30.137 | SO₂CH₃ | NPh₂ |
| 30.138 | SO₂CH₃ | CN |
| 30.139 | SO₂CH₃ | NO₂ |

TABLE 8

Structure 31: Dihydroisoxazole-phenyl-ketone-isothiazole with C(CH₃)₃, R⁴, R⁶ substituents

| No. | R | R |
|---|---|---|
| 31.1 | Cl | F |
| 31.2 | Cl | Cl |
| 31.3 | Cl | Br |
| 31.4 | Cl | CH₃ |
| 31.5 | Cl | C₂H₅ |
| 31.6 | Cl | nC₃H₇ |
| 31.7 | Cl | iC₃H₇ |
| 31.8 | Cl | nC₄H₉ |
| 31.9 | Cl | tC₄H₉ |
| 31.10 | Cl | Ph |
| 31.11 | Cl | OH |
| 31.12 | Cl | OCH₃ |
| 31.13 | Cl | OC₂H₅ |
| 31.14 | Cl | O(nC₃H₇) |
| 31.15 | Cl | O(iC₃H₇) |
| 31.16 | Cl | O(nC₄H₉) |
| 31.17 | Cl | O(tC₄H₉) |
| 31.18 | Cl | OPh |
| 31.19 | Cl | SH |
| 31.20 | Cl | SCH₃ |

TABLE 8-continued

| No. | R | R |
|---|---|---|
| 31.21 | Cl | SC₂H₅ |
| 31.22 | Cl | S(nC₃H₇) |
| 31.23 | Cl | S(iC₃H₇) |
| 31.24 | Cl | S(nC₄H₉) |
| 31.25 | Cl | S(tC₄H₉) |
| 31.26 | Cl | SPh |
| 31.27 | Cl | CCl₃ |
| 31.28 | Cl | CH₂F |
| 31.29 | Cl | CHF₂ |
| 31.30 | Cl | CF₃ |
| 31.31 | Cl | CF₂CHF₂ |
| 31.32 | Cl | SO₃H |
| 31.33 | Cl | SO₂CH₃ |
| 31.34 | Cl | SO₂C₂H₅ |
| 31.35 | Cl | SO₂(nC₃H₇) |
| 31.36 | Cl | SO₂(iC₃H₇) |
| 31.37 | Cl | SO₂(nC₄H₉) |
| 31.38 | Cl | SO₂(tC₄H₉) |
| 31.39 | Cl | SO₂Ph |
| 31.40 | Cl | NH₂ |
| 31.41 | Cl | NHCH₃ |
| 31.42 | Cl | NCH₃Ph |
| 31.43 | Cl | N(CH₃)₂ |
| 31.44 | Cl | NPh₂ |
| 31.45 | Cl | CN |
| 31.46 | Cl | NO₂ |
| 31.47 | CH₃ | F |
| 31.48 | CH₃ | Cl |
| 31.49 | CH₃ | Br |
| 31.50 | CH₃ | CH₃ |
| 31.51 | CH₃ | C₂H₅ |
| 31.53 | CH₃ | nC₃H₇ |
| 31.54 | CH₃ | iC₃H₇ |
| 31.55 | CH₃ | nC₄H₉ |
| 31.56 | CH₃ | tC₄H₉ |
| 31.57 | CH₃ | Ph |
| 31.58 | CH₃ | OH |
| 31.59 | CH₃ | OCH₃ |
| 31.60 | CH₃ | OC₂H₅ |
| 31.61 | CH₃ | O(nC₃H₇) |
| 31.62 | CH₃ | O(iC₃H₇) |
| 31.63 | CH₃ | O(nC₄H₉) |
| 31.64 | CH₃ | O(tC₄H₉) |
| 31.65 | CH₃ | OPh |
| 31.66 | CH₃ | SH |
| 31.67 | CH₃ | SCH₃ |
| 31.68 | CH₃ | SC₂H₅ |
| 31.69 | CH₃ | S(nC₃H₇) |
| 31.70 | CH₃ | S(iC₃H₇) |
| 31.71 | CH₃ | S(nC₄H₉) |
| 31.72 | CH₃ | S(tC₄H₉) |
| 31.73 | CH₃ | SPh |
| 31.74 | CH₃ | CCl₃ |
| 31.75 | CH₃ | CH₂F |
| 31.76 | CH₃ | CHF₂ |
| 31.77 | CH₃ | CF₃ |
| 31.78 | CH₃ | CF₂CHF₂ |
| 31.79 | CH₃ | SO₃H |
| 31.80 | CH₃ | SO₂CH₃ |
| 31.81 | CH₃ | SO₂C₂H₅ |
| 31.82 | CH₃ | SO₂(nC₂H₇) |

TABLE 8-continued

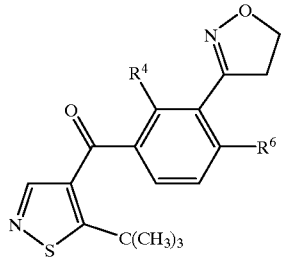

31

| No. | R | R |
|---|---|---|
| 31.83 | CH₃ | SO₂(iC₃H₇) |
| 31.84 | CH₃ | SO₂(nC₄H₉) |
| 31.85 | CH₃ | SO₂(tC₄H₉) |
| 31.86 | CH₃ | SO₂Ph |
| 31.87 | CH₃ | NH₂ |
| 31.88 | CH₃ | NHCH₃ |
| 31.89 | CH₃ | NCH₃Ph |
| 31.90 | CH₃ | N(CH₃)₂ |
| 31.91 | CH₃ | NPh₂ |
| 31.92 | CH₃ | CN |
| 31.93 | CH₃ | NO₂ |
| 31.94 | SO₂CH₃ | F |
| 31.95 | SO₂CH₃ | Cl |
| 31.96 | SO₂CH₃ | Br |
| 31.97 | SO₂CH₃ | CH₃ |
| 31.98 | SO₂CH₃ | C₂H₅ |
| 31.99 | SO₂CH₃ | nC₃H₇ |
| 31.100 | SO₂CH₃ | iC₃H₇ |
| 31.101 | SO₂CH₃ | nC₄H₉ |
| 31.102 | SO₂CH₃ | tC₄H₉ |
| 31.103 | SO₂CH₃ | Ph |
| 31.104 | SO₂CH₃ | OH |
| 31.105 | SO₂CH₃ | OCH₃ |
| 31.106 | SO₂CH₃ | OC₂H₅ |
| 31.107 | SO₂CH₃ | O(nC₃H₇) |
| 31.108 | SO₂CH₃ | O(iC₃H₇) |
| 31.109 | SO₂CH₃ | O(nC₄H₉) |
| 31.110 | SO₂CH₃ | O(tC₄H₉) |
| 31.111 | SO₂CH₃ | OPh |
| 31.112 | SO₂CH₃ | SH |
| 31.113 | SO₂CH₃ | SCH₃ |
| 31.114 | SO₂CH₃ | SC₂H₅ |
| 31.115 | SO₂CH₃ | S(nC₃H₇) |
| 31.116 | SO₂CH₃ | S(iC₃H₇) |
| 31.117 | SO₂CH₃ | S(nC₄H₉) |
| 31.118 | SO₂CH₃ | S(tC₄H₉) |
| 31.119 | SO₂CH₃ | SPh |
| 31.120 | SO₂CH₃ | CCl₃ |
| 31.121 | SO₂CH₃ | CH₂F |
| 31.122 | SO₂CH₃ | CHF₂ |
| 31.123 | SO₂CH₃ | CF₃ |
| 31.124 | SO₂CH₃ | CF₂CHF₂ |
| 31.125 | SO₂CH₃ | SO₃H |
| 31.126 | SO₂CH₃ | SO₂CH₃ |
| 31.127 | SO₂CH₃ | SO₂C₂H₅ |
| 31.128 | SO₂CH₃ | SO₂(nC₃H₇) |
| 31.129 | SO₂CH₃ | SO₂(iC₃H₇) |
| 31.130 | SO₂CH₃ | SO₂(nC₄H₉) |
| 31.131 | SO₂CH₃ | SO₂(tC₄H₉) |
| 31.132 | SO₂CH₃ | SO₂Ph |
| 31.133 | SO₂CH₃ | NH₂ |
| 31.134 | SO₂CH₃ | NHCH₃ |
| 31.135 | SO₂CH₃ | NCH₃Ph |
| 31.136 | SO₂CH₃ | N(CH₃)₂ |
| 31.137 | SO₂CH₃ | NPh₂ |
| 31.138 | SO₂CH₃ | CN |
| 31.139 | SO₂CH₃ | NO₂ |

TABLE 9

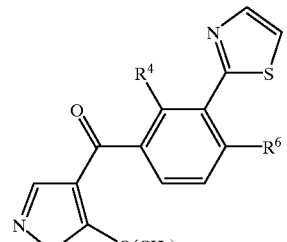

32

| No. | R⁴ | R⁶ |
|---|---|---|
| 32.1 | Cl | F |
| 32.2 | Cl | Cl |
| 32.3 | Cl | Br |
| 32.4 | Cl | CH₃ |
| 32.5 | Cl | C₂H₅ |
| 32.6 | Cl | nC₃H₇ |
| 32.7 | Cl | iC₃H₇ |
| 32.8 | Cl | nC₄H₉ |
| 32.9 | Cl | tC₄H₉ |
| 32.10 | Cl | Ph |
| 32.11 | Cl | OH |
| 32.12 | Cl | OCH₃ |
| 32.13 | Cl | OC₂H₅ |
| 32.14 | Cl | O(nC₃H₇) |
| 32.15 | Cl | O(iC₃H₇) |
| 32.16 | Cl | O(nC₄H₉) |
| 32.17 | Cl | O(tC₄H₉) |
| 32.18 | Cl | OPh |
| 32.19 | Cl | SH |
| 32.20 | Cl | SCH₃ |
| 32.21 | Cl | SC₂H₅ |
| 32.22 | Cl | S(nC₃H₇) |
| 32.23 | Cl | S(iC₃H₇) |
| 32.24 | Cl | S(nC₄H₉) |
| 32.25 | Cl | S(tC₄H₉) |
| 32.26 | Cl | SPh |
| 32.27 | Cl | CCl₃ |
| 32.28 | Cl | CH₂F |
| 32.29 | Cl | CHF₂ |
| 32.30 | Cl | CF₃ |
| 32.31 | Cl | CF₂CHF₂ |
| 32.32 | Cl | SO₃H |
| 32.33 | Cl | SO₂CH₃ |
| 32.34 | Cl | SO₂C₂H₅ |
| 32.35 | Cl | SO₂(nC₃H₇) |
| 32.36 | Cl | SO₂(iC₃H₇) |
| 32.37 | Cl | SO₂(nC₄H₉) |
| 32.38 | Cl | SO₂(tC₄H₉) |
| 32.39 | Cl | SO₂Ph |
| 32.40 | Cl | NH₂ |
| 32.41 | Cl | NHCH₃ |
| 32.42 | Cl | NCH₃Ph |
| 32.43 | Cl | N(CH₃)₂ |
| 32.44 | Cl | NPh₂ |
| 32.45 | Cl | CN |
| 32.46 | Cl | NO₂ |
| 32.47 | CH₃ | F |
| 32.48 | CH₃ | Cl |
| 32.49 | CH₃ | Br |
| 32.50 | CH₃ | CH₃ |
| 32.51 | CH₃ | C₂H₅ |
| 32.53 | CH₃ | nC₃H₇ |
| 32.54 | CH₃ | iC₃H₇ |
| 32.55 | CH₃ | nC₄H₉ |
| 32.56 | CH₃ | tC₄H₉ |
| 32.57 | CH₃ | Ph |
| 32.58 | CH₃ | OH |
| 32.59 | CH₃ | OCH₃ |
| 32.60 | CH₃ | OC₂H₅ |
| 32.61 | CH₃ | O(nC₃H₇) |
| 32.62 | CH₃ | O(iC₃H₇) |

TABLE 9-continued

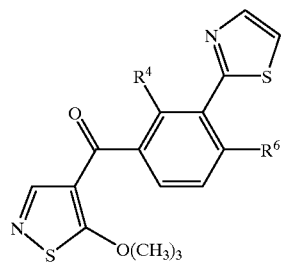

32

| No. | R⁴ | R⁶ |
|---|---|---|
| 32.63 | CH₃ | O(nC₄H₉) |
| 32.64 | CH₃ | O(tC₄H₉) |
| 32.65 | CH₃ | OPh |
| 32.66 | CH₃ | SH |
| 32.67 | CH₃ | SCH₃ |
| 32.68 | CH₃ | SC₂H₅ |
| 32.69 | CH₃ | S(nC₃H₇) |
| 32.70 | CH₃ | S(iC₃H₇) |
| 32.71 | CH₃ | S(nC₄H₉) |
| 32.72 | CH₃ | S(tC₄H₉) |
| 32.73 | CH₃ | SPh |
| 32.74 | CH₃ | CCl₃ |
| 32.75 | CH₃ | CH₂F |
| 32.76 | CH₃ | CHF₂ |
| 32.77 | CH₃ | CF₃ |
| 32.78 | CH₃ | CF₂CHF₂ |
| 32.79 | CH₃ | SO₃H |
| 32.80 | CH₃ | SO₂CH₃ |
| 32.81 | CH₃ | SO₂C₂H₅ |
| 32.82 | CH₃ | SO₂(nC₃H₇) |
| 32.83 | CH₃ | SO₂(iC₃H₇) |
| 32.84 | CH₃ | SO₂(nC₄H₉) |
| 32.85 | CH₃ | SO₂(tC₄H₉) |
| 32.86 | CH₃ | SO₂Ph |
| 32.87 | CH₃ | NH₂ |
| 32.88 | CH₃ | NHCH₃ |
| 32.89 | CH₃ | NCH₃Ph |
| 32.90 | CH₃ | N(CH₃)₂ |
| 32.91 | CH₃ | NPh₂ |
| 32.92 | CH₃ | CN |
| 32.93 | CH₃ | NO₂ |
| 32.94 | SO₂CH₃ | F |
| 32.95 | SO₂CH₃ | Cl |
| 32.96 | SO₂CH₃ | Br |
| 32.97 | SO₂CH₃ | CH₃ |
| 32.98 | SO₂CH₃ | C₂H₅ |
| 32.99 | SO₂CH₃ | nC₃H₇ |
| 32.100 | SO₂CH₃ | iC₃H₇ |
| 32.101 | SO₂CH₃ | nC₄H₉ |
| 32.102 | SO₂CH₃ | tC₄H₉ |
| 32.103 | SO₂CH₃ | Ph |
| 32.104 | SO₂CH₃ | OH |
| 32.105 | SO₂CH₃ | OCH₃ |
| 32.106 | SO₂CH₃ | OC₂H₅ |
| 32.107 | SO₂CH₃ | O(nC₃H₇) |
| 32.108 | SO₂CH₃ | O(iC₃H₇) |
| 32.109 | SO₂CH₃ | O(nC₄H₉) |
| 32.110 | SO₂CH₃ | O(tC₄H₉) |
| 32.111 | SO₂CH₃ | OPh |
| 32.112 | SO₂CH₃ | SH |
| 32.113 | SO₂CH₃ | SCH₃ |
| 32.114 | SO₂CH₃ | SC₂H₅ |
| 32.115 | SO₂CH₃ | S(nC₃H₇) |
| 32.116 | SO₂CH₃ | S(iC₃H₇) |
| 32.117 | SO₂CH₃ | S(nC₄H₉) |
| 32.118 | SO₂CH₃ | S(tC₄H₉) |
| 32.119 | SO₂CH₃ | SPh |
| 32.120 | SO₂CH₃ | CCl₃ |
| 32.121 | SO₂CH₃ | CH₂F |
| 32.122 | SO₂CH₃ | CHF₂ |
| 32.123 | SO₂CH₃ | CF₃ |

TABLE 9-continued

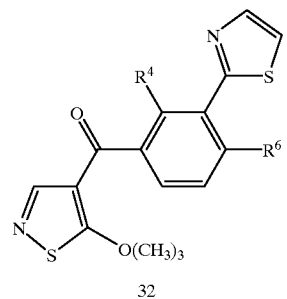

32

| No. | R⁴ | R⁶ |
|---|---|---|
| 32.124 | SO₂CH₃ | CF₂CHF₂ |
| 32.125 | SO₂CH₃ | SO₃H |
| 32.126 | SO₂CH₃ | SO₂CH₃ |
| 32.127 | SO₂CH₃ | SO₂C₂H₅ |
| 32.128 | SO₂CH₃ | SO₂(nC₃H₇) |
| 32.129 | SO₂CH₃ | SO₂(iC₃H₇) |
| 32.130 | SO₂CH₃ | SO₂(nC₄H₉) |
| 32.131 | SO₂CH₃ | SO₂(tC₄H₉) |
| 32.132 | SO₂CH₃ | SO₂Ph |
| 32.133 | SO₂CH₃ | NH₂ |
| 32.134 | SO₂CH₃ | NHCH₃ |
| 32.135 | SO₂CH₃ | NCH₃Ph |
| 32.136 | SO₂CH₃ | N(CH₃)₂ |
| 32.137 | SO₂CH₃ | NPh₂ |
| 32.138 | SO₂CH₃ | CN |
| 32.139 | SO₂CH₃ | NO₂ |

TABLE 10

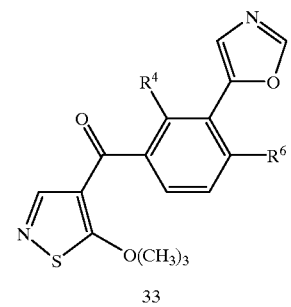

33

| No. | R⁴ | R⁶ |
|---|---|---|
| 33.1 | Cl | F |
| 33.2 | Cl | Cl |
| 33.3 | Cl | Br |
| 33.4 | Cl | CH₃ |
| 33.5 | Cl | C₂H₅ |
| 33.6 | Cl | nC₃H₇ |
| 33.7 | Cl | iC₃H₇ |
| 33.8 | Cl | nC₄H₉ |
| 33.9 | Cl | tC₄H₉ |
| 33.10 | Cl | Ph |
| 33.11 | Cl | OH |
| 33.12 | Cl | OCH₃ |
| 33.13 | Cl | OC₂H₅ |
| 33.14 | Cl | O(nC₃H₇) |
| 33.15 | Cl | O(iC₃H₇) |
| 33.16 | Cl | O(nC₄H₉) |
| 33.17 | Cl | O(tC₄H₉) |
| 33.18 | Cl | OPh |
| 33.19 | Cl | SH |
| 33.20 | Cl | SCH₃ |
| 33.21 | Cl | SC₂H₅ |
| 33.22 | Cl | S(nC₃H₇) |

TABLE 10-continued

![Structure: benzoyl compound with oxazole at one position, R4 and R6 substituents on phenyl, connected to isothiazole bearing O(CH3)3, labeled 33]

| No. | R⁴ | R⁶ |
|---|---|---|
| 33.23 | Cl | S(iC₃H₇) |
| 33.24 | Cl | S(nC₄H₉) |
| 33.25 | Cl | S(tC₄H₉) |
| 33.26 | Cl | SPh |
| 33.27 | Cl | CCl₃ |
| 33.28 | Cl | CH₂F |
| 33.29 | Cl | CHF₂ |
| 33.30 | Cl | CF₃ |
| 33.31 | Cl | CF₂CHF₂ |
| 33.32 | Cl | SO₃H |
| 33.33 | Cl | SO₂CH₃ |
| 33.34 | Cl | SO₂C₂H₅ |
| 33.35 | Cl | SO₂(nC₃H₇) |
| 33.36 | Cl | SO₂(iC₃H₇) |
| 33.37 | Cl | SO₂(nC₄H₉) |
| 33.38 | Cl | SO₂(tC₄H₉) |
| 33.39 | Cl | SO₂Ph |
| 33.40 | Cl | NH₂ |
| 33.41 | Cl | NHCH₃ |
| 33.42 | Cl | NCH₃Ph |
| 33.43 | Cl | N(CH₃)₂ |
| 33.44 | Cl | NPh₂ |
| 33.45 | Cl | CN |
| 33.46 | Cl | NO₂ |
| 33.47 | CH₃ | F |
| 33.48 | CH₃ | Cl |
| 33.49 | CH₃ | Br |
| 33.50 | CH₃ | CH₃ |
| 33.51 | CH₃ | C₂H₅ |
| 33.52 | CH₃ | nC₃H₇ |
| 33.53 | CH₃ | iC₃H₇ |
| 33.54 | CH₃ | nC₄H₉ |
| 33.55 | CH₃ | tC₄H₉ |
| 33.56 | CH₃ | Ph |
| 33.57 | CH₃ | OH |
| 33.58 | CH₃ | OCH₃ |
| 33.59 | CH₃ | OC₂H₅ |
| 33.60 | CH₃ | O(nC₃H₇) |
| 33.61 | CH₃ | O(iC₃H₇) |
| 33.62 | CH₃ | O(nC₄H₉) |
| 33.63 | CH₃ | O(tC₄H₉) |
| 33.64 | CH₃ | OPh |
| 33.65 | CH₃ | SH |
| 33.66 | CH₃ | SCH₃ |
| 33.67 | CH₃ | SC₂H₅ |
| 33.68 | CH₃ | S(nC₃H₇) |
| 33.69 | CH₃ | S(iC₃H₇) |
| 33.70 | CH₃ | S(nC₄H₉) |
| 33.71 | CH₃ | S(tC₄H₉) |
| 33.72 | CH₃ | SPh |
| 33.73 | CH₃ | CCl₃ |
| 33.74 | CH₃ | CH₂F |
| 33.75 | CH₃ | CHF₂ |
| 33.76 | CH₃ | CF₃ |
| 33.77 | CH₃ | CF₂CHF₂ |
| 33.78 | CH₃ | SO₃H |
| 33.79 | CH₃ | SO₂CH₃ |
| 33.80 | CH₃ | SO₂C₂H₅ |
| 33.81 | CH₃ | SO₂(nC₃H₇) |
| 33.82 | CH₃ | SO₂(iC₃H₇) |
| 33.83 | CH₃ | SO₂(nC₄H₉) |
| 33.84 | CH₃ | SO₂(tC₄H₉) |
| 33.85 | CH₃ | SO₂Ph |
| 33.86 | CH₃ | NH₂ |
| 33.87 | CH₃ | NHCH₃ |
| 33.88 | CH₃ | NCH₃Ph |
| 33.89 | CH₃ | N(CH₃)₂ |
| 33.90 | CH₃ | NPh₂ |
| 33.91 | CH₃ | CN |
| 33.92 | CH₃ | NO₂ |
| 33.93 | SO₂CH₃ | F |
| 33.94 | SO₂CH₃ | Cl |
| 33.95 | SO₂CH₃ | Br |
| 33.96 | SO₂CH₃ | CH₃ |
| 33.97 | SO₂CH₃ | C₂H₅ |
| 33.98 | SO₂CH₃ | nC₃H₇ |
| 33.99 | SO₂CH₃ | iC₃H₇ |
| 33.100 | SO₂CH₃ | nC₄H₉ |
| 33.101 | SO₂CH₃ | tC₄H₉ |
| 33.102 | SO₂CH₃ | Ph |
| 33.103 | SO₂CH₃ | OH |
| 33.104 | SO₂CH₃ | OCH₃ |
| 33.105 | SO₂CH₃ | OC₂H₅ |
| 33.106 | SO₂CH₃ | O(nC₃H₇) |
| 33.107 | SO₂CH₃ | O(iC₃H₇) |
| 33.108 | SO₂CH₃ | O(nC₄H₉) |
| 33.109 | SO₂CH₃ | O(tC₄H₉) |
| 33.110 | SO₂CH₃ | OPh |
| 33.111 | SO₂CH₃ | SH |
| 33.112 | SO₂CH₃ | SCH₃ |
| 33.113 | SO₂CH₃ | SC₂H₅ |
| 33.114 | SO₂CH₃ | S(nC₃H₇) |
| 33.115 | SO₂CH₃ | S(iC₃H₇) |
| 33.116 | SO₂CH₃ | S(nC₄H₉) |
| 33.117 | SO₂CH₃ | S(tC₄H₉) |
| 33.118 | SO₂CH₃ | SPh |
| 33.119 | SO₂CH₃ | CCl₃ |
| 33.120 | SO₂CH₃ | CH₂F |
| 33.121 | SO₂CH₃ | CHF₂ |
| 33.122 | SO₂CH₃ | CF₃ |
| 33.123 | SO₂CH₃ | CF₂CHF₂ |
| 33.124 | SO₂CH₃ | SO₃H |
| 33.125 | SO₂CH₃ | SO₂CH₃ |
| 33.126 | SO₂CH₃ | SO₂C₂H₅ |
| 33.127 | SO₂CH₃ | SO₂(nC₃H₇) |
| 33.128 | SO₂CH₃ | SO₂(iC₃H₇) |
| 33.129 | SO₂CH₃ | SO₂(nC₄H₉) |
| 33.130 | SO₂CH₃ | SO₂(tC₄H₉) |
| 33.131 | SO₂CH₃ | SO₂Ph |
| 33.132 | SO₂CH₃ | NH₂ |
| 33.133 | SO₂CH₃ | NHCH₃ |
| 33.134 | SO₂CH₃ | NCH₃Ph |
| 33.135 | SO₂CH₃ | N(CH₃)₂ |
| 33.136 | SO₂CH₃ | NPh₂ |
| 33.137 | SO₂CH₃ | CN |
| 33.138 | SO₂CH₃ | NO₂ |

TABLE 11

![Structure 34: benzoyl group with R4 at ortho, furan-3-yl at meta, R6 at para; attached to isothiazole bearing OC(CH3)3 at 5-position]

34

| No. | R⁴ | R⁶ |
|---|---|---|
| 34.1 | Cl | F |
| 34.2 | Cl | Cl |
| 34.3 | Cl | Br |
| 34.4 | Cl | CH₃ |
| 34.5 | Cl | C₂H₅ |
| 34.6 | Cl | nC₃H₇ |
| 34.7 | Cl | iC₃H₇ |
| 34.8 | Cl | nC₄H₉ |
| 34.9 | Cl | tC₄H₉ |
| 34.10 | Cl | Ph |
| 34.11 | Cl | OH |
| 34.12 | Cl | OCH₃ |
| 34.13 | Cl | OC₂H₅ |
| 34.14 | Cl | O(nC₃H₇) |
| 34.15 | Cl | O(iC₃H₇) |
| 34.16 | Cl | O(nC₄H₉) |
| 34.17 | Cl | O(tC₄H₉) |
| 34.18 | Cl | OPh |
| 34.19 | Cl | SH |
| 34.20 | Cl | SCH₃ |
| 34.21 | Cl | SC₂H₅ |
| 34.22 | Cl | S(nC₃H₇) |
| 34.23 | Cl | S(iC₃H₇) |
| 34.24 | Cl | S(nC₄H₉) |
| 34.25 | Cl | S(tC₄H₉) |
| 34.26 | Cl | SPh |
| 34.27 | Cl | CCl₃ |
| 34.28 | Cl | CH₂F |
| 34.29 | Cl | CHF₂ |
| 34.30 | Cl | CF₃ |
| 34.31 | Cl | CF₂CHF₂ |
| 34.32 | Cl | SO₃H |
| 34.33 | Cl | SO₂CH₃ |
| 34.34 | Cl | SO₂C₂H₅ |
| 34.35 | Cl | SO₂(nC₃H₇) |
| 34.36 | Cl | SO₂(iC₃H₇) |
| 34.37 | Cl | SO₂(nC₄H₉) |
| 34.38 | Cl | SO₂(tC₄H₉) |
| 34.39 | Cl | SO₂Ph |
| 34.40 | Cl | NH₂ |
| 34.41 | Cl | NHCH₃ |
| 34.42 | Cl | NCH₃Ph |
| 34.43 | Cl | N(CH₃)₂ |
| 34.44 | Cl | NPh₂ |
| 34.45 | Cl | CN |
| 34.46 | Cl | NO₂ |
| 34.47 | CH₃ | F |
| 34.48 | CH₃ | Cl |
| 34.49 | CH₃ | Br |
| 34.50 | CH₃ | CH₃ |
| 34.51 | CH₃ | C₂H₅ |
| 34.53 | CH₃ | nC₃H₇ |
| 34.54 | CH₃ | iC₃H₇ |
| 34.55 | CH₃ | nC₄H₉ |
| 34.56 | CH₃ | tC₄H₉ |
| 34.57 | CH₃ | Ph |
| 34.58 | CH₃ | OH |
| 34.59 | CH₃ | OCH₃ |
| 34.60 | CH₃ | OC₂H₅ |
| 34.61 | CH₃ | O(nC₃H₇) |
| 34.62 | CH₃ | O(iC₃H₇) |
| 34.63 | CH₃ | O(nC₄H₉) |
| 34.64 | CH₃ | O(tC₄H₉) |
| 34.65 | CH₃ | OPh |
| 34.66 | CH₃ | SH |
| 34.67 | CH₃ | SCH₃ |
| 34.68 | CH₃ | SC₂H₅ |
| 34.69 | CH₃ | S(nC₃H₇) |
| 34.70 | CH₃ | S(iC₃H₇) |
| 34.71 | CH₃ | S(nC₄H₉) |
| 34.72 | CH₃ | S(tC₄H₉) |
| 34.73 | CH₃ | SPh |
| 34.74 | CH₃ | CCl₃ |
| 34.75 | CH₃ | CH₂F |
| 34.76 | CH₃ | CHF₂ |
| 34.77 | CH₃ | CF₃ |
| 34.78 | CH₃ | CF₂CHF₂ |
| 34.79 | CH₃ | SO₃H |
| 34.80 | CH₃ | SO₂CH₃ |
| 34.81 | CH₃ | SO₂C₂H₅ |
| 34.82 | CH₃ | SO₂(nC₃H₇) |
| 34.83 | CH₃ | SO₂(iC₃H₇) |
| 34.84 | CH₃ | SO₂(nC₄H₉) |
| 34.85 | CH₃ | SO₂(tC₄H₉) |
| 34.86 | CH₃ | SO₂Ph |
| 34.87 | CH₃ | NH₂ |
| 34.88 | CH₃ | NHCH₃ |
| 34.89 | CH₃ | NCH₃Ph |
| 34.90 | CH₃ | N(CH₃)₂ |
| 34.91 | CH₃ | NPh₂ |
| 34.92 | CH₃ | CN |
| 34.93 | CH₃ | NO₂ |
| 34.94 | SO₂CH₃ | F |
| 34.95 | SO₂CH₃ | Cl |
| 34.96 | SO₂CH₃ | Br |
| 34.97 | SO₂CH₃ | CH₃ |
| 34.98 | SO₂CH₃ | C₂H₅ |
| 34.99 | SO₂CH₃ | nC₃H₇ |
| 34.100 | SO₂CH₃ | iC₃H₇ |
| 34.101 | SO₂CH₃ | nC₄H₉ |
| 34.102 | SO₂CH₃ | tC₄H₉ |
| 34.103 | SO₂CH₃ | Ph |
| 34.104 | SO₂CH₃ | OH |
| 34.105 | SO₂CH₃ | OCH₃ |
| 34.106 | SO₂CH₃ | OC₂H₅ |
| 34.107 | SO₂CH₃ | O(nC₃H₇) |
| 34.108 | SO₂CH₃ | O(iC₃H₇) |
| 34.109 | SO₂CH₃ | O(nC₄H₉) |
| 34.110 | SO₂CH₃ | O(tC₄H₉) |
| 34.111 | SO₂CH₃ | OPh |
| 34.112 | SO₂CH₃ | SH |
| 34.113 | SO₂CH₃ | SCH₃ |
| 34.114 | SO₂CH₃ | SC₂H₅ |
| 34.115 | SO₂CH₃ | S(nC₃H₇) |
| 34.116 | SO₂CH₃ | S(iC₃H₇) |
| 34.117 | SO₂CH₃ | S(nC₄H₉) |
| 34.118 | SO₂CH₃ | S(tC₄H₉) |
| 34.119 | SO₂CH₃ | SPh |
| 34.120 | SO₂CH₃ | CCl₃ |
| 34.121 | SO₂CH₃ | CH₂F |
| 34.122 | SO₂CH₃ | CHF₂ |
| 34.123 | SO₂CH₃ | CF₃ |

TABLE 11-continued

[Structure 34: benzoyl isothiazole with furan, R⁴, R⁶ substituents, O(CH₃)₃]

| No. | R⁴ | R⁶ |
|---|---|---|
| 34.124 | SO₂CH₃ | CF₂CHF₂ |
| 34.125 | SO₂CH₃ | SO₃H |
| 34.126 | SO₂CH₃ | SO₂CH₃ |
| 34.127 | SO₂CH₃ | SO₂C₂H₅ |
| 34.128 | SO₂CH₃ | SO₂(nC₃H₇) |
| 34.129 | SO₂CH₃ | SO₂(iC₃H₇) |
| 34.130 | SO₂CH₃ | SO₂(nC₄H₉) |
| 34.131 | SO₂CH₃ | SO₂(tC₄H₉) |
| 34.132 | SO₂CH₃ | SO₂Ph |
| 34.133 | SO₂CH₃ | NH₂ |
| 34.134 | SO₂CH₃ | NHCH₃ |
| 34.135 | SO₂CH₃ | NCH₃Ph |
| 34.136 | SO₂CH₃ | N(CH₃)₂ |
| 34.137 | SO₂CH₃ | NPh₂ |
| 34.138 | SO₂CH₃ | CN |
| 34.139 | SO₂CH₃ | NO₂ |

TABLE 12

[Structure 34: benzoyl isothiazole with furan, R⁴, R⁶ substituents, O(CH₃)₃]

| No. | R⁴ | R⁶ |
|---|---|---|
| 35.1 | Cl | F |
| 35.2 | Cl | Cl |
| 35.3 | Cl | Br |
| 35.4 | Cl | CH₃ |
| 35.5 | Cl | C₂H₅ |
| 35.6 | Cl | nC₃H₇ |
| 35.7 | Cl | iC₃H₇ |
| 35.8 | Cl | nC₄H₉ |
| 35.9 | Cl | tC₄H₉ |
| 35.10 | Cl | Ph |
| 35.11 | Cl | OH |
| 35.12 | Cl | OCH₃ |
| 35.13 | Cl | OC₂H₅ |
| 35.14 | Cl | O(nC₃H₇) |
| 35.15 | Cl | O(iC₃H₇) |
| 35.16 | Cl | O(nC₄H₉) |
| 35.17 | Cl | O(tC₄H₉) |
| 35.18 | Cl | OPh |
| 35.19 | Cl | SH |
| 35.20 | Cl | SCH₃ |
| 35.21 | Cl | SC₂H₅ |
| 35.22 | Cl | S(nC₃H₇) |

TABLE 12-continued

[Structure 34: benzoyl isothiazole with furan, R⁴, R⁶ substituents, O(CH₃)₃]

| No. | R⁴ | R⁶ |
|---|---|---|
| 35.23 | Cl | S(iC₃H₇) |
| 35.24 | Cl | S(nC₄H₉) |
| 35.25 | Cl | S(tC₄H₉) |
| 35.26 | Cl | SPh |
| 35.27 | Cl | CCl₃ |
| 35.28 | Cl | CH₂F |
| 35.29 | Cl | CHF₂ |
| 35.30 | Cl | CF₃ |
| 35.31 | Cl | CF₂CHF₂ |
| 35.32 | Cl | SO₃H |
| 35.33 | Cl | SO₂CH₃ |
| 35.34 | Cl | SO₂C₂H₅ |
| 35.35 | Cl | SO₂(nC₃H₇) |
| 35.36 | Cl | SO₂(iC₃H₇) |
| 35.37 | Cl | SO₂(nC₄H₉) |
| 35.38 | Cl | SO₂(tC₄H₉) |
| 35.39 | Cl | SO₂Ph |
| 35.40 | Cl | NH₂ |
| 35.41 | Cl | NHCH₃ |
| 35.42 | Cl | NCH₃Ph |
| 35.43 | Cl | N(CH₃)₂ |
| 35.44 | Cl | NPh₂ |
| 35.45 | Cl | CN |
| 35.46 | Cl | NO₂ |
| 35.47 | CH₃ | F |
| 35.48 | CH₃ | Cl |
| 35.49 | CH₃ | Br |
| 35.50 | CH₃ | CH₃ |
| 35.51 | CH₃ | C₂H₅ |
| 35.52 | CH₃ | nC₃H₇ |
| 35.53 | CH₃ | iC₃H₇ |
| 35.54 | CH₃ | nC₄H₉ |
| 35.55 | CH₃ | tC₄H₉ |
| 35.56 | CH₃ | Ph |
| 35.57 | CH₃ | OH |
| 35.58 | CH₃ | OCH₃ |
| 35.59 | CH₃ | OC₂H₅ |
| 35.60 | CH₃ | O(nC₃H₇) |
| 35.61 | CH₃ | O(iC₃H₇) |
| 35.62 | CH₃ | O(nC₄H₉) |
| 35.63 | CH₃ | O(tC₄H₉) |
| 35.64 | CH₃ | OPh |
| 35.65 | CH₃ | SH |
| 35.66 | CH₃ | SCH₃ |
| 35.67 | CH₃ | SC₂H₅ |
| 35.68 | CH₃ | S(nC₃H₇) |
| 35.69 | CH₃ | S(iC₃H₇) |
| 35.70 | CH₃ | S(nC₄H₉) |
| 35.71 | CH₃ | S(tC₄H₉) |
| 35.72 | CH₃ | SPh |
| 35.73 | CH₃ | CCl₃ |
| 35.74 | CH₃ | CH₂F |
| 35.75 | CH₃ | CHF₂ |
| 35.76 | CH₃ | CF₃ |
| 35.77 | CH₃ | CF₂CHF₂ |
| 35.78 | CH₃ | SO₃H |
| 35.79 | CH₃ | SO₂CH₃ |
| 35.80 | CH₃ | SO₂C₂H₅ |
| 35.81 | CH₃ | SO₂(nC₃H₇) |
| 35.82 | CH₃ | SO₂(iC₃H₇) |
| 35.83 | CH₃ | SO₂(nC₄H₉) |
| 35.84 | CH₃ | |

TABLE 12-continued

Structure 34: R⁴ and R⁶ substituted benzoyl isothiazole with O(CH₃)₃

| No. | R⁴ | R⁶ |
|---|---|---|
| 35.85 | CH₃ | SO₂(tC₄H₉) |
| 35.86 | CH₃ | SO₂Ph |
| 35.87 | CH₃ | NH₂ |
| 35.88 | CH₃ | NHCH₃ |
| 35.89 | CH₃ | NCH₃Ph |
| 35.90 | CH₃ | N(CH₃)₂ |
| 35.91 | CH₃ | NPh₂ |
| 35.92 | CH₃ | CN |
| 35.93 | CH₃ | NO₂ |
| 35.94 | SO₂CH₃ | F |
| 35.95 | SO₂CH₃ | Cl |
| 35.96 | SO₂CH₃ | Br |
| 35.97 | SO₂CH₃ | CH₃ |
| 35.98 | SO₂CH₃ | C₂H₅ |
| 35.99 | SO₂CH₃ | nC₃H₇ |
| 35.100 | SO₂CH₃ | iC₃H₇ |
| 35.101 | SO₂CH₃ | nC₄H₉ |
| 35.102 | SO₂CH₃ | tC₄H₉ |
| 35.103 | SO₂CH₃ | Ph |
| 35.104 | SO₂CH₃ | OH |
| 35.105 | SO₂CH₃ | OCH₃ |
| 35.106 | SO₂CH₃ | OC₂H₅ |
| 35.107 | SO₂CH₃ | O(nC₃H₇) |
| 35.108 | SO₂CH₃ | O(iC₃H₇) |
| 35.109 | SO₂CH₃ | O(nC₄H₉) |
| 35.110 | SO₂CH₃ | O(tC₄H₉) |
| 35.111 | SO₂CH₃ | OPh |
| 35.112 | SO₂CH₃ | SH |
| 35.113 | SO₂CH₃ | SCH₃ |
| 35.114 | SO₂CH₃ | SC₂H₅ |
| 29.115 | SO₂CH₃ | S(nC₃H₇) |
| 29.116 | SO₂CH₃ | S(iC₃H₇) |
| 29.117 | SO₂CH₃ | S(nC₄H₉) |
| 29.118 | SO₂CH₃ | S(tC₄H₉) |
| 29.119 | SO₂CH₃ | SPh |
| 29.120 | SO₂CH₃ | CCl₃ |
| 35.121 | SO₂CH₃ | CH₂F |
| 35.122 | SO₂CH₃ | CHF₂ |
| 35.123 | SO₂CH₃ | CF₃ |
| 35.124 | SO₂CH₃ | CF₂CHF₂ |
| 35.125 | SO₂CH₃ | SO₃H |
| 35.126 | SO₂CH₃ | SO₂CH₃ |
| 35.127 | SO₂CH₃ | SO₂C₂H₅ |
| 35.128 | SO₂CH₃ | SO₂(nC₃H₇) |
| 35.129 | SO₂CH₃ | SO₂(iC₃H₇) |
| 35.130 | SO₂CH₃ | SO₂(nC₄H₉) |
| 35.131 | SO₂CH₃ | SO₂(tC₄H₉) |
| 35.132 | SO₂CH₃ | SO₂Ph |
| 35.133 | SO₂CH₃ | NH₂ |
| 35.134 | SO₂CH₃ | NHCH₃ |
| 35.135 | SO₂CH₃ | NCH₃Ph |
| 35.136 | SO₂CH₃ | N(CH₃)₂ |
| 35.137 | SO₂CH₃ | NPh₂ |
| 35.138 | SO₂CH₃ | CN |
| 35.139 | SO₂CH₃ | NO₂ |

TABLE 13

Structure 36: 2-chloro-4-methylsulfonyl-benzoyl cyclopropyl-isothiazole with Z substituent

| No. | Z |
|---|---|
| 36.1 | 2-thienyl |
| 36.2 | 2-furyl |
| 36.3 | 3-methylisoxazol-5-yl |
| 36.4 | 5-thiazolyl |
| 36.5 | 4-thiazolyl |
| 36.6 | 3-methylisothiazol-5-yl |
| 36.7 | 5-phenylthiazol-2-yl |
| 36.8 | 2-pyridyl |
| 36.9 | 3-pyridyl |
| 36.10 | 4-pyridyl |
| 36.11 | 1-methyl-2-pyrrolyl |
| 36.12 | 1-methyl-1,2,4-triazol-5-yl |
| 36.13 | 2-benzothiazolyl |
| 36.14 | 2-quinolinyl |
| 36.15 | 1-methylbenzimidazol-2-yl |
| 36.16 | 2-oxazolyl |
| 36.17 | 1-phenylpyrazol-5-yl |
| 36.18 | 1-methylpyrazol-3-yl |
| 36.19 | 1-methylpyrazol-5-yl |
| 36.20 | 1,3-dimethylpyrazol-3-yl |
| 36.21 | 1-phenylpyrazol-3-yl |
| 36.22 | 1,4-dimethylpyrazol-5-yl |
| 36.23 | 1,3-dimethylpyrazol-4-yl |
| 36.24 | 1,5-dimethylpyrazol-4-yl |
| 36.25 | 1-methylpyrazol-4-yl |
| 36.26 | 1,3-dimethylpyrazol-5-yl |
| 36.27 | 4-methyloxazol-2-yl |
| 36.28 | 5-methylthiothiazol-2-yl |
| 36.29 | 4-methoxy-1-methylpyrazol-5-yl |
| 36.30 | 3-cyclopropylisoxazol-5-yl |
| 36.31 | 3-isopropylisoxazol-5-yl |
| 36.32 | (3-methylphenyl)-thiazol-2-yl |
| 36.33 | 5-methylthiazol-2-yl |
| 36.34 | 4-bromo-2-thienyl |
| 36.35 | 5-methyl-2-thienyl |
| 36.36 | 4-methyl-2-thienyl |
| 36.37 | 4-methylthiazol-2-yl |
| 36.38 | 4-chlorothiazol-2-yl |
| 36.39 | 4,5-dimethylthiazol-2-yl |
| 36.40 | 4-phenylthiazol-2-yl |
| 36.41 | 2-methoxythiazol-5-yl |
| 36.42 | 4-methyl-2-pyridyl |
| 36.43 | 6-(2-methoxyethyl)-2-pyridyl |
| 36.44 | 6-methylthio-2-pyridyl |
| 36.45 | 6-methoxy-3-pyridyl |
| 36.46 | 6-methoxy-2-pyridyl |
| 36.47 | 6-methyl-2-pyridyl |
| 36.48 | 6-(2,2,2-trifluoroethoxy)-2-pyridyl |
| 36.49 | 6-(2,2,2-trifluoroethoxy)-3-pyridyl |
| 36.50 | 5-pyrimidinyl |
| 36.51 | 6-dimethylamino-3-pyridyl |
| 36.52 | 1,2,4-thiadiazol-5-yl |
| 36.53 | 3-ethoxycarbonyl-1-methyl-pyrazol-5-yl |
| 36.54 | 2-methylthiopyrimidin-5-yl |
| 36.55 | 2-pyrimidinyl |
| 36.56 | 2-methylthiopyrimidin-4-yl |
| 36.57 | 5-methylthio-1,3,4-thiadiazol-2-yl |
| 36.58 | 5-methoxy-1,3,4-thiadiazol-2-yl |
| 36.59 | 4,5-dihydrothiazol-2-yl |
| 36.60 | 5-methyloxazol-2-yl |
| 36.61 | 5-phenyloxazol-2-yl |
| 36.62 | 2-methyloxazol-5-yl |
| 36.63 | 2-phenyloxazol-5-yl |

TABLE 13-continued

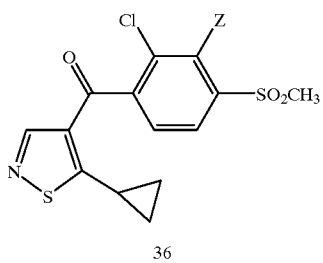

36

| No. | |
|---|---|
| 36.64 | 2-methyl-1,3,4-oxadiazol-5-yl |
| 36.65 | 2-phenyl-1,3,4-oxadiazol-5-yl |
| 36.66 | 5-trifluoromethyl-1,2,4-oxadiazol-3-yl |
| 36.67 | 5-methyl-1,2,4-oxadiazol-3-yl |
| 36.68 | 5-phenyl-1,2,4-oxadiazol-3-yl |
| 36.69 | 5-phenylisoxazol-3-yl |
| 36.70 | 1-(4-chlorophenyl)-1,2,4-triazol-2-yl |
| 36.71 | 5-cyano-4,5-dihydroisoxazol-3-yl |
| 36.72 | 5,6-dihydro-4H-1,3-thiazin-2-yl |
| 36.73 | 1,3-dithiolan-2-yl |
| 36.74 | 1,3-dioxolan-2yl |
| 36.75 | 1,3-dithian-2-yl |
| 36.76 | 1,3-dioxan-2-yl |
| 36.77 | 1,3-oxathiolan-2-yl |
| 36.78 | 1,2,4-triazol-1-yl |
| 36.79 | 3-methyl-1,2,4-thiadiazol-5-yl |
| 36.80 | 1,2,4-thiadiazol-5-yl |
| 36.81 | thiazoline-4,5-dion-2-yl |
| 36.82 | 3-oxo-3-H-1,2,4-dithiazol-5-yl |
| 36.83 | 2-oxo-2-H-1,3,4-dithiazol-5-yl |

TABLE 14

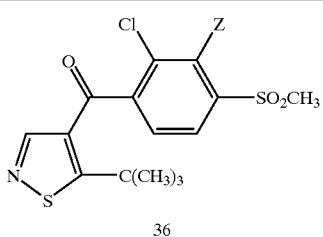

36

| No. | |
|---|---|
| 37.1 | 2-thienyl |
| 37.2 | 2-furyl |
| 37.3 | 3-methylisoxazol-5-yl |
| 37.4 | 5-thiazolyl |
| 37.5 | 4-thiazolyl |
| 37.6 | 3-methylisothiazol-5-yl |
| 37.7 | 5-phenylthiazol-2-yl |
| 37.8 | 2-pyridyl |
| 37.9 | 3-pyridyl |
| 37.10 | 4-pyridyl |
| 37.11 | 1-methyl-2-pyrrolyl |
| 37.12 | 1-methyl-1,2,4-triazol-5-yl |
| 37.13 | 2-benzothiazolyl |
| 37.14 | 2-quinolinyl |
| 37.15 | 1-methylbenzimidazol-2-yl |
| 37.16 | 2-oxazolyl |
| 37.17 | 1-phenylpyrazol-5-yl |
| 37.18 | 1-methylpyrazol-3-yl |
| 37.19 | 1-methylpyrazol-5-yl |
| 37.20 | 1,3-dimethylpyrazol-3-yl |
| 37.21 | 1-phenylpyrazol-3-yl |
| 37.22 | 1,4-dimethylpyrazol-5-yl |
| 37.23 | 1,3-dimethylpyrazol-4-yl |
| 37.24 | 1,5-dimethylpyrazol-4-yl |

TABLE 14-continued

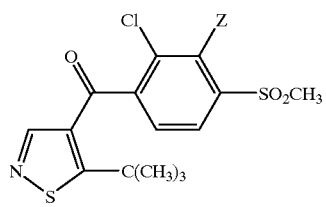

36

| No. | |
|---|---|
| 37.25 | 1-methylpyrazol-4-yl |
| 37.26 | 1,3-dimethylpyrazol-5-yl |
| 37.27 | 4-methyloxazol-2-yl |
| 37.28 | 5-methylthiothiazol-2-yl |
| 37.29 | 4-methoxy-1-methylpyrazol-5-yl |
| 37.30 | 3-cyclopropylisoxazol-5-yl |
| 37.31 | 3-isopropylisoxazol-5-yl |
| 37.32 | (3-methylphenyl)-thiazol-2-yl |
| 37.33 | 5-methylthiazol-2-yl |
| 37.34 | 4-bromo-2-thienyl |
| 37.35 | 5-methyl-2-thienyl |
| 37.36 | 4-methyl-2-thienyl |
| 37.37 | 4-methylthiazol-2-yl |
| 37.38 | 4-chlorothiazol-2-yl |
| 37.39 | 4,5-dimethylthiazol-2-yl |
| 37.40 | 4-phenylthiazol-2-yl |
| 37.41 | 2-methoxythiazol-5-yl |
| 37.42 | 4-methyl-2-pyridyl |
| 37.43 | 6-(2-methoxyethyl)-2-pyridyl |
| 37.44 | 6-methylthio-2-pyridyl |
| 37.45 | 6-methoxy-3-pyridyl |
| 37.46 | 6-methoxy-2-pyridyl |
| 37.47 | 6-methyl-2-pyridyl |
| 37.48 | 6-(2,2,2-trifluoroethoxy)-2-pyridyl |
| 37.49 | 6-(2,2,2-trifluoroethoxy)-3-pyridyl |
| 37.50 | 5-pyrimidinyl |
| 37.51 | 6-dimethylamino-3-pyridyl |
| 37.52 | 1,2,4-thiadiazol-5-yl |
| 37.53 | 3-ethoxycarbonyl-1-methyl-pyrazol-5-yl |
| 37.54 | 2-methylthiopyrimidin-5-yl |
| 37.55 | 2-pyrimidinyl |
| 37.56 | 2-methylthiopyrimidin-4-yl |
| 37.57 | 5-methylthio-1,3,4-thiadiazol-2-yl |
| 37.58 | 5-methoxy-1,3,4-thiadiazol-2-yl |
| 37.59 | 4,5-dihydrothiazol-2-yl |
| 37.60 | 5-methyloxazol-2-yl |
| 37.61 | 5-phenyloxazol-2-yl |
| 37.62 | 2-methyloxazol-5-yl |
| 37.63 | 2-phenyloxazol-5-yl |
| 37.64 | 2-methyl-1,3,4-oxadiazol-5-yl |
| 37.65 | 2-phenyl-1,3,4-oxadiazol-5-yl |
| 37.66 | 5-trifluoromethyl-1,2,4-oxadiazol-3-yl |
| 37.67 | 5-methyl-1,2,4-oxadiazol-3-yl |
| 37.68 | 5-phenyl-1,2,4-oxadiazol-3-yl |
| 37.69 | 5-phenylisoxazol-3-yl |
| 37.70 | 1-(4-chlorophenyl)-1,2,4-triazol-2-yl |
| 37.71 | 5-cyano-4,5-dihydroisoxazol-3-yl |
| 37.72 | 5,6-dihydro-4H-1,3-thiazin-2-yl |
| 37.73 | 1,3-dithiolan-2-yl |
| 37.74 | 1,3-dioxolan-2yl |
| 37.75 | 1,3-dithian-2-yl |
| 37.76 | 1,3-dioxan-2-yl |
| 37.77 | 1,3-oxathiolan-2-yl |
| 37.78 | 1,2,4-triazol-1-yl |
| 37.79 | 3-methyl-1,2,4-thiadiazol-5-yl |
| 37.80 | 1,2,4-thiadiazol-5-yl |
| 37.81 | thiazoline-4,5-dion-2-yl |
| 37.82 | 3-oxo-3-H-1,2,4-dithiazol-5-yl |
| 37.83 | 2-oxo-2-H-1,3,4-dithiazol-5-yl |

The compounds I and their agriculturally useful salts are suitable as herbicides, both in the form of isomer mixtures and in the form of the pure isomers. The herbicidal compositions comprising I are capable of effecting very good control of vegetation on non-crop areas, especially at high rates of application. In crops such as wheat, rice, maize, soya beans and cotton, they act against broad-leafed weeds and grass weeds without inflicting any considerable damage on the crop plants. This effect was observed especially at low rates of application.

Depending on the application method in question, the compounds I or compositions comprising them, can additionally be employed in a further number of crop plants to eliminate undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N. rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

The herbicidal compositions or the active ingredients can be applied pre- or post-emergence. If the active ingredients are less well compatible with certain crop plants, application techniques may be used in which the herbicidal compositions are sprayed, with the aid of the spraying equipment in such a way that they come in as little contact as possible, if any, with the leaves of the sensitive crop plants while reaching the leaves of undesirable plants which grow underneath, or the bare soil (post-directed, lay-by).

Moreover the compounds I can also be used in crops which tolerate the action of herbicides as the result of breeding, including genetic engineering methods.

The compounds I, or the herbicidal compositions comprising them, can be applied for example in the form of ready-to-spray aqueous solutions, powders, suspensions, also highly concentrated aqueous, oily or other suspensions or dispersions, emulsions, oil dispersions, pastes, dusts, materials for spreading or granules by means of spraying, atomization, dusting, spreading or pouring. The use forms depend on the intended purposes; in any case, they should guarantee the finest possible distribution of the active ingredients according to the invention.

Suitable inert additives are essentially: mineral oil fractions of medium to high boiling point, such as kerosene or diesel oil, furthermore coal-tar or oils and oils of vegetable or animal origin, aliphatic, cyclic and aromatic hydrocarbons, e.g. paraffin, tetrahydronaphthalene, alkylated naphthalene or their derivatives, alkylated benzene or their derivatives, alcohols such as methanol, ethanol, propanol, butanol or cyclohexanol, ketones such as cyclohexanone or strong polar solvents, for example amines such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, adherent, dispersant or emulsifier. Alternatively, it is possible to prepare concentrates comprising active ingredients, wetting agent, adherent, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acid, e.g. ligno-, phenol-, naphthalene- and dibutylnaphthalenesulfonic acid, or of fatty acids, alkyl- and alkylarylsulfonates, of alkyl-, lauryl ether and fatty alcohol sulfates, and salts of sulfated hexa-, hepta- and octadecanols and of fatty alcohol glycol ethers, condensates of sulfonated napthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl- and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the active ingredients I in the ready-to-use preparations can be varied within wide limits. In general, the formulations comprise 0.001 to 98% by weight, preferably 0.01 to 95% by weight, of active ingredient. The active ingredients are employed in a purity of from 90% to 100%, preferably 95% to 100% (according to NMR spectrum).

For example, compound 24.33 according to the invention can be formulated as follows:

I. 20 parts by weight of the compound 24.33 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

II. 20 parts by weight of the compound 24.33 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

III. 20 parts by weight of the active ingredient 24.33 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

IV. 20 parts by weights of the active ingredient 24.33 are mixed well with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active ingredient.

V. 3 parts by weight of the active ingredient 24.33 are mixed with 97 parts by weight of finely divided kaolin. This gives a dust which comprises 3% by weight of the active ingredient.

VI. 20 parts by weight of the active ingredient 24.33 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound 24.33 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound 24.33 is dissolved in a mixture composed of 80 parts by weight of cyclohexanone and 20 parts by weight of Emulphor EL (ethoxylated castor oil). This gives a stable emulsion concentrate.

To widen the spectrum of action and to achieve synergistic effects, the heterocycle-substituted benzoylisothiazoles I can be mixed with a large number of representatives of other groups of herbicidally active or growth-regulating active ingredients and applied concomitantly. Suitable components in mixtures are, for example, 1,2,4-thiadiazoles, 1,3,4-thiadiazoles, amides, aminophosphoric acid and its derivatives, aminotriazoles, anilides, (het)-aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF^3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4, 5,6-tetrahydrophthalimides, oxadiazoles, oxiranes, phenols, aryloxy- or heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolcarboxamides and uracils.

It may furthermore be advantageous to apply the compounds I, alone or in combination with other herbicides, concomitantly with other crop protection agents in the form of a mixture, for example with pesticides or agents for controlling phytopathogenic fungi or bacteria. Also of interest is the miscibility with mineral salt solutions, which are employed for eliminating nutritional and trace element deficiencies. Nonphytotoxic oils and oil concentrates may also be added.

Depending on the intended purpose, the season, the target plants and the growth stage, the rates of application of active ingredient are 0.001 to 3.0, preferably 0.01 to 1.0, kg/ha of active substance (a. s.)

Synthesis examples

EXAMPLE 1

Synthesis of 4-[2'-chloro-3'-(isoxazol-3"-yl)-4'-sulfonylmethylbenzoyl]-5-cyclopropylisothiazole, 24.33

The following operations are carried out with the exclusion of moisture. 9.0 g (0.04 mol) of 4-iodo-5-cyclopropylisothiazole in 200 ml of tetrahydrofuran are added, with ice-cooling, to 60 ml of a 1.4 M solution of 0.08 mol of methylenemagnesium bromide in toluene/tetrahydrofuran 3:1 (v/v)in such a way that the reaction temperature does not climb above 5° C. A solution of 25.6 g (0.08 mol) of 2-chloro-3-(isoxazol-3'-yl)-4-sulfonylmethylbenzoyl chloride in 300 ml of tetrahydrofuran are added to the reaction mixture. After the exothermic reaction has subsided, residues of organometallic compounds are hydrolyzed with 100 mol of 10% strength hydrochloric acid. The reaction mixture is taken up in diethyl ether, worked up under aqueous conditions, dried with sodium sulfate, filtered and freed from solvent in vacuo. The crude product is purified on 250 g of silica gel using mixtures of cyclohexane/ethyl acetate 10:1 to 4:1 (v/v). Yield 4.6 g (28%) of colorless amorphous solid, 270 MHz $^1$H-NMR (CDCl$_3$), δ [ppm]: 1.0 (m, 2 H), 1.4 (m, 2 H), 3.0 (m, 1 H), 3.3 (s, 3 H), 6.6 (s, 1 H), 7.3 (d, 1 H), 8.2 (s, 1 H), 8.6 (s, 1 H)

The active ingredients of the general formula 1 described in Examples 2 and 3 were synthesized in a similar manner by reacting the haloisothiazole compounds of the general formula 3 with carboxylic acid derivatives of the general formula 4 using the protocol described in Example 1.

EXAMPLE 2

4-[2'-Chloro-3'-(4",5"-dihydroisoxazol-3"-yl)-4'-sulfonylmethylbenzoyl]-5-cyclopropylisothiazole, 25.33

270 MHz $^1$H-NMR (CDCl$_3$), δ [ppm]: 3.2 (s, 3 H), 3.3 (m, 2 H), 4.6 (m, 2 H), 7.2 (m, 5 H), 7.4 (d, 1 H), 7.9 (d, 1 H), 8.9 (s, 1 H)

EXAMPLE 3

4-[2'-Chloro-3'-(thiazol-2"-yl)-4'-sulfonylmethylbenzoyl]-5-cyclopropylisothiazole, 26.33

270 MHz $^1$H-NMR (CDC$_3$), δ [ppm]: 1.0 (m, 2 H), 1.4 m, 2 H), 3.0 (m, 1 H), 3.3 (s, 3 H), 7.7 (m, 2 H), 8.0 (m, 1 H), 8.3 (d, 1 H), 8.4 (s, 1 H)

Use Examples

The herbicidal activity of the heterocycle-substituted benzoylisothiazoles of the formula 24.33 was demonstrated by greenhouse experiments:

The culture containers used were plastic flower pots containing loamy sand with approximately 3.0% humus as substrate. The seeds of the test plants were sown separately for each species.

For the pre-emergence treatment, the active ingredients which were suspended or emulsified in water were applied directly after sowing by means of finely distributing nozzles. The containers were irrigated gently to promote germination and growth and subsequently covered with translucent plastic hoods until the plant had rooted. This cover resulted in uniform germination of the test plants unless germination was adversely affected by the active ingredients.

For the post-emergence treatment, the test plants were first grown to a plant height of 3 to 15 cm, depending on the plant habit, and only then treated with the active ingredients which were suspended or emulsified in water. The test plants were either sown directly and grown in the same containers, or first grown separately as seedlings and transplanted to the test containers a few days prior to treatment.

The rate of application for the post-emergence treatment was 0.5 or 0.25 kg/ha of a.s.

The plants were kept at 10–25° C. or 20–35° C., depending on the species. The test period extended over 2 to 4 weeks. During this time, the plants were tended, and their response to the individual treatment was evaluated.

Evaluation was carried out using a scale of from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Triticum aestivum | wheat |
| Abutilon theophrasti | velvet leaf |
| Chenopodium album | lambsquarters (goosefoot) |
| Solanum nigrum | black nightshade |
| Sinapis album | white mustard |

TABLE 15

Selective herbicidal activity when used post-emergence in the greenhouse

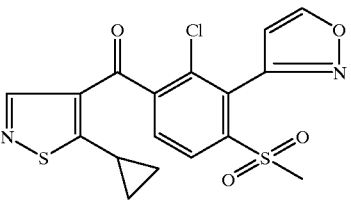

24.33

| Rate of application (kg/ha of a.s.) | 0.5 | 0.25 |
| --- | --- | --- |
| | Damage in % | |
| Test plants | | |
| TRZAW | 0 | 0 |
| ABUTH | 90 | 80 |

TABLE 15-continued

Selective herbicidal activity when used post-emergence in the greenhouse

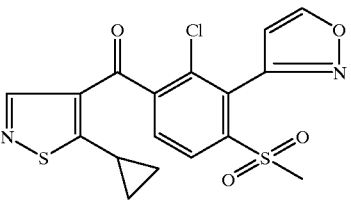

24.33

| Rate of application (kg/ha of a.s.) | 0.5 | 0.25 |
| --- | --- | --- |
| | Damage in % | |
| CHEAL | 95 | 95 |
| SINAL | 80 | 80 |
| SOLNI | 95 | 90 |

We claim:
1. A 4-benzoylisothiazole of the general formula 1

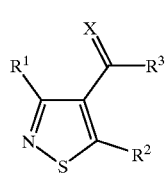

where the substituents have the following meanings:
X is oxygen or sulfur;
$R^1$ is hydrogen, alkyl, alkenyl, alkinyl; unsubstituted or substituted alkoxycarbonyl;
  unsubstituted or substituted aryl, unsubstituted or substituted heterocyclyl or unsubstituted or substituted hetaryl;
$R^2$ is hydrogen, alkyl, alkenyl, alkinyl, cycloalkyl or cycloalkenyl, it being possible for these radicals to have attached to them one or more of the following groups: halogen, alkyl, alkenyl or alkinyl;
  aryl, it being possible for this radical to have attached to it one or more of the following groups:
    alkyl, alkenyl, alkinyl, alkoxy, alkenyloxy, alkinyloxy, alkylthio or alkenylthio, it being possible for these radicals to be partially or fully halogenated or to have attached to them one or more of the following groups:
    alkoxy, alkenyloxy, aryloxy, alkylsulfonyl, alkenylsulfonyl or arylsulfonyl;
    alkylsulfonyl or alkoxycarbonyl;
    unsubstituted or substituted aryloxy or unsubstituted or substituted arylthio;
    unsubstituted or substituted mono- or dialkylamino, unsubstituted or substituted mono- or diarylamino or unsubstituted or substituted N-alkyl-N-arylamino, it being possible for alkyl and aryl to be identical or different;
    halogen, cyano or nitro;
  hetaryl or heterocyclyl, it being possible for these radicals to be partially or fully halogenated or to have attached to them one or more of the following groups:

alkyl, alkoxy or aryl, and it being possible, in the case of heterocyclyl, for at least one of the nitrogen atoms to have attached to them one of the following groups: alkyl, alkenyl, alkinyl, cycloalkyl, haloalkyl, alkoxy, alkenyloxy, alkinyloxy, cycloalkyloxy, haloalkoxy, unsubstituted or substituted aryl or unsubstituted or substituted aryloxy;

$R^3$ is a radical of the general formula 2

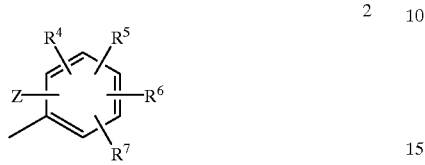

where the substituents have the following meanings:

Z is a 5- or 6-membered heterocyclic, saturated or unsaturated radical containing one to three hetero atoms selected from the group consisting of oxygen, sulfur or nitrogen and which is unsubstituted or substituted by halogen, cyano, nitro, a group —CO—$R^8$, alkyl, haloalkyl, cycloalkyl, alkoxy, haloalkoxy, alkylthio, haloalkylthio, dialkylamino or by phenyl which is unsubstituted or substituted by halogen, cyano, nitro, alkyl or haloalkyl or by an oxo group—which may, in the tautomeric form, also be present in the form of a hydroxyl group—or which together with a fused halogen-, cyano-, nitro-, alkyl- or haloalkyl-substituted phenyl ring, a fused carbocycle or a fused second heterocycle which is unsubstituted or substituted by halogen, cyano, nitro, alkyl, dialkylamino, alkoxy, haloalkoxy or haloalkyl, forms a bicyclic system, $R^4$–$R^7$ can be identical or different and independently of one another are hydrogen, alkyl, alkenyl, alkinyl, cycloalkyl, cycloalkenyl, cycloalkylalkyl, cycloalkylalkenyl, cycloalkylalkinyl, aryl, arylalkyl, arylalkenyl, arylalkinyl, hydroxyl, alkoxy, alkenyloxy, alkinyloxy, cycloalkoxy, cycloalkylalkoxy, cycloalkylalkenyloxy, cycloalkylalkinyloxy, cycloalkenyloxy, aryloxy, arylalkoxy, arylalkenyloxy, arylalkinyloxy, thio, alkylthio, alkenylthio, alkinylthio, cycloalkylthio, cycloalkylalkylthio, cycloalkylalkenylthio, cycloalkylalkinylthio, cycloalkenylthio, arylthio, arylalkylthio, arylalkenylthio, arylalkinylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkinylamino, cycloalkylamino, cycloalkenylamino, sulfonyl, alkylsulfonyl, alkenylsulfonyl, alkinylsulfonyl, cycloalkylsulfonyl, cycloalkylalkylsulfonyl, cycloalkylalkenylsulfonyl, cycloalkylalkinylsulfonyl, arylsulfonyl, arylalkylsulfonyl, arylalkenylsulfonyl, arylalkinylsulfonyl, sulfoxyl, alkylsulfoxyl, alkenylsulfoxyl, alkinylsulfoxyl, cycloalkylsulfoxyl, cycloalkylalkylsulfoxyl, cycloalkylalkenylsulfoxyl, cycloalkylalkinylsulfoxyl, arylsulfoxyl, arylalkylsulfoxyl, arylalkenylsulfoxyl, arylalkinylsulfoxyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkinylcarbonyl, cycloalkylcarbonyl, cycloalkylalkylcarbonyl, cycloalkylalkenylcarbonyl, cycloalkylalkinylcarbonyl, arylcarbonyl, arylalkylcarbonyl, arylalkenylcarbonyl, arylalkinylcarbonyl, carboxyl, alkoxycarbonyl, alkenyloxycarbonyl, alkinyloxycarbonyl, cycloalkoxycarbonyl, cycloalkylalkoxycarbonyl, cycloalkylalkenyloxycarbonyl, cycloalkylalkinyloxycarbonyl, aryloxycarbonyl, arylalkoxycarbonyl, arylalkenyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkinyloxycarbonylamino, cycloalkoxycarbonylamino, cycloalkylalkoxycarbonylamino, cycloalkylalkenyloxycarbonylamino, cycloalkylalkinyloxycarbonylamino, aryloxycarbonylamino, arylalkoxycarbonylamino, arylalkenyloxycarbonylamino, arylalkinyloxycarbonylamino, halogen, haloalkyl, haloalkenyl, haloalkinyl, haloalkoxy, haloalkenyloxy, haloalkinyloxy, haloalkylthio, haloalkenylthio, haloalkinylthio, haloalkylamino, haloalkenylamino, haloalkinylamino, haloalkylsulfonyl, haloalkenylsulfonyl, haloalkinylsulfonyl, haloalkylsulfoxyl, haloalkenylsulfoxyl, haloalkinylsulfoxyl, haloalkylcarbonyl, haloalkenylcarbonyl, haloalkinylcarbonyl, haloalkoxycarbonyl, haloalkenyloxycarbonyl, haloalkinyloxycarbonyl, haloalkylaminocarbonyl, haloalkenylaminocarbonyl, haloalkinylaminocarbonyl, haloalkoxycarbonylamino, haloalkenyloxycarbonylamino, haloalkinyloxycarbonylamino, cyano or nitro, or one of the following groups:

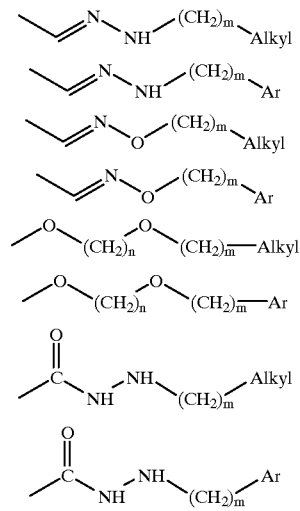

n = 1, 2, 3; m = 0, 1, 2, 3

$R^4$, $R^5$ together can form a five- or six-membered saturated or unsaturated aromatic or non-aromatic unsubstituted or substituted alkylene, alkenylene or alkdienylene chain;

R⁸ is alkyl, haloalkyl, alkoxy, or NR⁹R¹⁰,

R⁹ is hydrogen or alkyl, and

R¹⁰ is alkyl, or a salt of a 4-benzoylisothiazole of the general formula 1 conventionally used in agriculture.

2. A 4-benzoylisothiazole of the general formula 1 as claimed in claim 1 where X is oxygen.

3. A 4-benzoylisothiazole of the general formula 1 as claimed in claim 1 where R¹ is hydrogen or unsubstituted or substituted alkoxycarbonyl.

4. A 4-benzoylisothiazole of the general formula 1 as claimed in claim 1 where R² is alkyl, cycloalkyl, aryl which can be monosubstituted or polysubstituted by halogen or haloalkyl, or heteraryl which can be monosubstituted or poly-substituted by halogen.

5. A 4-benzoylisothiazole of the general formula 1 as claimed in claim 1 where R² is methyl, ethyl, isopropyl, tert-butyl, cyclopropyl, 1-methylcyclopropyl, 3-trifluoromethylphenyl, 2,4-difluorophenyl, 1,3-benzodioxolyl, 2,2-difluoro-1,3-benzodixolyl, 1,3-benzoxathiolyl, 3,3-dioxo-1,3-benzoxathiolyl, benzoxazolyl, pyrazolyl or thienyl.

6. A 4-benzoylisothiazole of the general formula 1 as claimed in claim 1 where R³ is a radical of the general formula 2

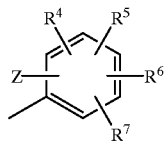

2 where Z has the meanings given in claim 1 and the substituents R⁴–R⁷ have the following meanings:

R⁴–R⁷ can be identical or different and independently of one another are hydrogen, alkyl, cycloalkyl, aryl, hydroxy, alkoxy, cycloalkoxy, aryloxy, thio, alkylthio, cycloalkylthio, arylthio, amino, in each case unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, unsubstituted or substituted mono- or dialkylaminocarbonyl or mono- or diarylaminocarbonyl or N-alkyl-N-arylaminocarbonyl, it being possible for alkyl and aryl to be identical or different, alkoxycarbonylamino, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino, cyano or nitro;

R⁴, R⁵ together can form a five- or six-membered saturated or unsaturated aromatic or non-aromatic unsubstituted or substituted alkylene, alkenylene or alkdienylene chain.

7. A 4-benzoylisothiazole of the general formula 1 as claimed in claim 1 where R³ is a radical of the general formula 2a

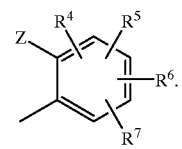

2a

8. A 4-benzoylisothiazole of the general formula 1 as claimed in claim 1 where R³ is a radical of the general formula 2b

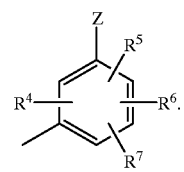

2b

9. A 4-benzoylisothiazole of the general formula 1 as claimed in claim 1 where R³ is a radical of the general formula 2c

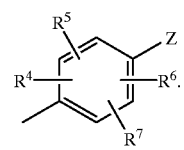

2c

10. A 4-benzoylisothiazole of the general formula 1 as claimed in claim 1 where R³ is a radical of the general formula 2d

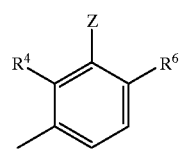

2d and R⁴ and R⁶ are identical or different and independently of one another are alkyl, alkoxy, alkylsulfonyl, aryloxy, halogen or haloalkyl.

11. A 4-benzoylisothiazole of the general formula 1 as claimed in claim 1 where R³ is a radical of the general formula 2d

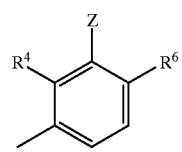

2d and R⁴ and R⁶ are identical or different and independently of one another are fluorine, chlorine, bromine, methylsulfonyl, ethylsulfonyl, difluoromethyl, trifluormethyl, tetrafluorethyl or trichloromethyl.

12. A 4-benzoylisothiazole of the general formula 1 as claimed in claim 1 where $R^3$ is a radical of the general formula 2e

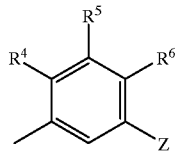

and $R^4$, $R^5$ and $R^6$ are identical or different and independently of one another are alkyl, alkoxy, aryloxy, alkylsulfonyl, halogen or haloalkyl.

13. A 4-benzoylisothiazole of the general formula 1 as claimed in claim 12, where $R^3$ is a radical of the general formula 2e

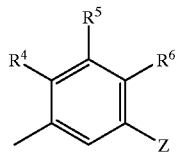

and $R^4$, $R^5$ and $R^6$ are identical or different and independently of one another are methoxy, ethoxy, phenoxy, methylsulfonyl, ethylsulfonyl, fluorine, chlorine, bromine, iodine, difluoromethyl, trifluoromethyl, tetrafluoroethyl or trichloromethyl.

14. A process for the preparation of a 4-benzoylisothiazole of the general formula 1 as claimed in claim 1, which comprises reacting a haloisothiazole compound of the general formula 3 where Y is halogen

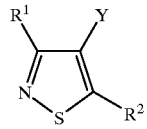

with elemental magnesium or an organomagnesium or organolithium compound and with a carboxylic acid derivative of the general formula 4,

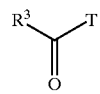

where T is halogen, N-alkoxy-N-alkylamino or cyano in a temperature range of from −78° C. to 111° C. in the presence of an inert solvent.

15. A process for the preparation of a 4-benzoylisothiazole of the general formula 1 as claimed in claim 1, which comprises reacting a halobenzene of the general formula 5

where Y is halogen, with elemental magnesium or an organomagnesium or organolithium compound and with an isothiazolecarboxylic acid derivative of the general formula 6a or 6b,

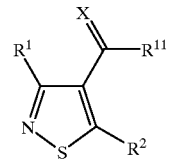

where $R^{11}$ is halogen or N-alkoxy-N-alkylamino in a temperature range of from −78° C. to 111° C. in the presence of an inert solvent.

16. A herbicidal composition comprising a 4-benzoylisothiazole of the general formula 1 as claimed in claim 1 and inert additives.

17. A method of controlling undesirable vegetation, which comprises treating the undesired plants and/or their environment with a herbicidally active amount of a 4-benzoylisothiazole of the general formula 1 as claimed in claim 1.

* * * * *